(12) United States Patent
Drew et al.

(10) Patent No.: US 8,826,908 B2
(45) Date of Patent: Sep. 9, 2014

(54) ELBOW FOR MASK ASSEMBLY

(75) Inventors: Joanne E. Drew, Balgowlah Heights (AU); Memduh Guney, Killara (AU); Amal S. Amarasinghe, West Pennant Hills (AU); Perry D. Lithgow, Glenwood (AU); Anthony M Ging, Vancouver (CA); Borivoje Ljubojevic, Ryde (AU); Donald Darkin, Dural (AU); Grahame B. Aston, Yagoona (AU)

(73) Assignee: ResMed Limited, Bella Vista (AU)

( * ) Notice: Subject to any disclaimer, the term of this patent is extended or adjusted under 35 U.S.C. 154(b) by 675 days.

(21) Appl. No.: 12/000,601

(22) Filed: Dec. 14, 2007

(65) Prior Publication Data
US 2008/0099014 A1 May 1, 2008

Related U.S. Application Data

(63) Continuation of application No. 11/320,633, filed on Dec. 30, 2005, now Pat. No. 7,316,230, which is a continuation of application No. 10/655,621, filed on Sep. 5, 2003, now Pat. No. 7,011,090, and a continuation-in-part of application No. 10/235,846, filed on Sep. 6, 2002, now Pat. No. 6,823,869.

(60) Provisional application No. 60/424,695, filed on Nov. 8, 2002, provisional application No. 60/474,928, filed on Jun. 3, 2003, provisional application No. 60/317,486, filed on Sep. 7, 2001, provisional application No. 60/342,854, filed on Dec. 28, 2001.

(51) Int. Cl.
*A61M 16/08* (2006.01)
*A61M 39/10* (2006.01)
*A61M 16/06* (2006.01)

(52) U.S. Cl.
CPC ....... *A61M 16/0816* (2013.01); *A61M 16/0875* (2013.01); *A61M 39/10* (2013.01); *A61M 16/08* (2013.01); *A61M 16/06* (2013.01)
USPC ............ 128/206.21; 128/205.25; 128/200.24; 128/202.27

(58) Field of Classification Search
USPC ............. 128/200.24, 206.21, 206.27, 207.11, 128/202.27
See application file for complete search history.

(56) References Cited

U.S. PATENT DOCUMENTS 1,081,745 A 12/1913 Johnston
2,313,999 A * 3/1943 Kreiselman .............. 128/206.26

(Continued)

FOREIGN PATENT DOCUMENTS

DE 29723101 U1 7/1998
EP 1 027 905 8/2000

(Continued)

OTHER PUBLICATIONS

Japanese Office Action for corresponding Japanese Application No. 2004-569778, mailed Feb. 2, 2010 (8 pages).

(Continued)

*Primary Examiner* — Annette Dixon
(74) *Attorney, Agent, or Firm* — Nixon & Vanderhye P.C.

(57) ABSTRACT

An elbow assembly for use in a respiratory mask, which includes an elbow, an inlet port, an exhaust port, and a baffle separating the inlet port from the exhaust port. A mask assembly includes a cushion comprising at least one gusset and an aperture for connection to the elbow assembly.

34 Claims, 77 Drawing Sheets

(56) References Cited

U.S. PATENT DOCUMENTS

| | | | |
|---|---|---|---|
| 3,724,499 A * | 4/1973 | Huniu | 137/615 |
| 4,266,540 A | 5/1981 | Panzik et al. | |
| 4,446,864 A * | 5/1984 | Watson et al. | 128/207.14 |
| 4,655,213 A | 4/1987 | Rapoport et al. | |
| 4,676,241 A | 6/1987 | Webb et al. | |
| 4,713,844 A | 12/1987 | Westgate | |
| 4,794,921 A | 1/1989 | Lindkvist | |
| 4,944,310 A | 7/1990 | Sullivan | |
| 5,243,971 A | 9/1993 | Sullivan et al. | |
| 5,245,995 A | 9/1993 | Sullivan et al. | |
| 5,349,949 A | 9/1994 | Schegerin | |
| 5,441,046 A | 8/1995 | Starr et al. | |
| RE35,339 E | 10/1996 | Rapoport | |
| 5,560,354 A | 10/1996 | Berthon-Jones et al. | |
| 5,657,752 A | 8/1997 | Landis et al. | |
| 5,662,101 A | 9/1997 | Ogden et al. | |
| 5,694,922 A | 12/1997 | Palmer | |
| 5,704,345 A | 1/1998 | Berthon-Jones | |
| 5,735,271 A * | 4/1998 | Lorenzen et al. | 128/207.16 |
| 5,746,201 A | 5/1998 | Kidd | |
| 5,918,598 A | 7/1999 | Belfer et al. | |
| 5,921,239 A | 7/1999 | McCall et al. | |
| 5,937,851 A | 8/1999 | Serowski et al. | |
| 5,947,121 A | 9/1999 | Marshall | |
| 6,112,745 A | 9/2000 | Lang | |
| 6,112,746 A | 9/2000 | Kwok et al. | |
| 6,119,693 A | 9/2000 | Kwok et al. | |
| 6,119,694 A | 9/2000 | Correa et al. | |
| 6,192,886 B1 | 2/2001 | Rudolph | |
| 6,347,631 B1 | 2/2002 | Hansen et al. | |
| 6,412,487 B1 | 7/2002 | Gunaratnam et al. | |
| 6,412,488 B1 | 7/2002 | Barnett et al. | |
| 6,418,928 B1 | 7/2002 | Bordewick et al. | |
| 6,422,238 B1 | 7/2002 | Lithgow | |
| 6,435,181 B1 | 8/2002 | Jones et al. | |
| 6,450,166 B1 * | 9/2002 | McDonald et al. | 128/206.27 |
| 6,467,483 B1 | 10/2002 | Kopacko et al. | |
| 6,491,034 B1 | 12/2002 | Gunaratnam et al. | |
| 6,505,623 B1 | 1/2003 | Hansen | |
| 6,530,373 B1 | 3/2003 | Patron et al. | |
| 6,536,435 B1 | 3/2003 | Fecteau et al. | |
| 6,581,594 B1 | 6/2003 | Drew et al. | |
| 6,595,207 B1 * | 7/2003 | McDonald et al. | 128/200.28 |
| 6,631,719 B2 * | 10/2003 | McDonald et al. | 128/207.11 |
| 6,662,803 B2 | 12/2003 | Gradon et al. | |
| D485,905 S | 1/2004 | Moore et al. | |
| 6,675,796 B2 | 1/2004 | McDonald | |
| 6,679,265 B2 | 1/2004 | Strickland et al. | |
| 6,691,707 B1 * | 2/2004 | Gunaratnam et al. | 128/206.21 |
| 6,763,828 B2 | 7/2004 | Arnott | |
| 6,823,869 B2 | 11/2004 | Raje et al. | |
| 6,851,425 B2 | 2/2005 | Jaffre et al. | |
| 6,851,427 B1 | 2/2005 | Nashed | |
| 6,892,729 B2 | 5/2005 | Smith et al. | |
| 6,907,882 B2 | 6/2005 | Ging et al. | |
| 7,011,090 B2 * | 3/2006 | Drew et al. | 128/202.27 |
| 7,316,230 B2 * | 1/2008 | Drew et al. | 128/202.27 |
| 7,487,772 B2 * | 2/2009 | Ging et al. | 128/202.27 |
| 7,597,100 B2 * | 10/2009 | Ging et al. | 128/204.18 |
| 7,934,501 B2 * | 5/2011 | Fu et al. | 128/206.21 |
| 2001/0032648 A1 | 10/2001 | Jestrabek-Hart | |
| 2002/0029780 A1 | 3/2002 | Frater et al. | |
| 2003/0196656 A1 | 10/2003 | Moore et al. | |
| 2003/0196657 A1 | 10/2003 | Ging et al. | |
| 2003/0196658 A1 | 10/2003 | Ging et al. | |
| 2003/0196662 A1 | 10/2003 | Ging et al. | |
| 2004/0112385 A1 | 6/2004 | Drew et al. | |
| 2006/0102185 A1 | 5/2006 | Drew et al. | |
| 2008/0276937 A1 * | 11/2008 | Davidson et al. | 128/204.18 |
| 2009/0194111 A1 * | 8/2009 | Fu et al. | 128/205.24 |

FOREIGN PATENT DOCUMENTS

| | | |
|---|---|---|
| EP | 1057494 A2 | 12/2000 |
| EP | 1258266 A1 | 11/2002 |
| EP | 1314446 A2 | 5/2003 |
| EP | 1 356 844 A2 | 10/2003 |
| GB | 799225 | 8/1958 |
| GB | 2379886 A | 3/2003 |
| JP | 2000-233024 | 8/2000 |
| JP | 2000-279520 | 10/2000 |
| JP | 2002-95751 | 4/2002 |
| JP | WO 02/051486 A1 | 7/2002 |
| JP | 2003-502116 | 1/2003 |
| JP | 2004-507333 | 3/2004 |
| JP | 2004-522487 | 7/2004 |
| WO | WO 97/33641 | 9/1997 |
| WO | WO 98/12965 | 4/1998 |
| WO | WO 98/34665 | 8/1998 |
| WO | WO 99/61088 | 12/1999 |
| WO | WO 00/78381 | 12/2000 |
| WO | WO 00/78381 A1 | 12/2000 |
| WO | WO 00/78384 | 12/2000 |
| WO | WO 01/97893 | 12/2001 |
| WO | WO 02/20078 A1 | 3/2002 |

OTHER PUBLICATIONS

PCT International Search Report dated Oct. 15, 2003.
U.S. Appl. No. 60/377,254, filed Aug. 2002, Moore et al.
U.S. Appl. No. 60/397,195, filed Jul. 2002, Moore et al.
U.S. Appl. No. 60/402,509, filed Aug. 2002, Moore et al.
Japanese Office Action and English Translation for Co-Pending Japanese Application No. 2004-569778, issued Mar. 25, 2009, 6 pages.
Supplementary European Search Report for copending European Application No. 03793492, mailed Jun. 15, 2010, 3 pages.
Japanese Office Action issued in related Japanese Appln. No. 2010-106600 (Feb. 28, 2012).
First Examination Report dated Jan. 30, 2013 in corresponding New Zealand Application No. 605941 (2 pages total).
Further Examination Report dated Jan. 30, 2013 in corresponding New Zealand Application No. 595537 (2 pages total).
Office Action issued in a corresponding Japanese Application No. 2011-183475 with English translation thereof (Feb. 26, 2013).
Office Action issued in a corresponding Japanese Application No. 2010-106600 (Dec. 4, 2012) with English translation thereof.
Notice of Allowance issued in a corresponding Japanese Patent Application No. 2010-106600 on Aug. 20, 2013.
Notice of Allowance issued in corresponding Japanese Patent Application No. 2011-183475 on Dec. 24, 2013.
Notice of Reasons for Rejection issued Apr. 7, 2014 in Japanese Patent Application No. 2013-110713 with English-language translation thereof.

* cited by examiner

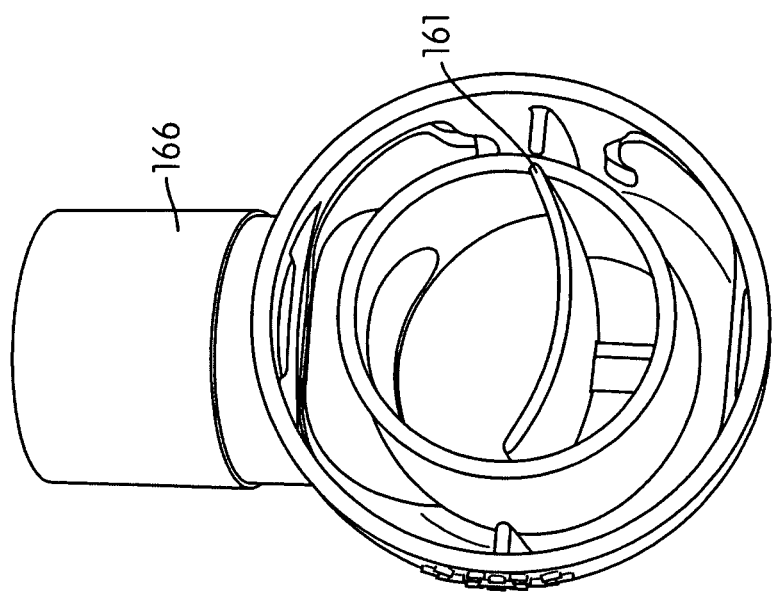
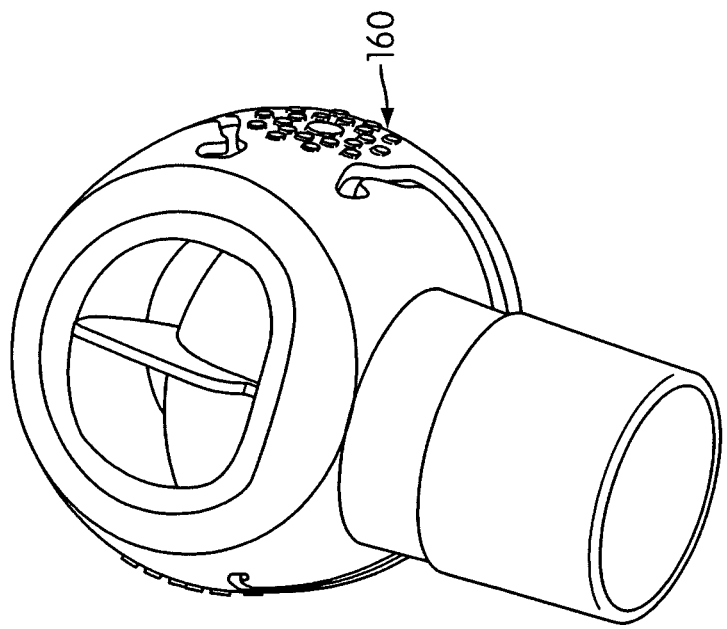
FIG. 24b
FIG. 24a

← FROM BLOWER

MASK CAVITY

ELBOW FOR MASK ASSEMBLY

CROSS-REFERENCE TO PRIORITY APPLICATIONS

The present application is a continuation of U.S. application Ser. No. 11/320,633, now allowed, which is a continuation of U.S. application Ser. No. 10/655,621, filed Sep. 5, 2003, now U.S. Pat. No. 7,011,090, which claims the benefit of U.S. Provisional Application Ser. No. 60/424,695 filed Nov. 8, 2002 and U.S. Provisional Application Ser. No. 60/474,928 filed Jun. 3, 2003. U.S. application Ser. No. 10/655,621 additionally is a Continuation-In-Part of U.S. Non-Provisional application Ser. No. 10/235,846 filed Sep. 6, 2002, now U.S. Pat. No. 6,823,869, which in turn claims priority to U.S. Provisional Application Ser. No. 60/317,486 filed Sep. 7, 2001 and U.S. Provisional Application Ser. No. 60/342,854 filed Dec. 28, 2001. Each of the above identified applications is incorporated herein by reference in its entirety.

BACKGROUND OF THE INVENTION

1. Field of the Invention

The invention relates to a mask frame and elbow for use with a mask system for Non-invasive Positive Pressure Ventilation (NPPV) and for continuous positive airway pressure (CPAP) therapy of sleep disordered breathing (SDB) conditions such as obstructive sleep apnea (OSA).

2. Background of the Invention

The use of NPPV for treatment of SDB, such as OSA was pioneered by Sullivan (see, for example, U.S. Pat. No. 4,944,310, the contents of which are hereby incorporated in their entirety by reference). Apparatus for this treatment involves a blower which delivers a supply of air at positive pressure to a patient interface via an air delivery conduit. The patient interface may take several forms such as nasal masks and nose and mouth masks. Patients must wear a mask all night while sleeping to receive the therapy. Masks typically comprise a rigid shell or frame and a soft face-contacting cushion that spaces the frame away from the face and forms a seal with the patient's face. The frame and cushion define a cavity which receives the nose, or nose and mouth. The mask is held in position by headgear, which usually comprises an arrangement of straps that passes along the side of the face to the back or crown of the head.

Kwok et al. (U.S. Pat. No. 6,112,746), the contents of which are hereby incorporated in their entirety by reference, describe a nasal mask and mask cushion. The mask cushion is a substantially triangularly shaped frame from which extends a membrane. The mask frame has a scalloped edge by which the mask cushion is affixed to a mask frame. The membrane has an aperture into which the user's nose is received. The membrane is spaced away from the rim of the frame, and its outer surface has substantially the same shape as the rim.

Frater et al. (PCT Patent Application AU01/00746, published as WO 01/97893), the contents of which are hereby incorporated in their entirety by reference, describes a mask system for delivering air to a user includes a suspension mechanism to allow relative movement between a face-contacting cushion and a mask frame. The suspension mechanism also provides a predetermined force to the cushion that is a function of mask pressure, displacement of the cushion, or both.

During the course of the respiratory cycle patients inhale air, largely comprising a mixture of nitrogen and oxygen, and exhale a mixture of gases including a relatively higher fraction of $CO_2$. In a nasal mask system where the patient breathes through the nose, there can be a build-up of $CO_2$ in the mask cavity which can lead to undesirable $CO_2$ re-breathing. Hence a variety of vents have been developed for use with masks. The amount of $CO_2$ in the mask cavity is a function of vent geometry, mask geometry, flow patterns within the mask and the amount of dead-space within the mask cavity.

The mask is typically joined to the air delivery conduit using a friction fit. Since the blower is typically placed beside a patient's bed, it is typical that the air delivery conduit be at least 1 meter long. Occasionally, movement of the air delivery conduit can disrupt the seal. Furthermore, some patients prefer to have the conduit in one position (for example passing over their heads), whereas other patients prefer to have it in another position (for example to the left or right side). Hence swivel elbows were developed for some masks.

Swivel elbows typically include: (i) a cylindrical first portion, having an axis aligned in a first direction and being adapted for connection to an air delivery conduit; and (ii) a cylindrical second portion, having an axis aligned in a second direction and being adapted for connection to a frame of a mask.

The first and second directions typically are at right angles to one another. The first portion has an outer diameter slightly smaller than the inner diameter of typical air delivery conduit tubing, so that the tubing can overfit the first portion and be held in position by friction. A free end of the second portion is adapted to pass through an orifice in the mask frame. Such known swivel elbows typically include a vent. While some vents are simply holes, such as those in the Puritan-Bennett SOFTFIT mask (FIG. 10a), others are more sophisticated, such as those used with the ResMed ULTRA MIRAGE® mask.

A problem with the prior art swivel elbows incorporating a simple vent, such as the Puritan-Bennett SOFTFIT (FIG. 10a), the Respironics CONTOUR-DELUXE (FIG. 10c) and the related art Tiara ADVANTAGE elbows (FIG. 10b), is that air from the blower can simply short-circuit the mask and pass straight out of the vent. This is a particular problem when a patient is being given supplemental oxygen, which is expensive. A significant portion of the oxygen being fed to the elbow simply passes out the vent without entering the mask.

FIGS. 8a, 8b, 9a, and 9b show prior art elbows manufactured by ResMed Limited for the STANDARD and MODULAR masks respectively. FIGS. 8c, 8d, 9c, and 9d show related art elbows manufactured by ResMed Limited for the ULTRA MIRAGE® and MIRAGE® VISTA masks respectively. FIGS. 11a to 11f show prior art elbows in the WHISPER swivel I and swivel II masks manufactured by Respironics. FIGS. 12 and 13 show a prior art mask SERENITY mask manufactured by DeVilbiss in which the interior of the nasal cavity includes a baffle B for redirecting incoming gas.

A mask that includes a cushion with a gusset will have a larger cavity, and hence more dead-space than a mask without a gusset, everything else being equal. Hence in a mask assembly with a gusset, particular attention needs to be paid to venting the mask to ensure that sufficient $CO_2$ is washed out by a continuous influx of fresh air.

Since the mask is to be used by sleeping users, it is also desirable to reduce or eliminate noise from all sources, including those caused by the venting of gases from the mask.

Kwok (PCT/AU98/00067, published as WO 98/34665), the contents of which are hereby incorporated in their entirety by reference, describes a mask and a vent. In one form the vent comprises a soft flexible insert piece with a series of orifices.

Drew et al. (PCT/AU00/00636 published as WO 00/78381), the contents of which are hereby incorporated in their entirety by reference, disclose a connector that comprises a mask end for connecting, in fluid communication, with the interior of a respiratory mask and a supply conduit end disposed at an angle to the mask end for connecting, in fluid communication, with the outlet of a breathable gas supply conduit. The connector also includes a gas washout vent passage having an inlet adjacent to, or forming part of, the mask end in fluid communication with the interior of the respiratory mask and an outlet in fluid communication with the atmosphere. The outlet includes an interior surface that forms a smooth prolongation with an adjacent exterior surface of the connector. The vent outlet is disposed on the side of the connector remote the mask end, has a generally part-annular cross section and is adapted to direct the washout gas in a direction substantially perpendicular to the longitudinal axis of the mask end and substantially parallel to the longitudinal axis of the supply conduit end towards the supply conduit end.

Moore et al. (co-pending provisional application Ser. No. 60/402,509, filed Aug. 12, 2002), the contents of which are hereby incorporated in their entirety by reference, describe a mask system including a swivel elbow with a vent.

Correa et al. (U.S. Pat. No. 6,119,694) discloses a nasal mask assembly with a miniature nare seal. The mask assembly includes a conduit receptor that attaches to a gas delivery tube. Downstream of the conduit receptor is a bore that receives a stem having opposed flanges. The flanges separate the incoming gas into a plurality of channels, such that the gas is provided to one of a plurality of spatial regions in the interior of the nare seal.

While the vents and connectors described in the previous references provide adequate intake of breathable air/gas and venting for masks that have a small amount of dead-space, e.g., without gussets, they may be inadequate to provide air intake and $CO_2$ removal in masks that have larger amounts of dead-space, e.g., with gussets. Therefore, there exists a need in the art for a swivel elbow and mask assembly that overcome the problems listed above.

SUMMARY OF THE INVENTION

A first aspect of the invention is directed towards providing an elbow for a mask which provides improved flow patterns for inlet and exhaust flows.

A second aspect of the invention is directed towards providing an elbow, comprising a baffle.

A third aspect of the invention is directed towards providing an elbow for a mask that includes an exhaust port for a mask and a baffle that extends from the elbow into the mask cavity.

Another aspect of the invention is directed towards providing a swivel elbow including an exhaust port for a mask, wherein the swivel elbow includes structure for ensuring that fresh air from the blower does not directly reach the vent.

Another aspect of the invention is directed towards a swivel elbow assembly that is easy to assemble and disassemble.

Another aspect of the invention is directed towards a mask assembly using an elbow assembly that permits better intake of breathable air and/or better removal of exhaust air.

Another aspect of the invention is directed towards a mask assembly using an elbow assembly that is quieter for the user and/or bed partner.

Another aspect of the invention is directed towards an elbow assembly for a respiratory mask comprising an elbow, including a portion adapted to engage a gas delivery tube and another portion that is detachable and is coupled to the mask.

The elbow further defines an inlet port to deliver incoming gas into a nasal breathing cavity defined by the mask and an exhaust port separated from the inlet port by a curved baffle.

Another aspect of the invention is directed towards providing an elbow for a mask comprising: (i) a portion for connecting to a gas delivery tube; (ii) a portion that is connected to a mask cavity; (iii) an inlet port to deliver incoming gas into the breathing cavity; (iv) an exhaust port to washout $CO_2$; and (v) a baffle that separates the inlet and exhaust ports.

Another aspect of the invention is directed towards a baffle for use with an elbow and mask assembly, for directing the inlet and outlet flows of the mask assembly.

A further aspect of the invention is directed towards a mask assembly comprising a mask frame, a mask cushion, and an elbow assembly.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF FIGURES

FIG. 4b is a front view of the swivel elbow shown in FIG. 4a;

FIG. 5b is a left side view of the respiratory mask assembly shown in FIG. 5a;

FIG. 5c is a right side view of the respiratory mask assembly shown in FIG. 5a;

FIG. 5d is a top view of the respiratory mask assembly shown in FIG. 5a;

FIG. 6a is a front view of the respiratory mask frame shown in FIG. 5a;

FIG. 6b is a rear view of the respiratory mask frame shown in FIG. 6a;

FIG. 6c is a front perspective view of the respiratory mask frame shown in FIG. 6a;

FIG. 6d is a rear perspective view of the respiratory mask frame shown in FIG. 6a;

FIG. 6e is a cross-sectional view along line 6e-6e of the respiratory mask frame shown in FIG. 6a;

FIG. 6f is a right side view of the respiratory mask frame shown in FIG. 6a;

FIG. 6h is a cross-sectional view along line 6h-6h of the respiratory mask frame shown in FIG. 6a;

FIG. 20b is a rear perspective view of the swivel elbow shown in FIG. 20a;

FIG. 21a is a front view of the swivel elbow shown in FIG. 20a;

FIG. 21b is a top view of the swivel elbow shown in FIG. 21a;

FIG. 21c is a bottom view of the swivel elbow shown in FIG. 21a;

FIG. 21d is a right side view of the swivel elbow shown in FIG. 21a;

FIG. 21e is a rear view of the swivel elbow shown in FIG. 21a;

FIG. 21g is a cross-sectional view along line 21g-21g of the swivel elbow shown in FIG. 21a;

FIG. 22b is a rear perspective view of the swivel elbow shown in FIG. 22a;

FIG. 23a is a front view of the swivel elbow shown in FIG. 22a;

FIG. 23b is a top view of the swivel elbow shown in FIG. 23a;

FIG. 23c is a bottom view of the swivel elbow shown in FIG. 23a;

FIG. 23d is a right side view of the swivel elbow shown in FIG. 23a;

FIG. 23e is a rear view of the swivel elbow shown in FIG. 23a;

FIG. 23g is a cross-sectional view along line 23g-23g of the swivel elbow shown in FIG. 23a;

FIG. 24a is a front perspective view of a swivel elbow according to another embodiment of the invention;

FIG. 24b is a rear perspective view of the swivel elbow shown in FIG. 24a;

FIG. 25a is a front view of the swivel elbow shown in FIG. 24a;

FIG. 25b is a top view of the swivel elbow shown in FIG. 25a;

FIG. 25c is a bottom view of the swivel elbow shown in FIG. 25a;

FIG. 25d is a right side view of the swivel elbow shown in FIG. 25a;

FIG. 25e is a rear view of the swivel elbow shown in FIG. 25a;

FIG. 25f is a cross-sectional view along line 25f-25f of the swivel elbow shown in FIG. 25e;

FIG. 25g is a cross-sectional view along line 25g-25g of the swivel elbow shown in FIG. 25a;

FIG. 25h is a detailed view of a portion of the swivel elbow shown in FIG. 25g;

FIG. 25i is another front perspective view of the swivel elbow shown in FIG. 24a at a slightly different angle;

FIG. 25j is another rear perspective view of the swivel elbow shown in FIG. 24b at a slightly different angle;

FIG. 26a is a front perspective view of a swivel elbow according to another embodiment of the invention;

FIG. 26b is a rear perspective view of the swivel elbow shown in FIG. 26a;

FIG. 27a is a front view of the swivel elbow shown in FIG. 26a;

FIG. 27b is a top view of the swivel elbow shown in FIG. 27a;

FIG. 27c is a bottom view of the swivel elbow shown in FIG. 27a;

FIG. 27d is a right side view of the swivel elbow shown in FIG. 27a;

Figure 26B:
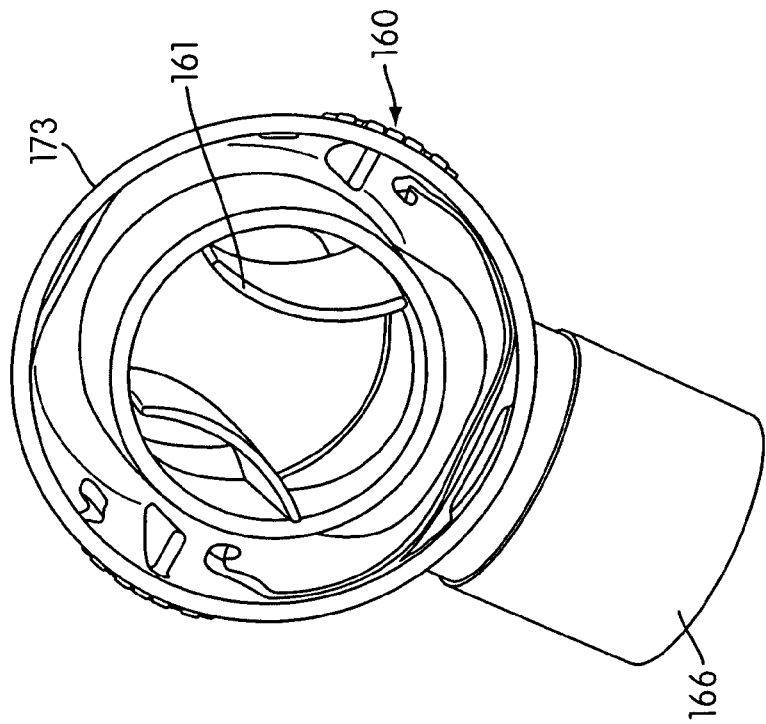
Figure 26A:
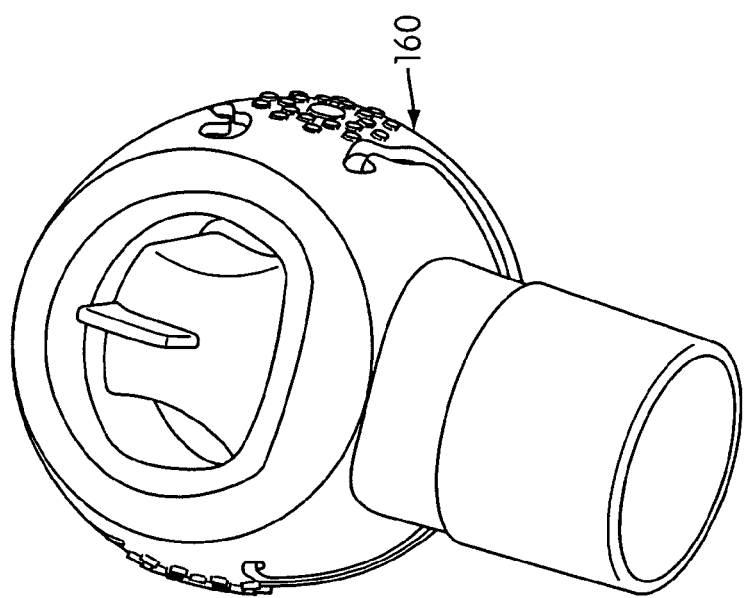
Figure 27A:
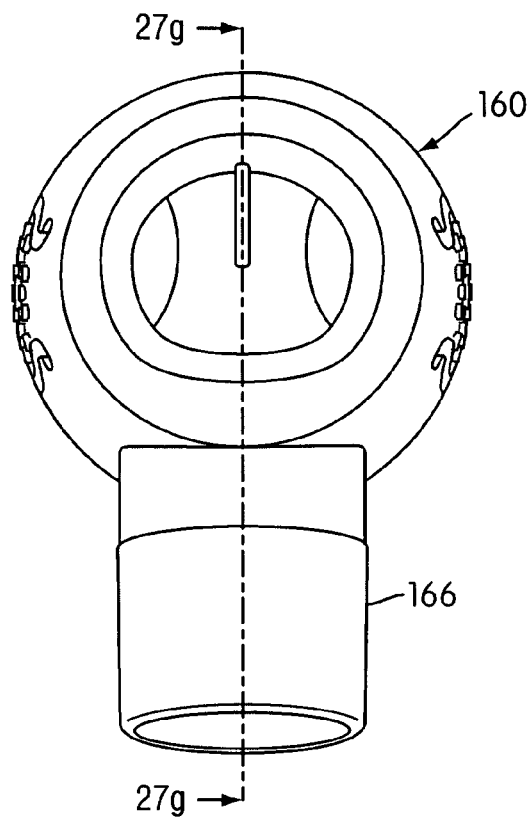
Figure 27B:
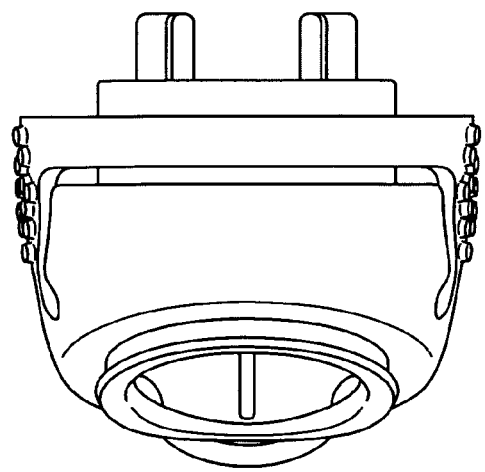
Figure 27C:
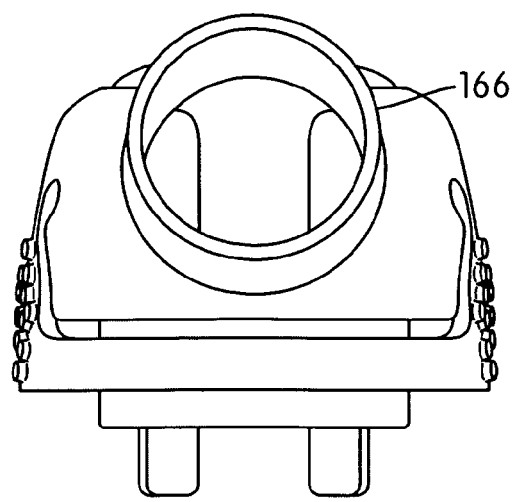
Figure 27D:
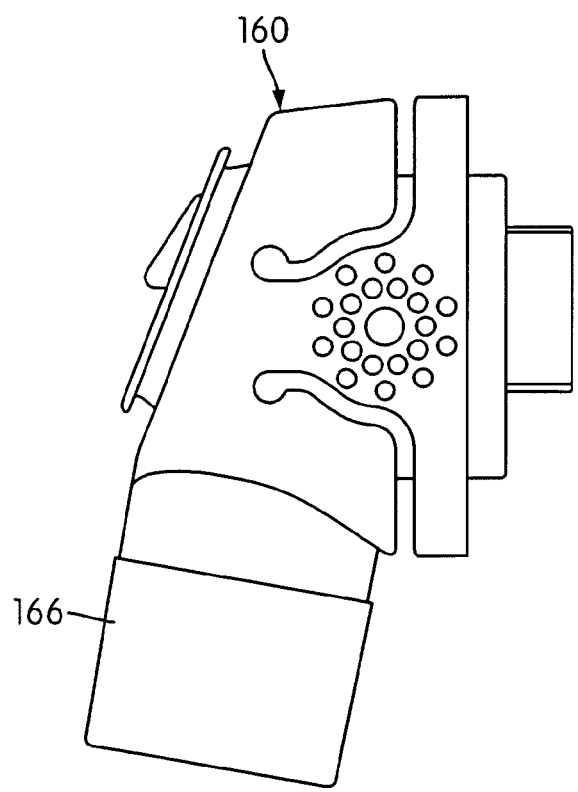
Figure 27E:
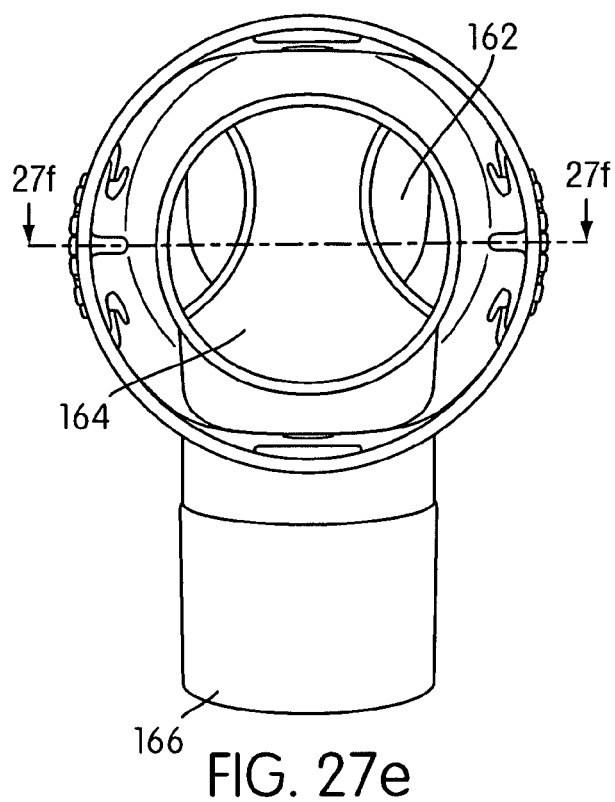
Figure 27F:
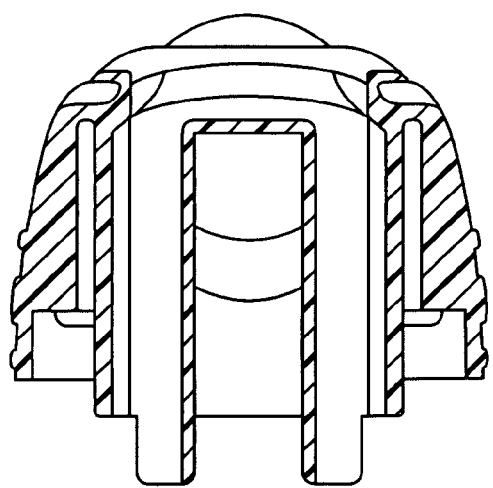
Figure 27G:
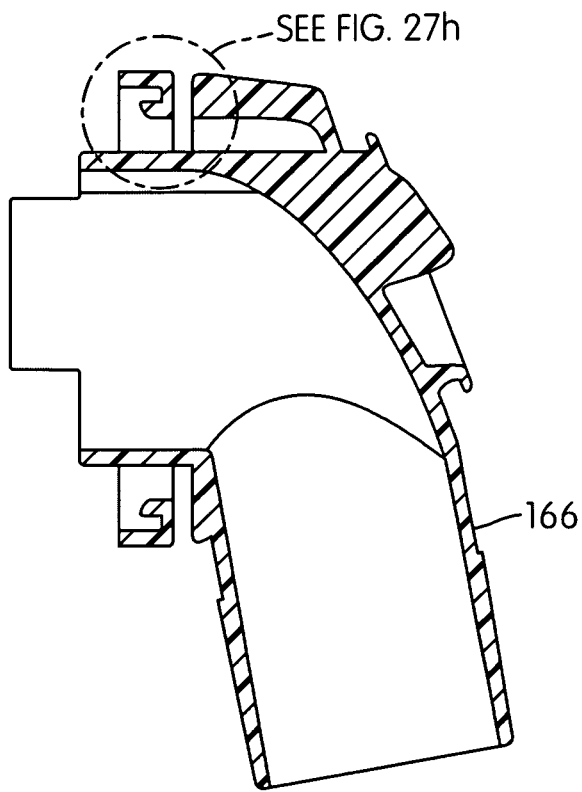
Figure 27H:
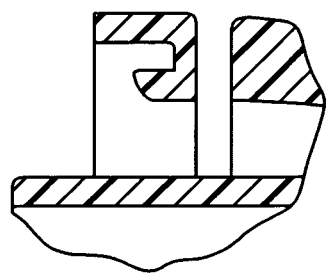
Figure 27J:
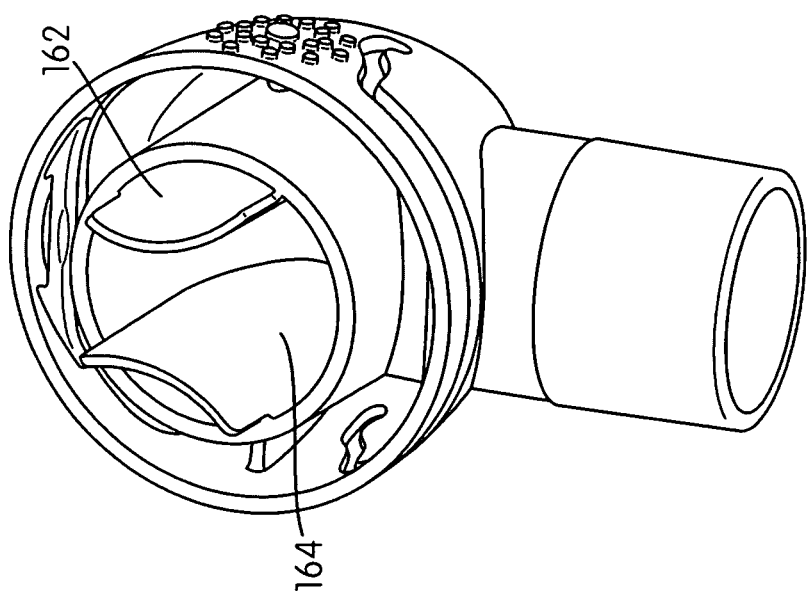
Figure 27I:
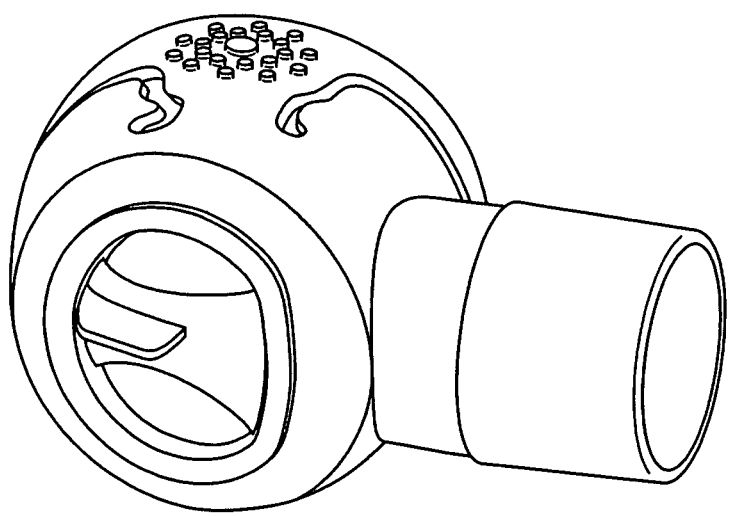
Figure 28B:
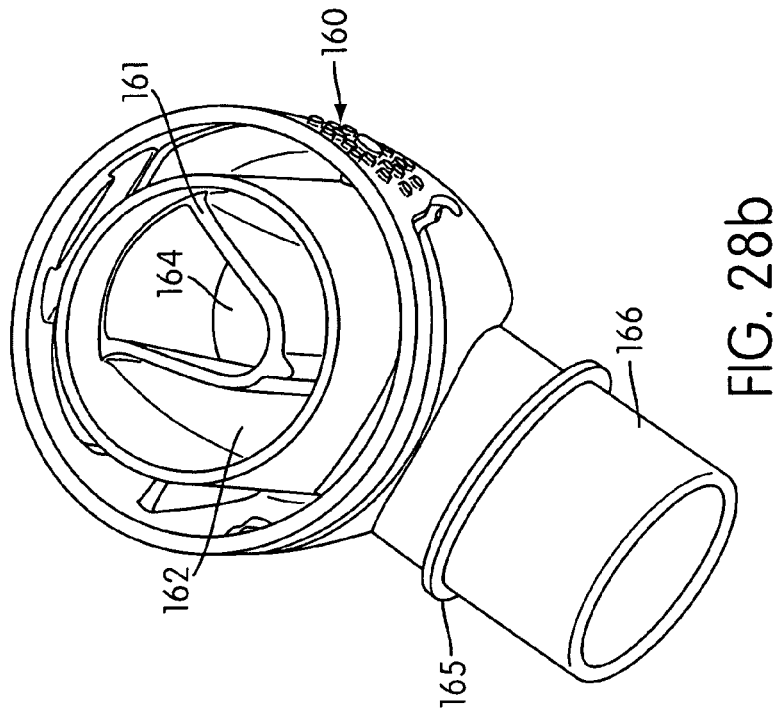
Figure 28A:
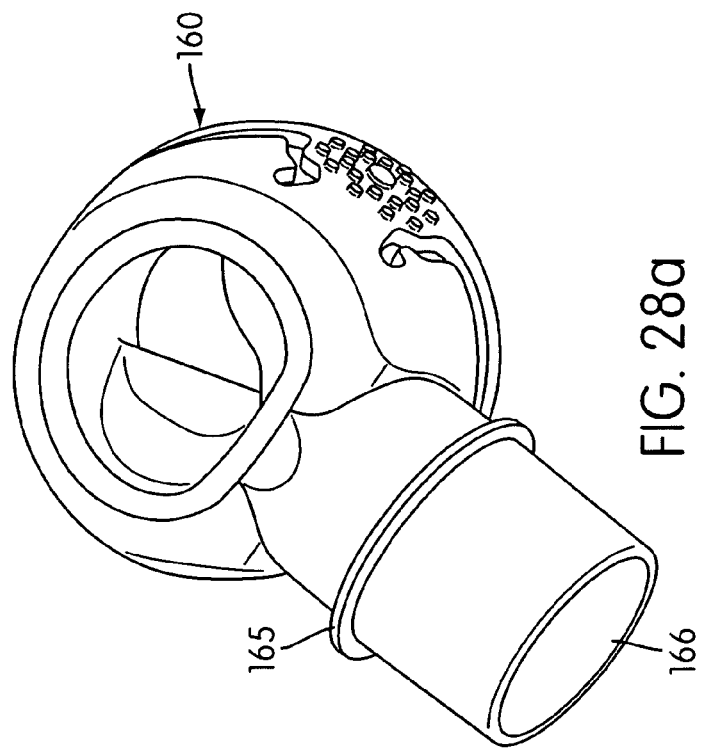
Figure 29A:
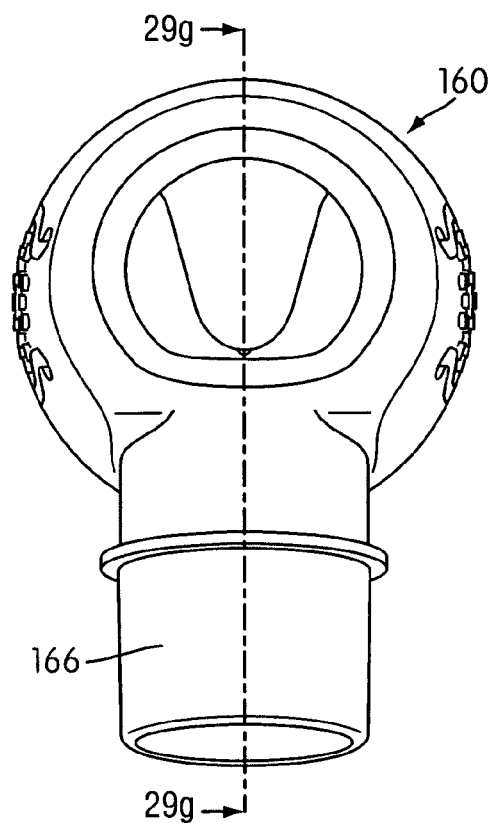
Figure 29B:
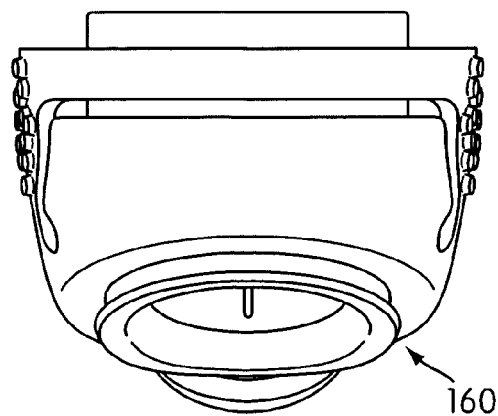
Figure 29C:
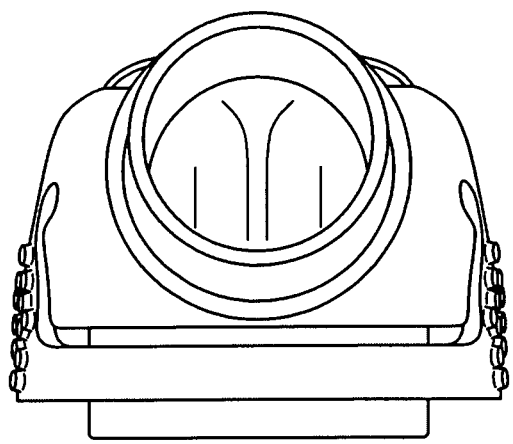
Figure 29D:
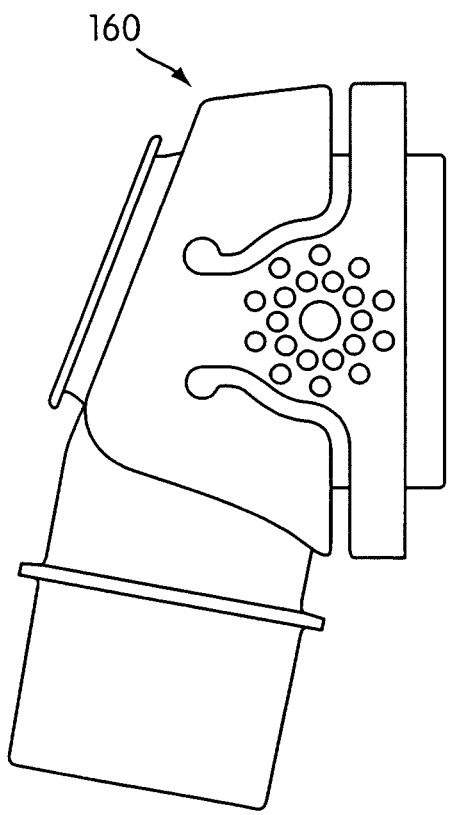
Figure 29E:
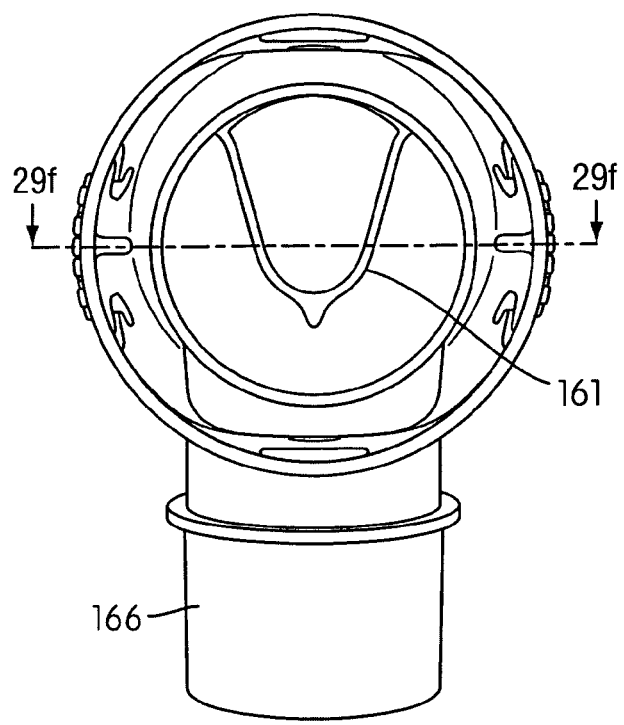
Figure 29F:
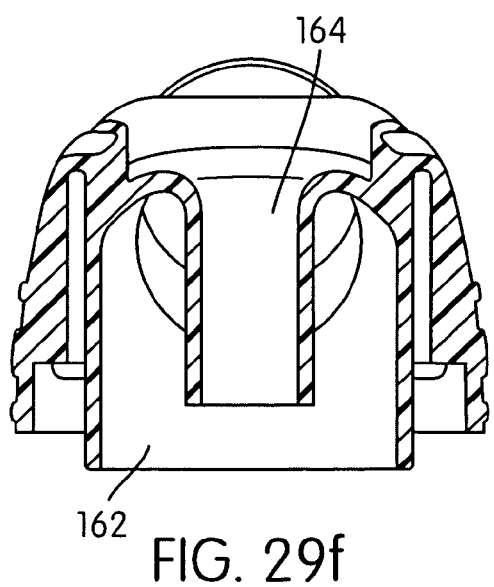
Figure 29G:
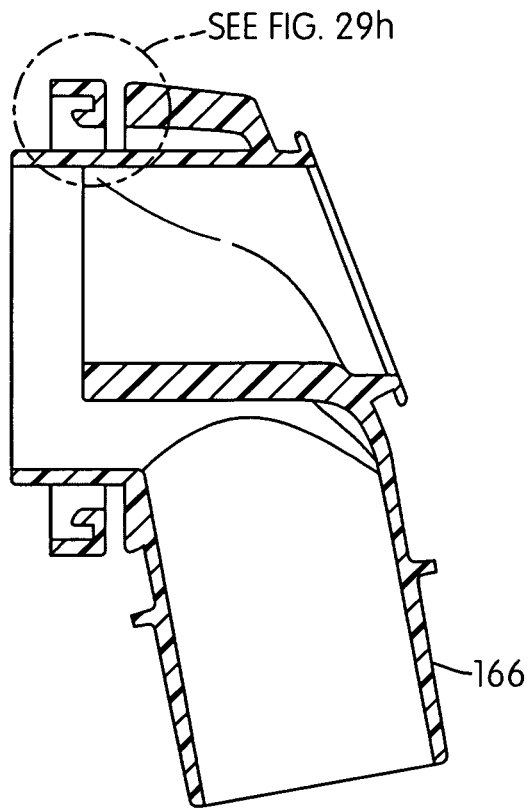
Figure 29H:
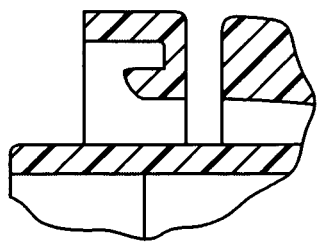
Figure 29J:
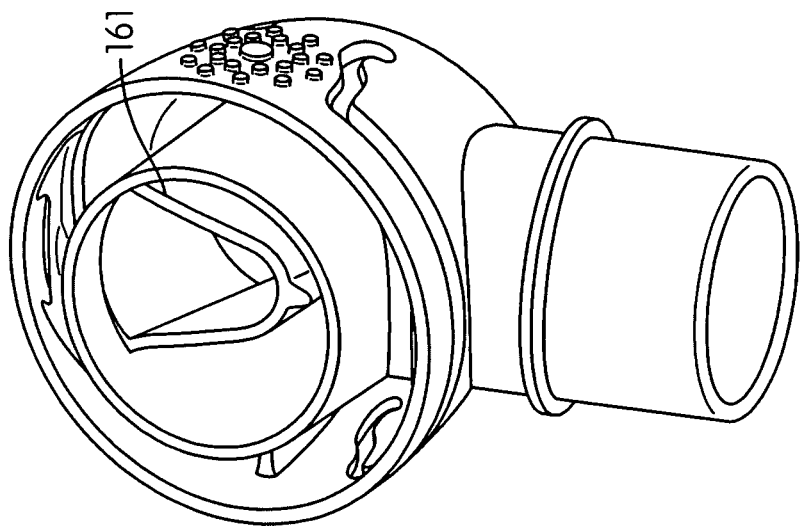
Figure 29I:
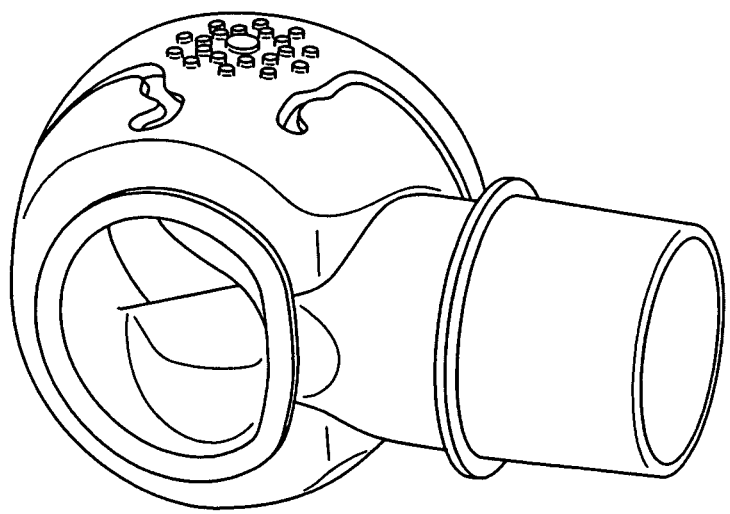
Figure 30A:
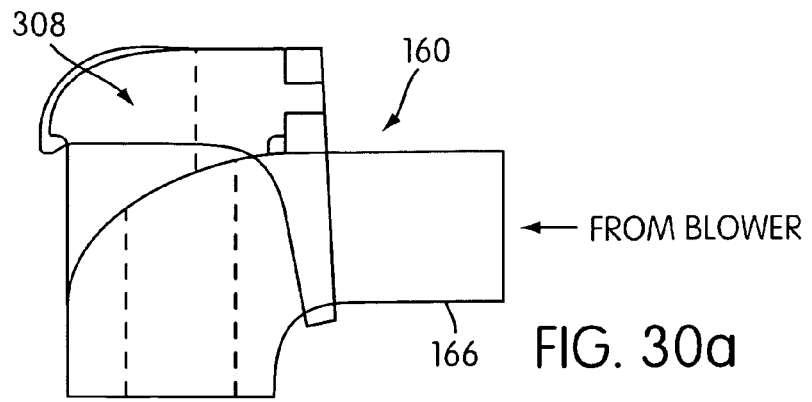
Figure 30B:
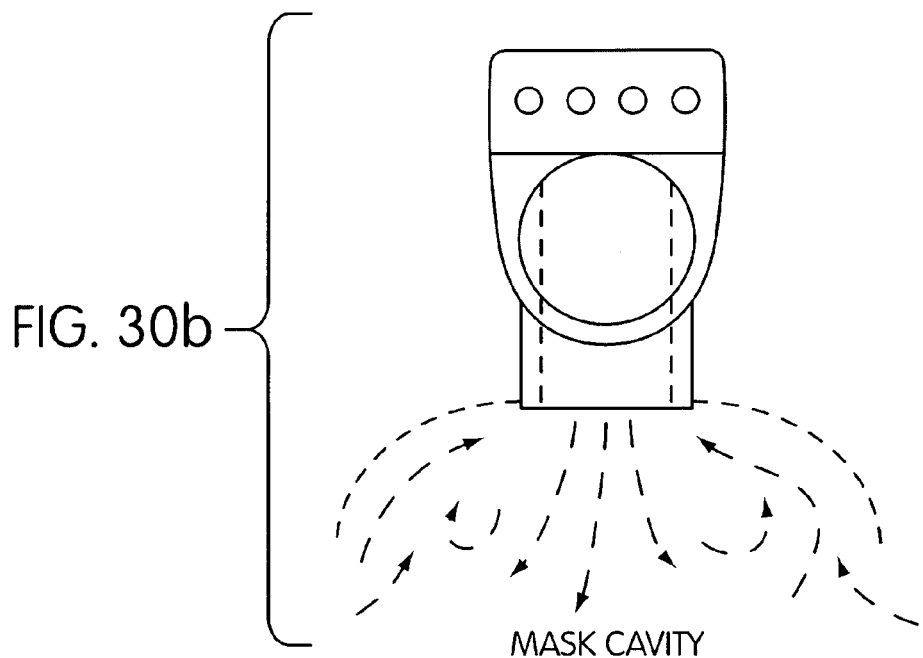
Figure 30C:
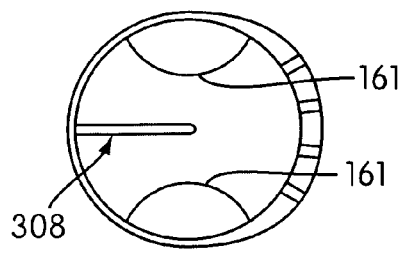

FIG. 27e is a rear view of the swivel elbow shown in FIG. 27a;

FIG. 27f is a cross-sectional view along line 27f-27f of the swivel elbow shown in FIG. 27e;

FIG. 27g is a cross-sectional view along line 27g-27g of the swivel elbow shown in FIG. 27a;

FIG. 27h is a detailed view of a portion of the swivel elbow shown in FIG. 27g;

FIG. 27i is another front perspective view of the swivel elbow shown in FIG. 26a at a slightly different angle;

FIG. 27j is another rear perspective view of the swivel elbow shown in FIG. 26b at a slightly different angle;

FIG. 28a is a front perspective view of a swivel elbow according to another embodiment of the invention;

FIG. 28b is a rear perspective view of the swivel elbow shown in FIG. 28a;

FIG. 29a is a front view of the swivel elbow shown in FIG. 28a;

FIG. 29b is a top view of the swivel elbow shown in FIG. 29a;

FIG. 29c is a bottom view of the swivel elbow shown in FIG. 29a;

FIG. 29d is a right side view of the swivel elbow shown in FIG. 29a;

FIG. 29e is a rear view of the swivel elbow shown in FIG. 29a;

FIG. 29f is a cross-sectional view along line 29f-29f of the swivel elbow shown in FIG. 29e;

FIG. 29g is a cross-sectional view along line 29g-29g of the swivel elbow shown in FIG. 29a;

FIG. 29h is a detailed view of a portion of the swivel elbow shown in FIG. 29g;

FIG. 29i is another front perspective view of the swivel elbow shown in FIG. 28a at a slightly different angle;

FIG. 29j is another rear perspective view of the swivel elbow shown in FIG. 28b at a slightly different angle;

FIG. 30a is a side view of a swivel elbow according to another embodiment of the invention;

FIG. 30b is a right side view of the swivel elbow shown in FIG. 30a;

FIG. 30c is a top view of the swivel elbow shown in FIG. 30a; and

Figure 30D:
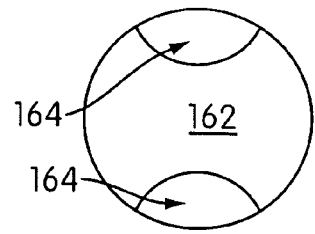

FIG. 30d is a partial bottom view of the swivel elbow shown in FIG. 30a.

DETAILED DESCRIPTION OF ILLUSTRATED EMBODIMENTS

Figure 1:
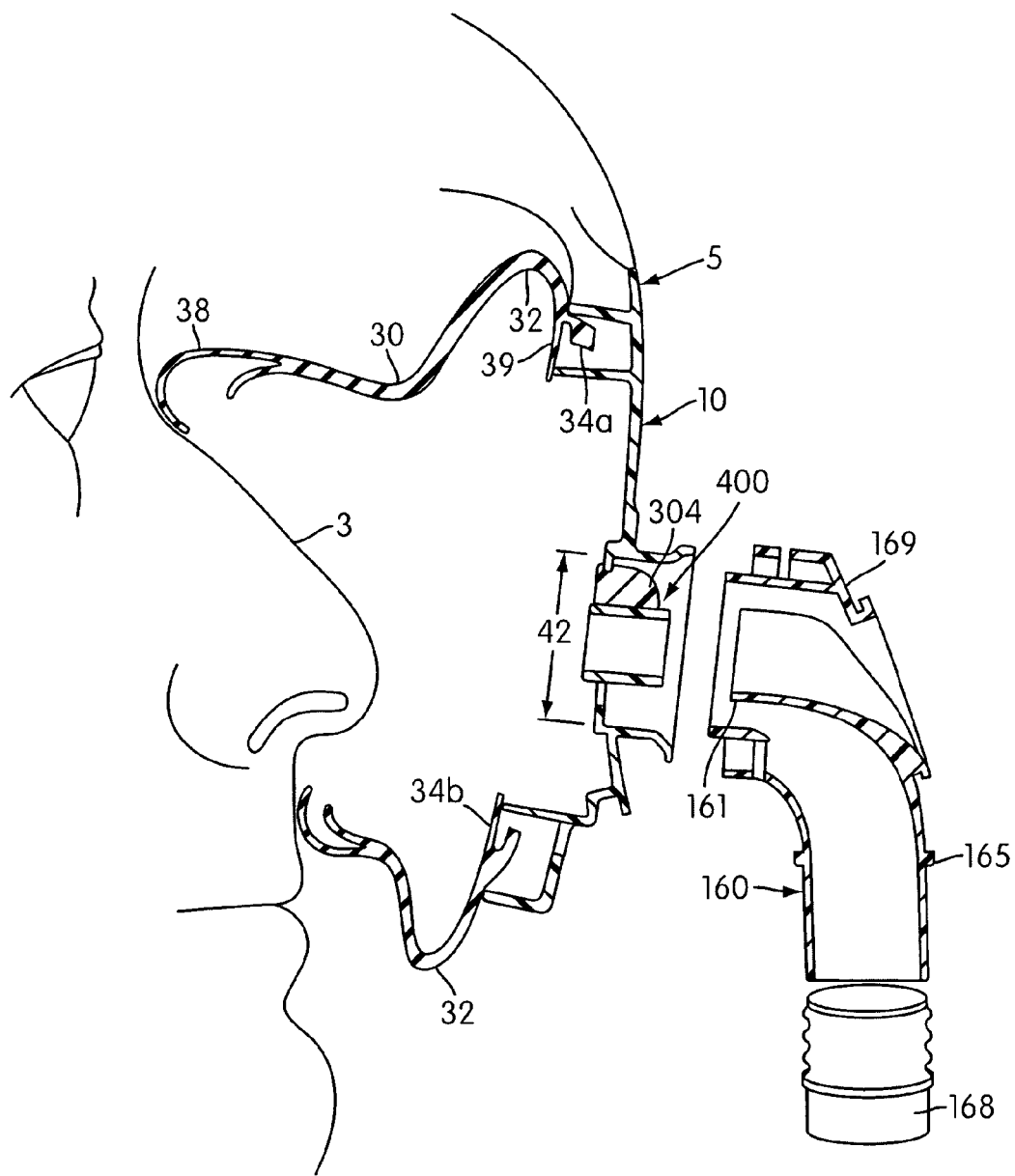
FIG. 1 is an exploded cross-sectional view of a respiratory mask assembly according to one embodiment of the present invention.

FIG. 1 shows an exploded cross-sectional view of a mask assembly 5 according to one embodiment of the present invention. The mask assembly 5 is intended to be worn by a user 1 and substantially surrounds the nose 3 of the user 1. The mask assembly 5 includes, for example, a mask frame 10, a swivel elbow assembly 20 connected to the mask frame 10, and a cushion 30 connected to the mask frame 10. The swivel elbow assembly is adapted to be connected to an air tube 168 that delivers breathable gas to the user 1.

The cushion 30 is designed to substantially surround the user's nose 3 and apply pressure around the cushion's 30 perimeter while minimizing and/or avoiding contact with pressure sensitive regions on the user's face. Some parts of the user's face, for example, the nasal bridge region, require special attention to achieve a balance between pressure and seal. It is also desirable to provide a low profile mask to improve the comfort level of the user 1 by improving stability, and to reduce the forces which may tend to pivot the mask assembly 5 relative to the user's face. While the cushion 30 is shown as being used with a nasal mask assembly, it can also be designed for use with a full face mask or a nasal/oro mask assembly.

The cushion 30 has a face-contacting side 38 and a non face-contacting side 39. The non-face contacting side 39 of the cushion 30 engages the mask frame 10 at points 34a and 34b. Any type of connection system can be used for connecting the cushion 30 to the mask frame 10 in the mask assembly 5. Some examples include interior cushion clips or exterior cushion clips, which are used in ResMed's Ultra Mirage® mask, which is described in U.S. Pat. No. 6,412,487, incorporated in its entirety herein by reference. The cushion 30 can be permanently or detachably and/or reattachably connected to the mask frame 10. Other forms of cushion connection may be used such as friction fits, gluing and tongue and groove mechanisms.

The mask frame 10 includes at least one aperture 42, adapted to fit the elbow assembly 20. The aperture 42 has a diameter in its broadest aspect between about 20 mm to about 40 mm, more preferably a diameter between about 25 mm to about 30 mm, and most preferably a diameter of about 28 mm. The aperture 42 preferably has a generally circular shape. However, the aperture 42 may have a non-circular shape. Further, the mask frame 10 may have a plurality of apertures therethrough with the elbow assembly 20 coupled to the mask frame 10 such that it surrounds the plurality of apertures.

Figure 2:
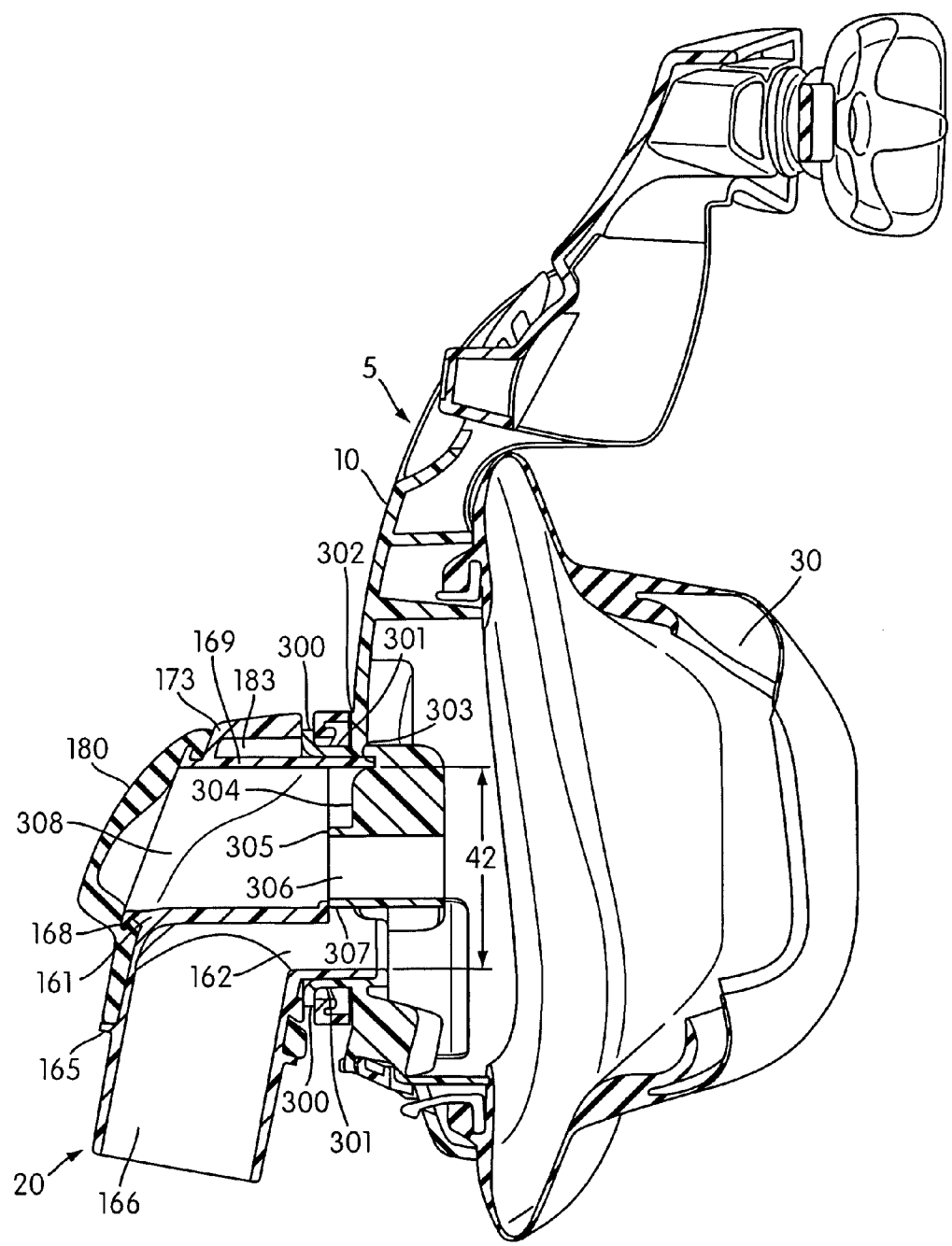
FIG. 2 is an assembled cross-sectional view of the respiratory mask assembly shown in FIG. 1.

FIG. 2 is a cross-sectional view of the mask assembly 5, showing one embodiment of the mask frame 10, one embodiment of the cushion 30, and one embodiment of the elbow assembly 20, connected together according to one embodiment of the present invention. FIG. 2 also shows a vent cover 180 attached to the swivel elbow 160. The vent cover 180 directs exhaust air along the air tube therefore avoiding disturbance of a bed partner and minimizing noise.

Figure 3A:
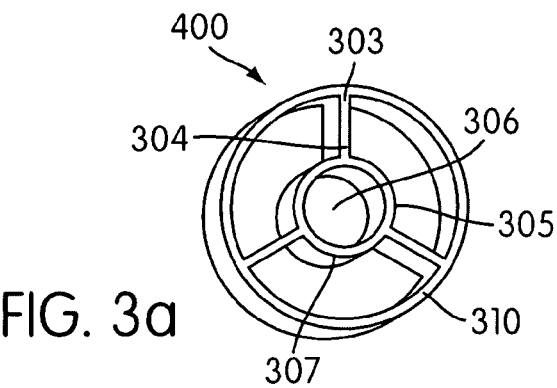
FIG. 3a is a perspective view of a ring according to one embodiment of the present invention.

The aperture 42 may optionally include a ring 400. FIG. 3a is a perspective view of the ring 400. Ring 400 includes an outer ring 310 and an inner ring 307 defining a passage 306 which directs exhaust through the vent cover 180, e.g., via a vent cavity 308. The outer ring 310 is attached to the inner ring 307 by at least one connecting arm 304. In the embodiment show in FIG. 3a, ring 400 has three connecting arms 304. It would be evident to a person skilled in the art that different numbers of connecting arms 304 can be used.

In one embodiment, the ring 400 is fabricated as one piece with the mask frame 10. In this embodiment, the inner diameter of the aperture 42 is co-incident with the outer ring 310 (i.e., the outer ring 310 is the inner diameter of the aperture 42). In another embodiment, the ring 400 is fabricated separately and adapted to be detachable engaged with the mask frame 10.

Each connecting arm 304 can be essentially straight or can include depressions, notches, and/or projections. In the embodiment shown in FIG. 3a, the connecting arm 304 includes one notch 303 and a projection 305. The profile of the ring 400 is shown in FIG. 3b.

Figure 3B:
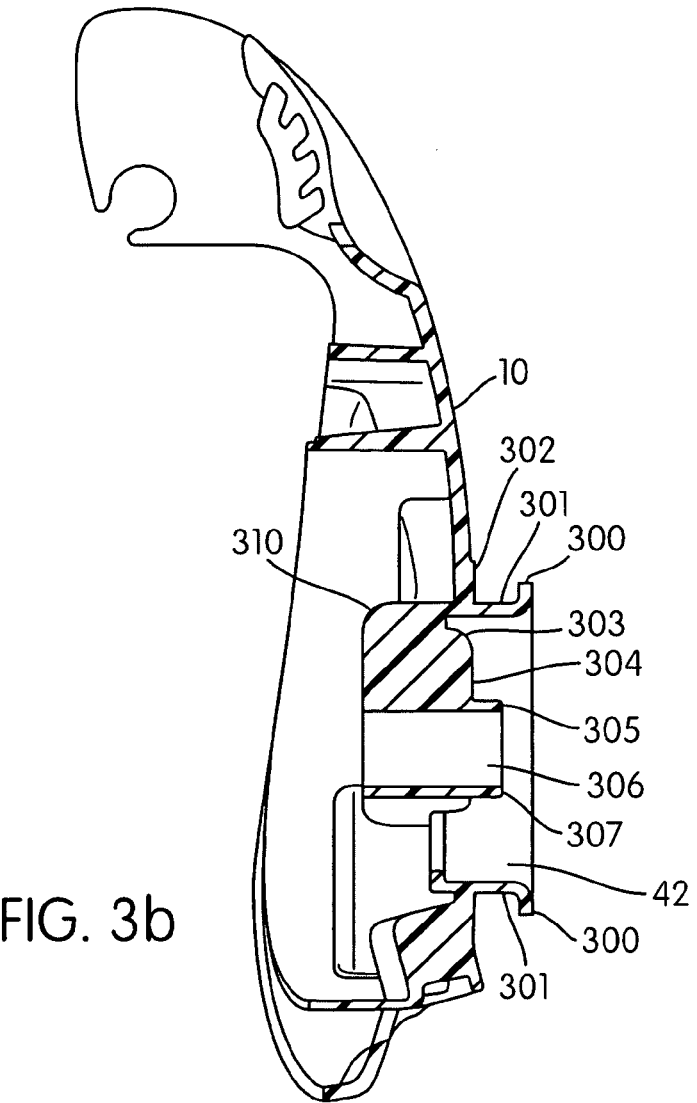
FIG. 3b is a cross-sectional view of a frame portion of the respiratory mask assembly shown in FIG. 2.

FIG. 3b is a cross-sectional view of the area surrounding the aperture 42 in the mask frame 10. The aperture 42 is surrounded by a flange 301 and a lip 300. The mask frame 10 in this embodiment also includes a bump 302. The flange 301, lip 300, and bump 302 are adapted to engage the elbow assembly 20.

In the embodiment shown in FIG. 3b, the outer ring 310 of the ring 400 is integrated with the flange 301. This causes a through channel defined by the aperture 42 in the mask frame 10 and the passage 306 in the ring 400. The outer ring 310 has a diameter in its broadest aspect between about 20 mm to about 40 mm, more preferably a diameter between about 25 mm to about 30 mm, and most preferably a diameter about 24 mm. The passage 306 has a diameter in its broadest aspect between about 4 mm to about 12 mm, more preferably a diameter between about 6 mm to about 10 mm, and most preferably a diameter about 8 mm.

Figure 4A:
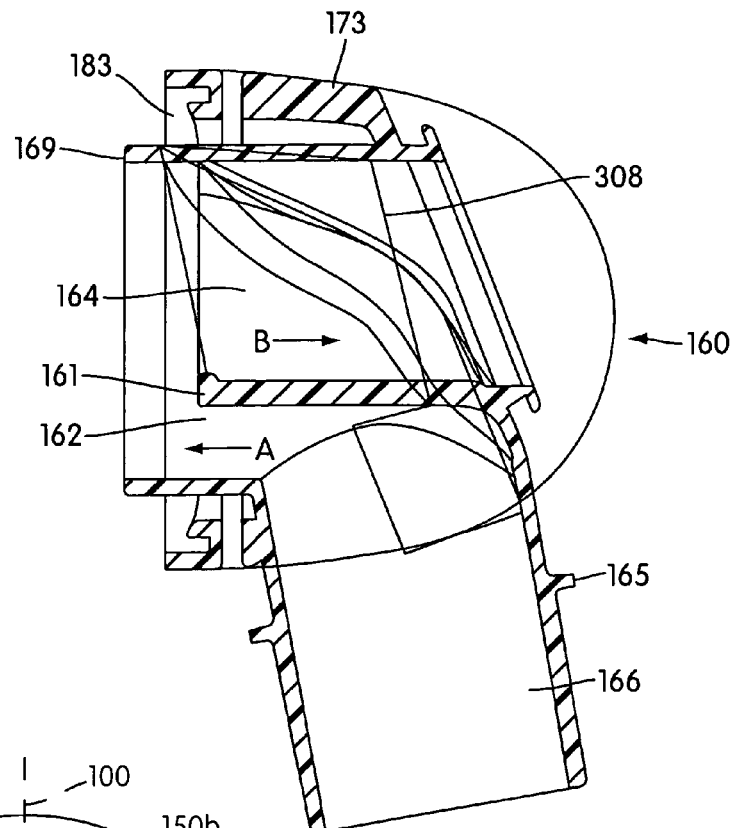
FIG. 4a is a cross-sectional view of one embodiment of the swivel elbow according to the present invention.
Figure 4B:
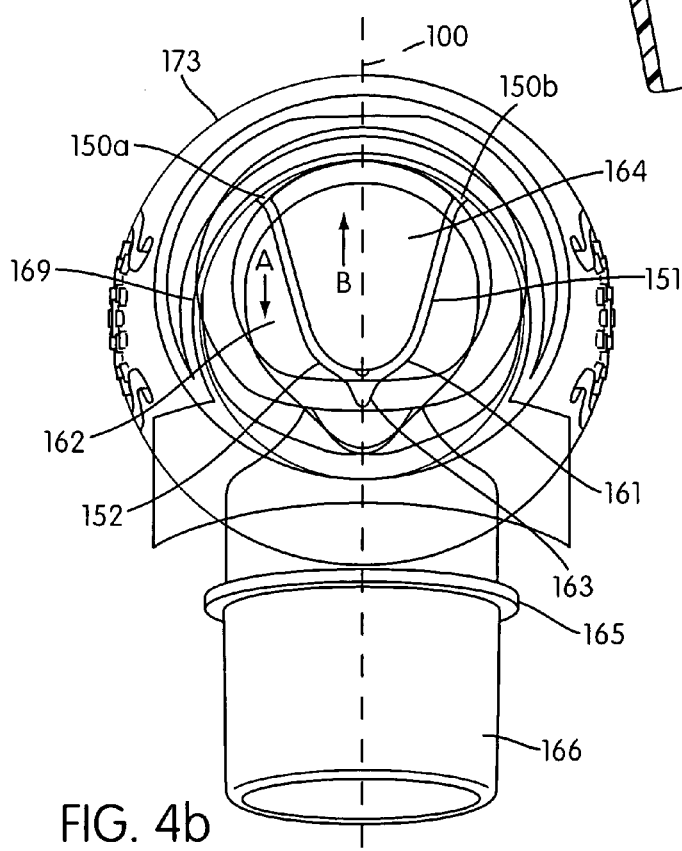

FIGS. 4a and 4b show one embodiment of a swivel elbow 160 in greater detail. The swivel elbow 160 is rotationally connected to the mask frame 10 and includes a stem 166 which is adapted to receive the air tube 168 to supply pressurized breathable air or gas from a blower (not shown). In the embodiment shown, the stem 166 includes an element 165. A top of element 165 is adapted to engage a bottom of the vent cover 180.

FIG. 4a is a cross-sectional view of one embodiment of the swivel elbow 160. It shows that the swivel elbow 160 includes a collar 173 that surrounds the end portion 169 of the elbow 160. The end portion 169 of the elbow 160 extends beyond the collar 173 to improve alignment when assembled into the mask frame 10. In particular, the end portion 169 is adapted to engage notch 303 in the ring 400 (if used). The collar 173 is spaced away from the end portion 169 in concentric relation so as to form a receiving space 183 between the collar 173 and the end portion 169. Collar 173 is adapted to engage bump 302 when the swivel elbow assembly 20 is attached to the mask frame 10. One example of a detachable swivel elbow connection is described in U.S. Patent Application No. 60/402,509, filed Aug. 12, 2002, the contents of which are incorporated in their entirety by reference herein.

In order to improve $CO_2$ washout in a mask assembly 5, especially with a large breathing cavity 35 such as a full-face mask or a cushion with gusset, a baffle 161 to separate inlet port 162 from the exhaust port 164 has been developed. The exhaust cavity 308 is shown in FIG. 4a as well. The exhaust cavity 308 directs gas washout to the vent cover 180, which is not shown in FIG. 4a. The depth of the baffle 161 is one design parameter that has been manipulated to improve $CO_2$ washout. A number of different forms of the elbow 160 and the mask frame 10 can be produced to create the desired baffle depth. In one embodiment of the invention, the mask frame 10 does not form the baffle 161, but the whole baffle depth is formed by the elbow 160. In another embodiment, the ring 400 increases the depth of the baffle 161, which also improves $CO_2$ washout in mask assemblies 5 with large breathing cavities 35.

The swivel elbow 160 includes an intake port 162 and an exhaust port 164. The exhaust port 164 is separated from the intake port 162 by the baffle 161 provided within the interior portion of the elbow 160, as shown in FIGS. 4a and 4b. The orientation of the intake 162 and exhaust 164 ports is selected such that the incoming gas, indicated by the directional arrow A in the intake port 162, less directly impacts the flow of gas washout indicated by the directional arrow B, along the exhaust port 164. Further, the air/gas entering the elbow 160 is less likely to flow directly into the exhaust port 164 since the baffle 161 forces the incoming air to take a tortuous path, e.g., turn around about 180.degree., before being able to exit through the exhaust port 164. As shown in FIG. 4*a*, for example, the baffle 161 and the inlet portion 162 may be non-cocentric.

Figure 4C:
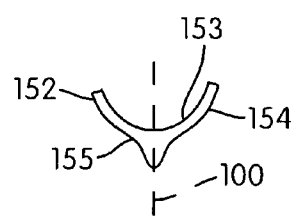
FIG. 4c is a detailed cross-sectional view of the lower portion of the baffle shown in the swivel elbow of FIG. 4b.

The baffle 161 is generally curved. FIG. 4*b* shows the baffle 161 according to one embodiment of the present invention. The baffle 161 is generally sinusoidally-shaped and disposed about a center line 100 in a generally symmetric manner. The baffle 161 includes two points 150*a* and 150*b* of attachment to the end portion 169, a central portion 152, and a bottom 155. The center line 100 intersects the bottom 155 of the baffle 161. The baffle 161 has an inner surface 153 and an outer surface 154, shown in greater detail in FIG. 4*c*.

The baffle 161 includes at least one protrusion 163 that extends from the outer surface 154. The baffle 161 is disposed in a manner such that when the elbow assembly 20 is engaged with the mask frame 10, the inner ring 305 of the ring 400 is situated such that the inner surface 153 is in close proximity with the inner ring 305.

The shape of the baffle 161 has several advantages, some of which are: (i) the incoming gas/air supply in the inlet port 162 is directed by the bottom 155 and/or the protrusion 163, which provides a more even flow to the user 1; (ii) the bottom 155 is generally situated under the user's nostrils such that the exhaust air (rich in $CO_2$) vented out the exhaust port 164 efficiently; and/or (iii) the noise produced by the user 1 is reduced.

Figure 4E:
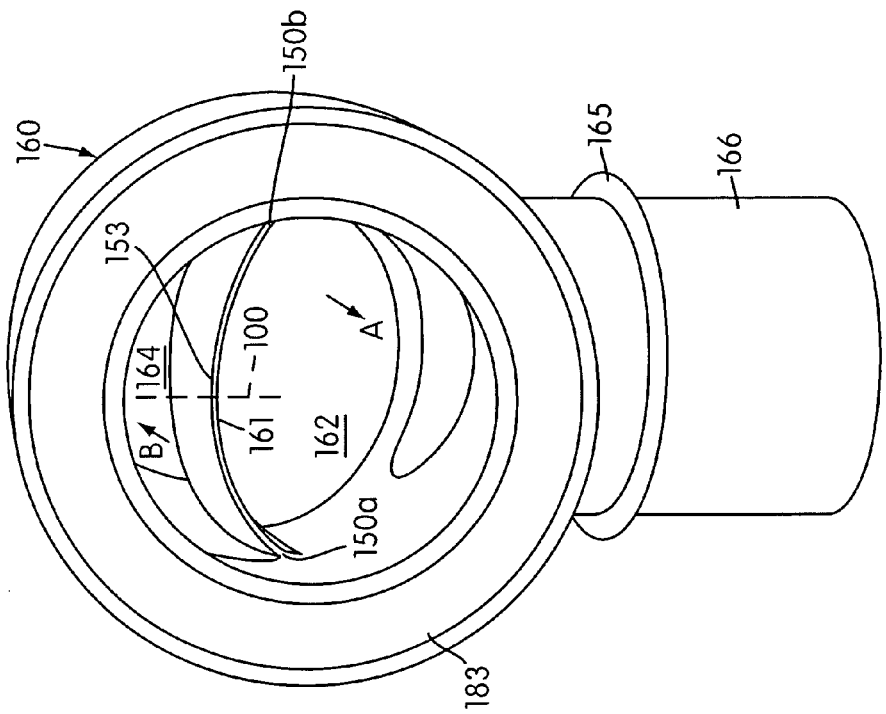
FIG. 4e is a perspective view of a swivel elbow according to another embodiment of the present invention.
Figure 4D:
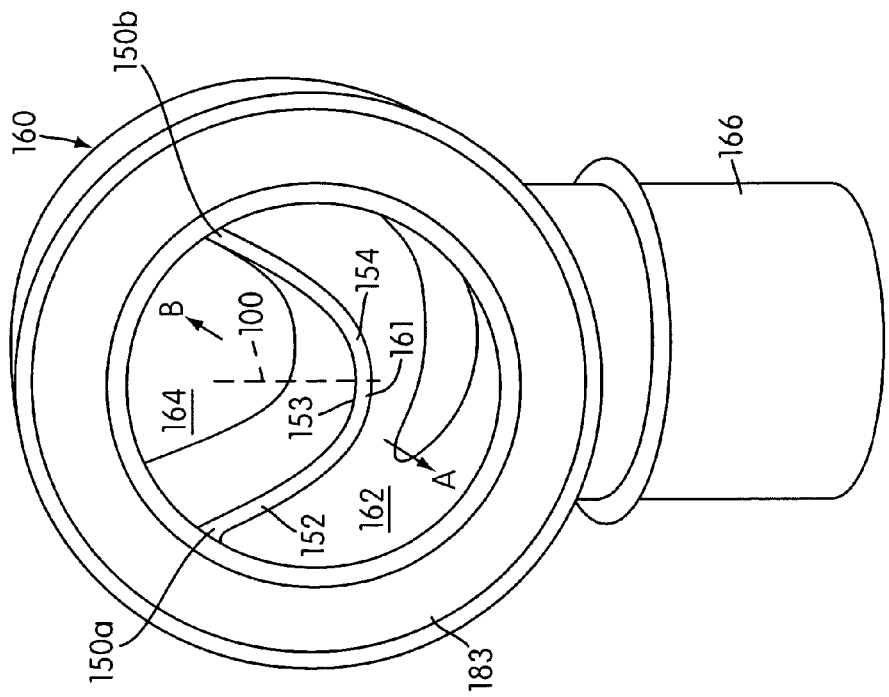
FIG. 4d is a perspective view of a swivel elbow according to another embodiment of the present invention.
Figure 5A:
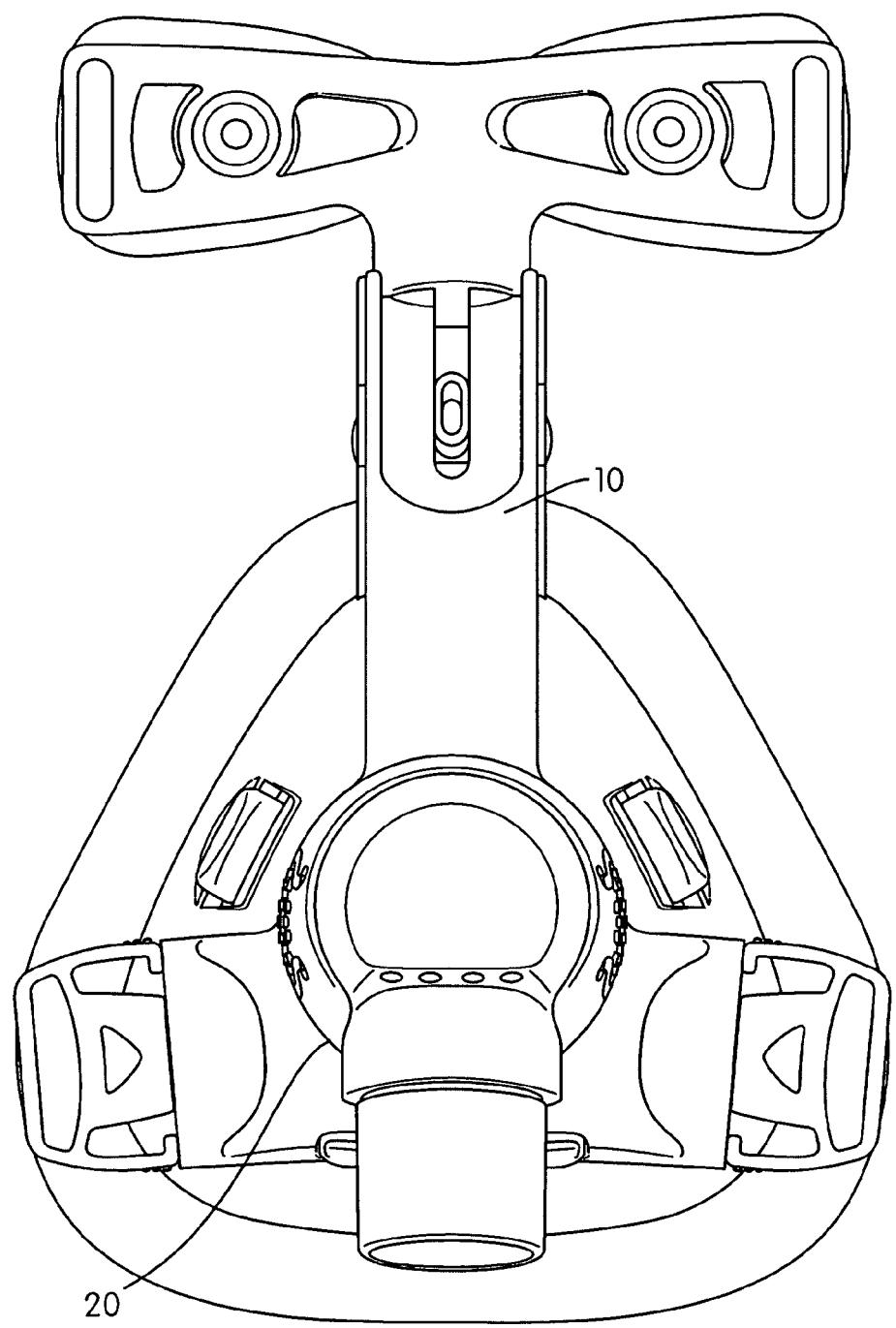
FIG. 5a is a front view of the respiratory mask assembly shown in FIG. 2.
Figure 5B:
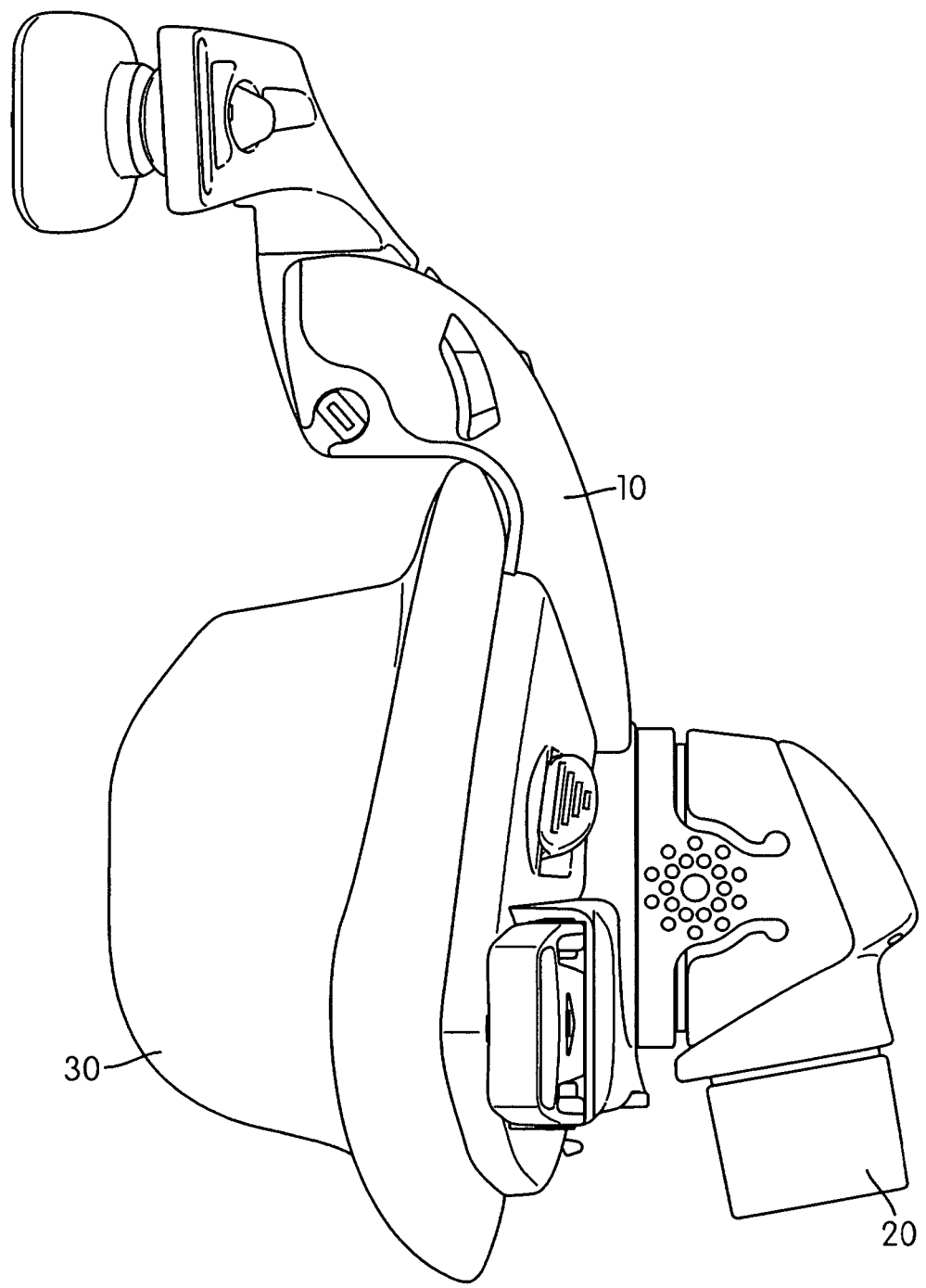
Figure 5C:
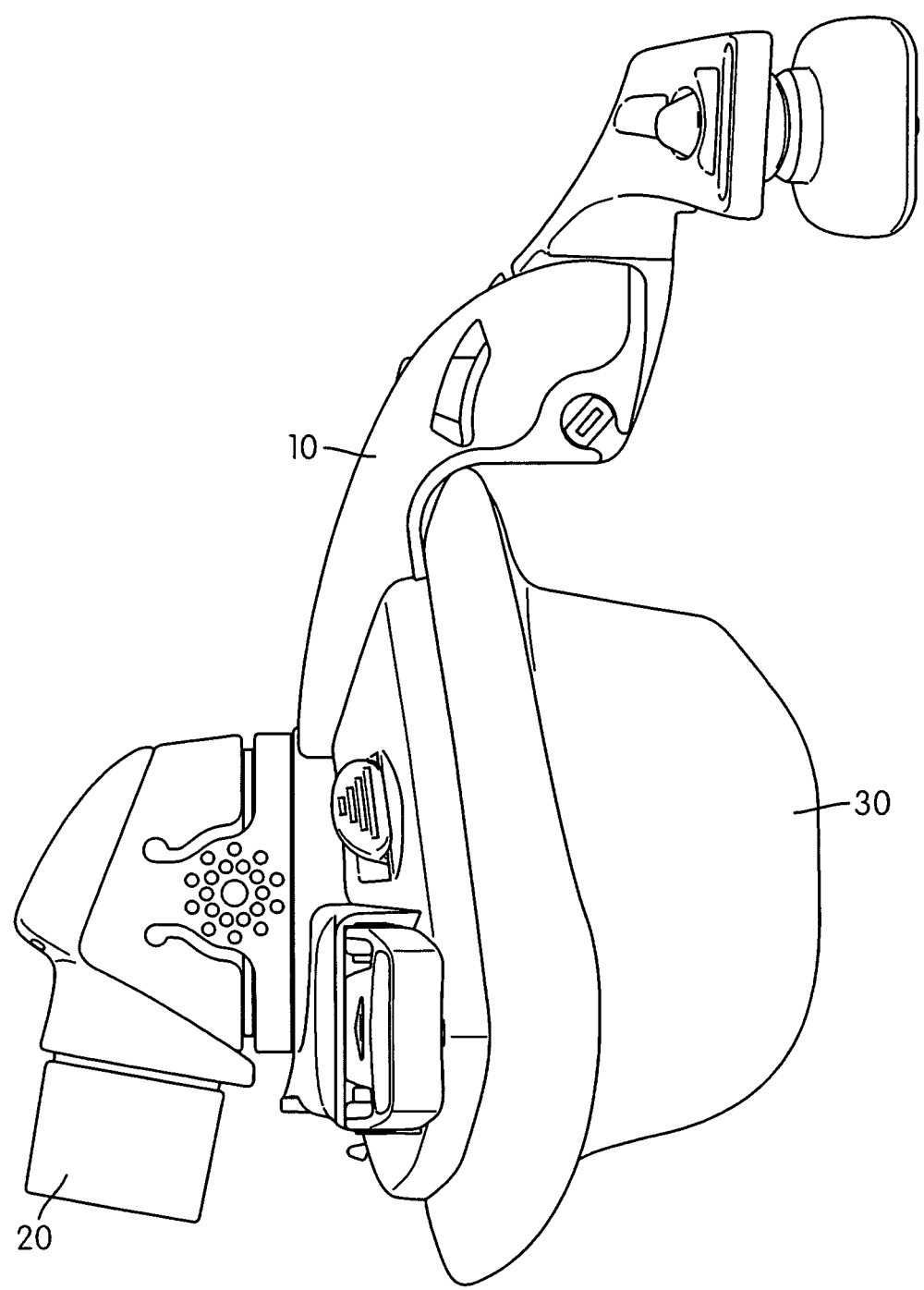
Figure 5D:
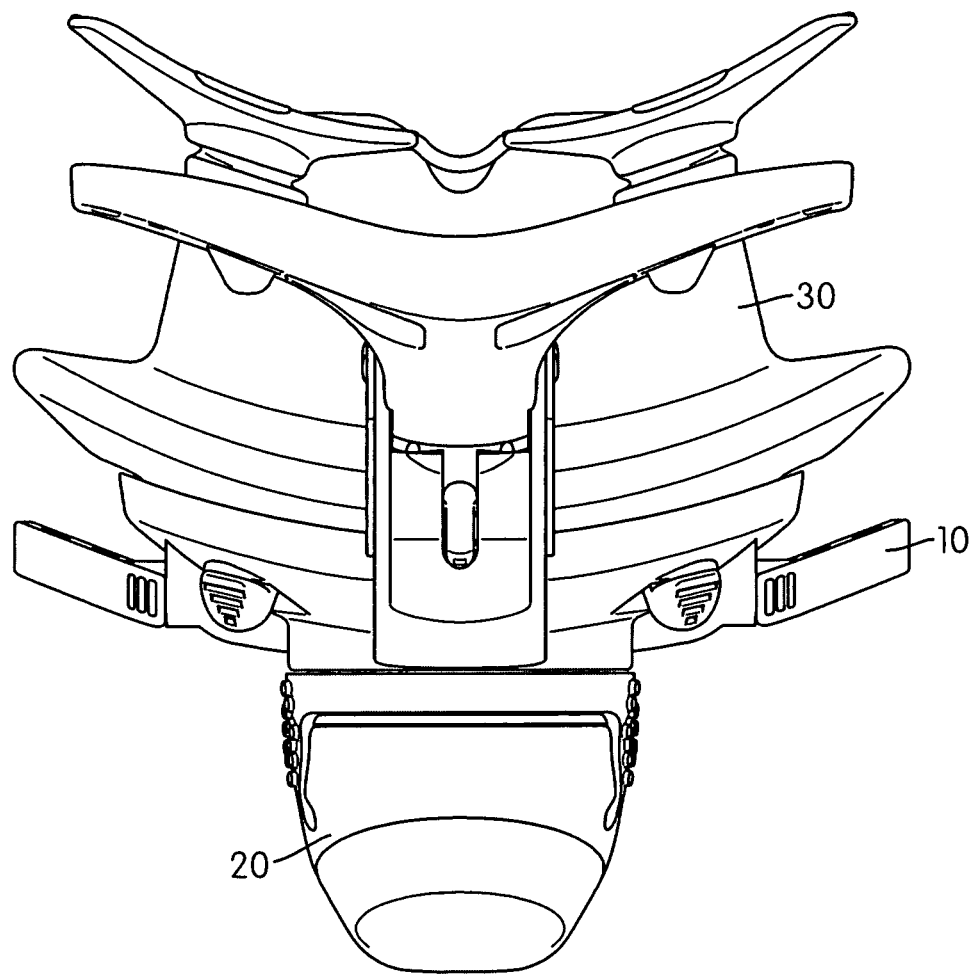
Figure 6B:
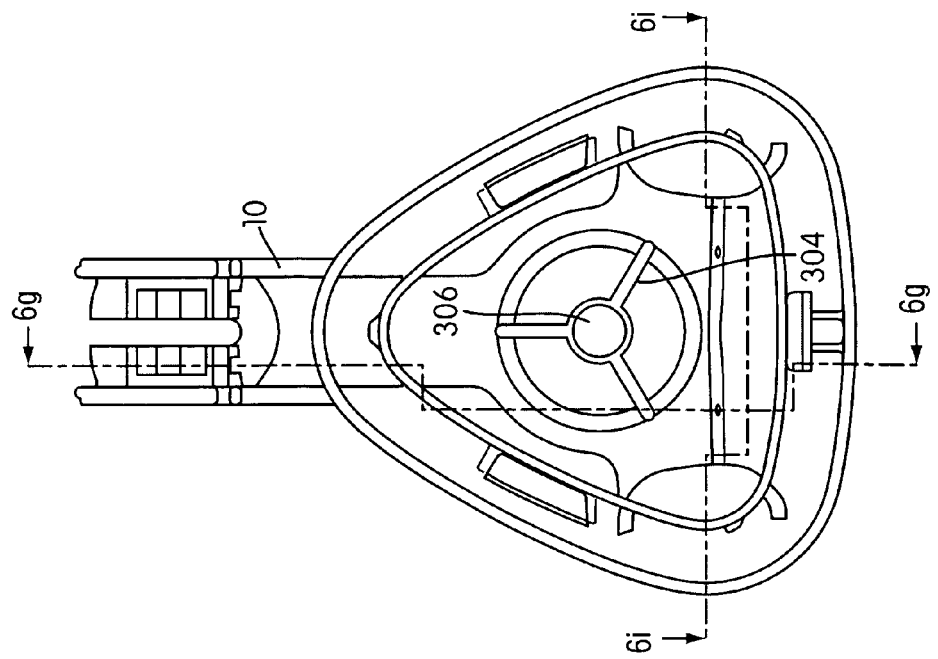
Figure 6A:
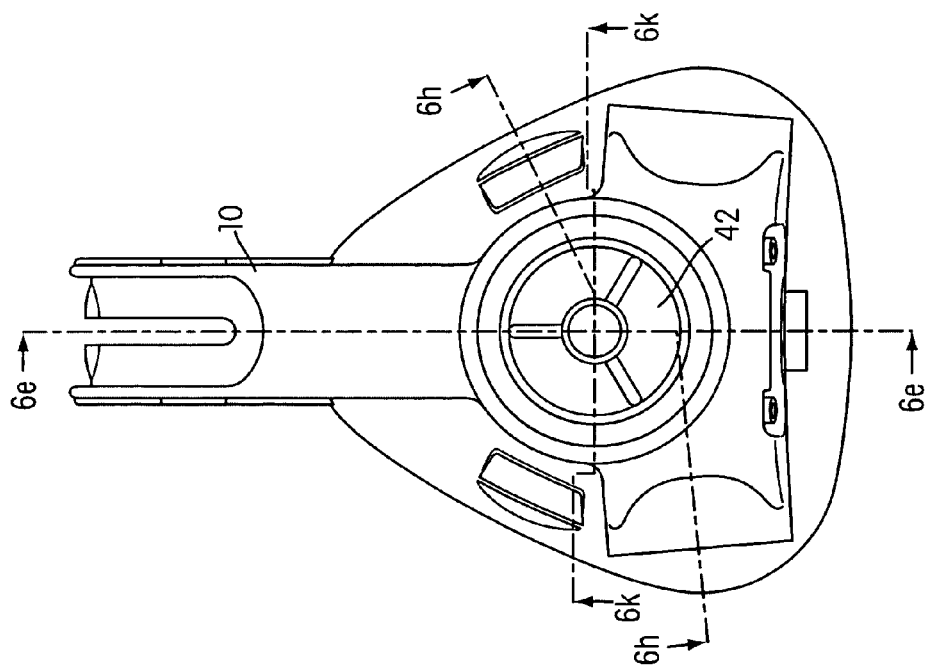
Figure 6D:
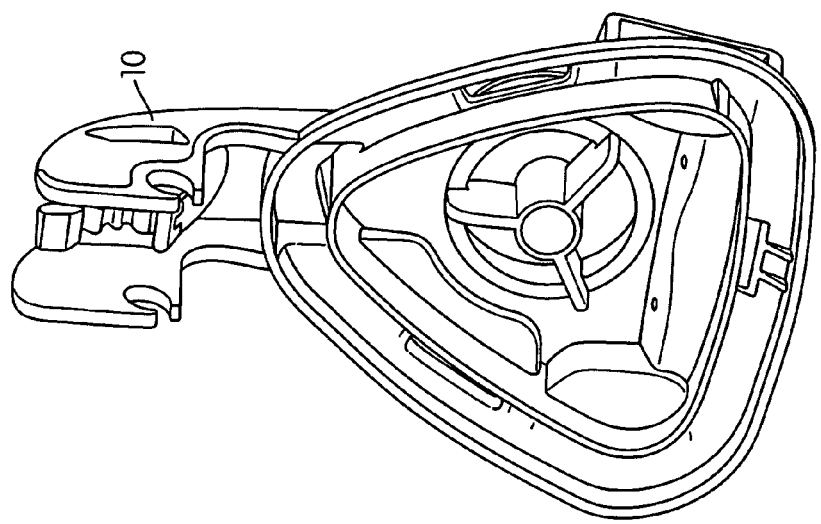
Figure 6C:
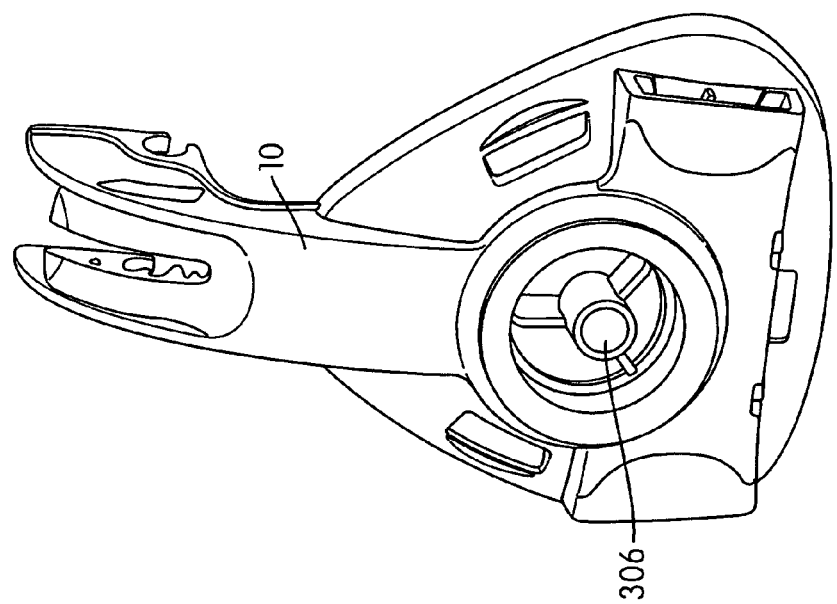
Figure 6G:
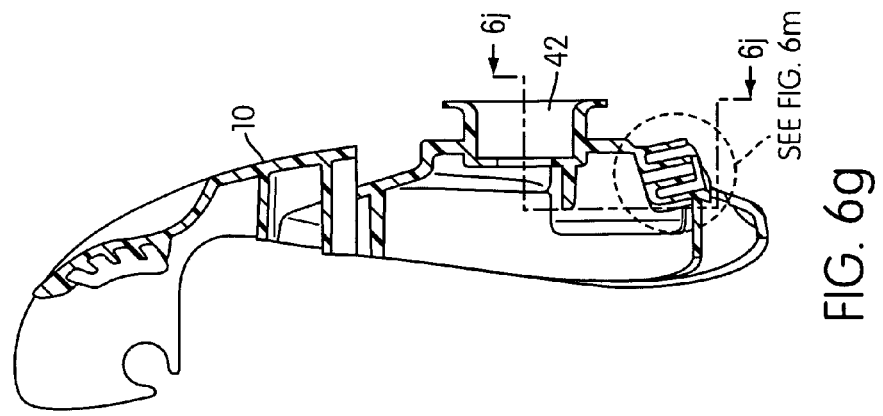
FIG. 6g is a cross-sectional view along line 6g-6g of the respiratory mask frame shown in FIG. 6b.
Figure 6F:
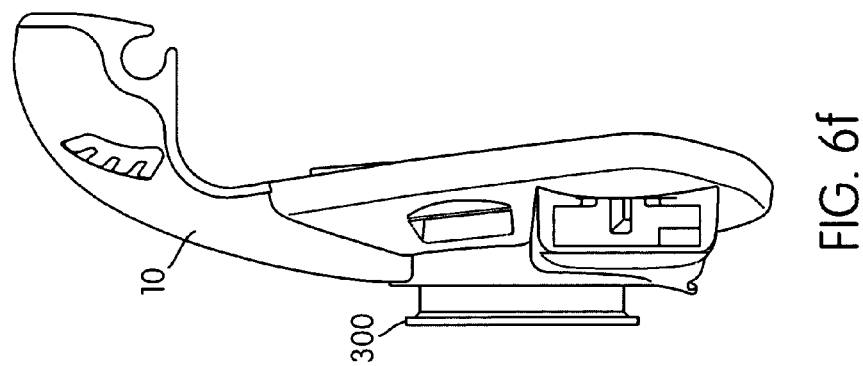
Figure 6E:
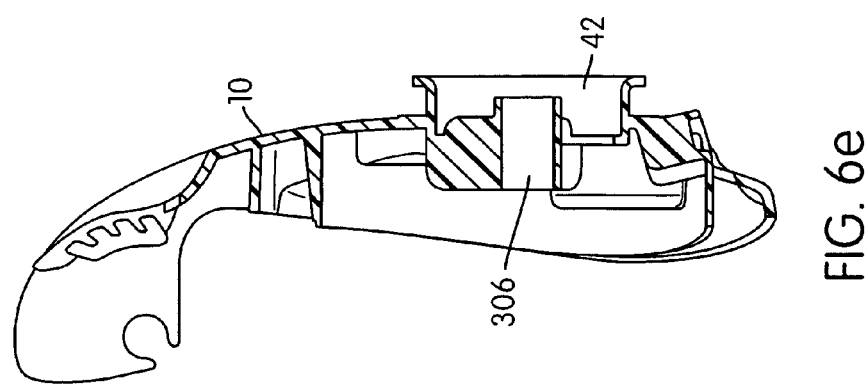
Figure 6H:
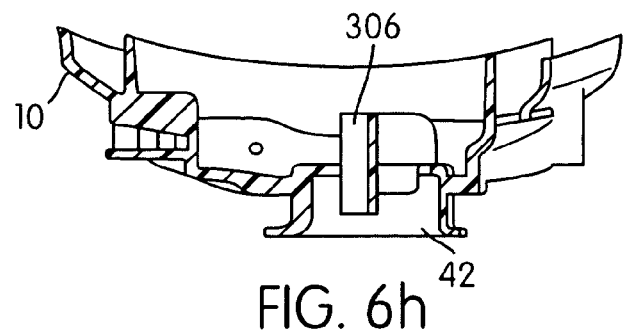
Figure 6I:
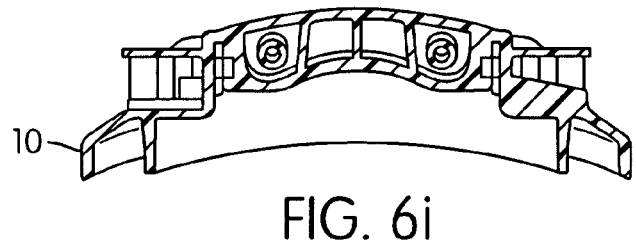
FIG. 6*i* is a cross-sectional view along line 6*i*-6*i* of the respiratory mask frame shown in FIG. 6*b*.
Figure 6J:
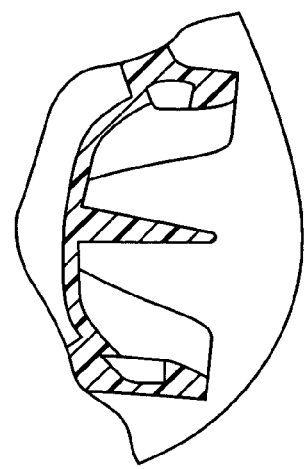
FIG. 6*j* is a cross-sectional view along line 6*j*-6*j* of the respiratory mask frame shown in FIG. 6*g*.
Figure 6K:
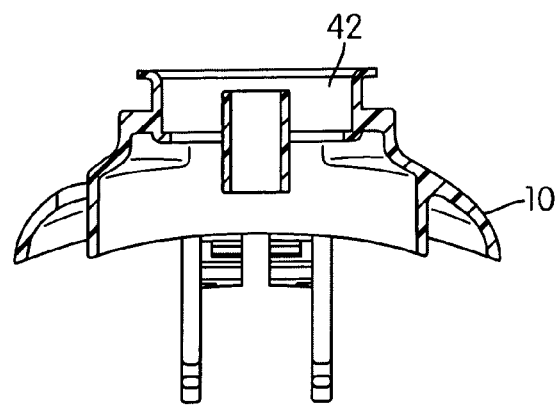
FIG. 6*k* is a cross-sectional view along line 6*k*-6*k* of the respiratory mask frame shown in FIG. 6*a*.
Figure 6L:
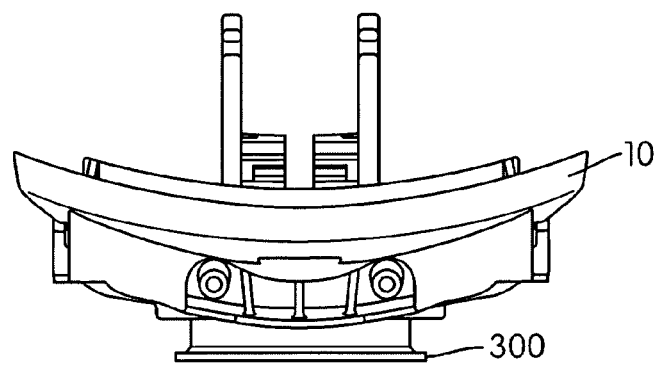
FIG. 6*l* is a bottom view of the respiratory mask frame shown in FIG. 6*b*.
Figure 6M:
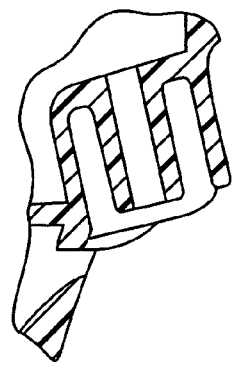
FIG. 6*m* is a detailed cross-sectional view of an exhaust port according to the embodiment of the respiratory mask frame shown in FIG. 6*g*.
Figure 7B:
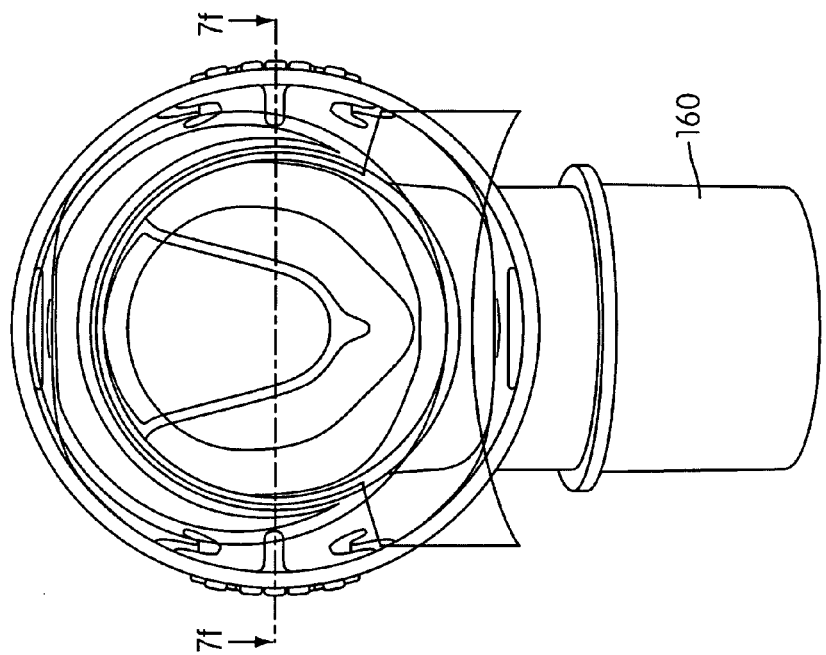
FIG. 7*b* is an alternative front view of the swivel elbow shown in FIG. 7*a*.
Figure 7A:
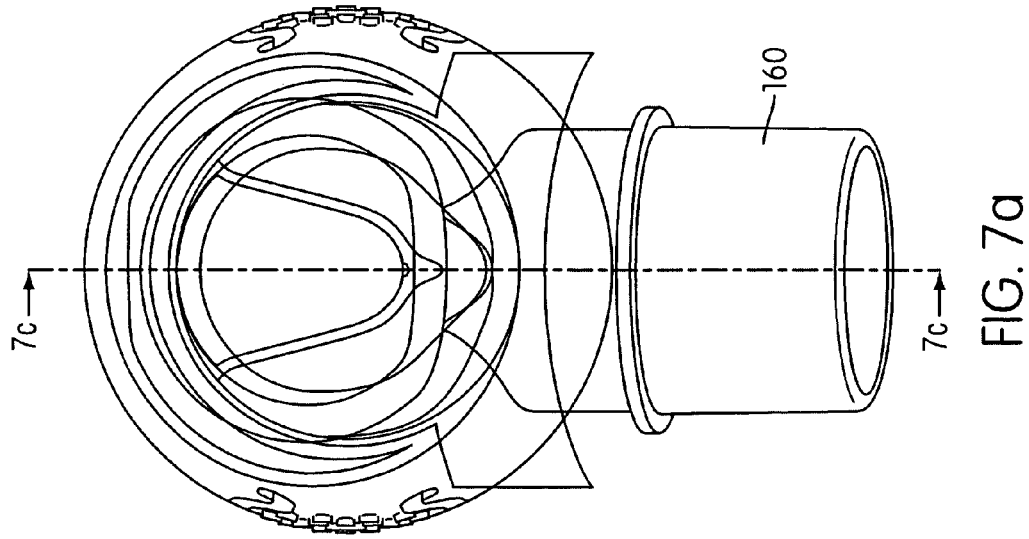
FIG. 7*a* is a front view of the front of the swivel elbow shown in FIG. 4*a*.
Figure 7D:
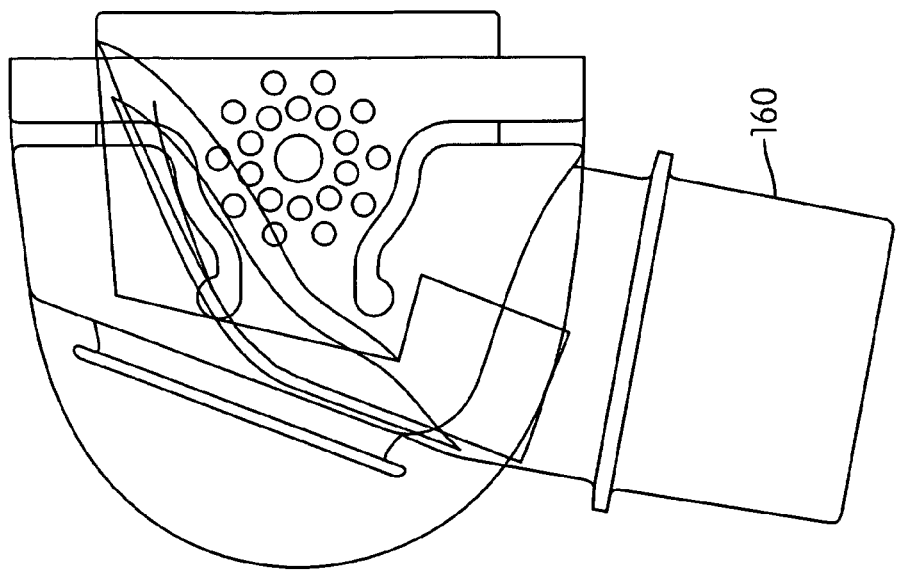
FIG. 7*d* is a right side view of the swivel elbow shown in FIG. 7*a*.
Figure 7C:
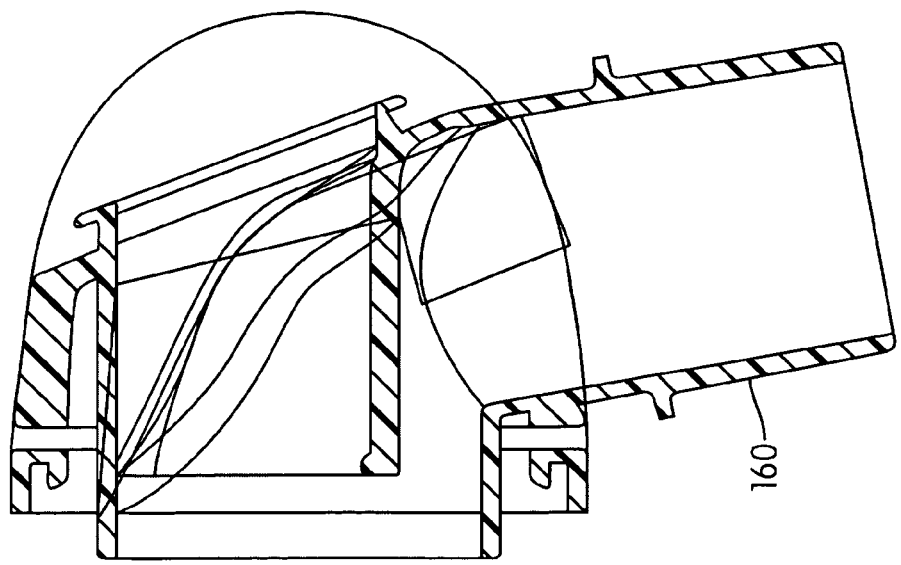
FIG. 7*c* is a cross-sectional view along line 7*c*-7*c* of the swivel elbow shown in FIG. 7*a*.
Figure 7E:
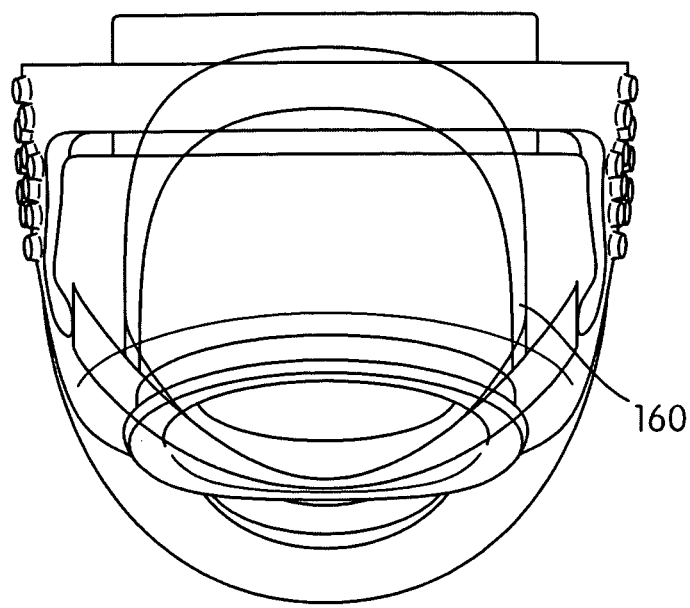
FIG. 7*e* is a top view of the top of the swivel elbow shown in FIG. 7*a*.
Figure 7F:
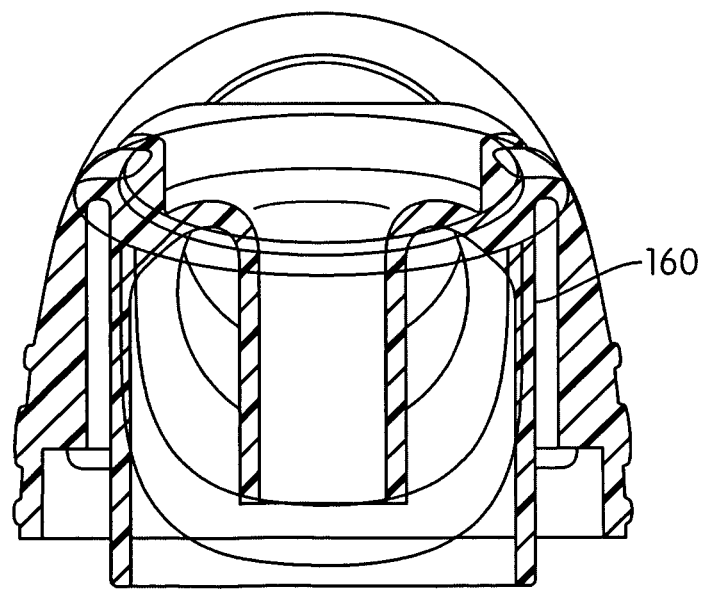
FIG. 7*f* a cross-sectional view along line 7*f*-7*f* of the swivel elbow shown in FIG. 7*b*.
Figure 7H:
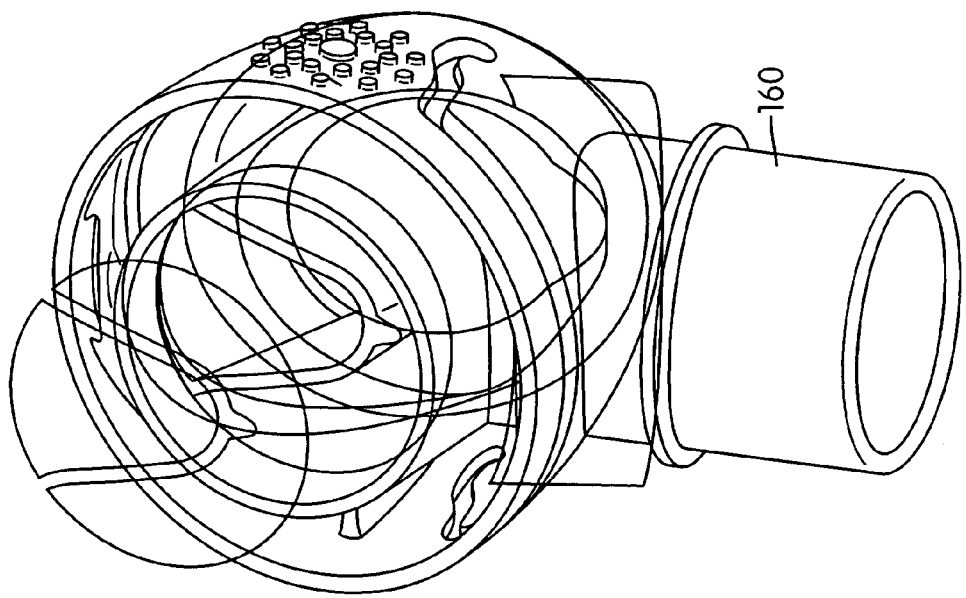
FIG. 7*h* is a front perspective view of the swivel elbow shown in FIG. 7*a*.
Figure 7G:
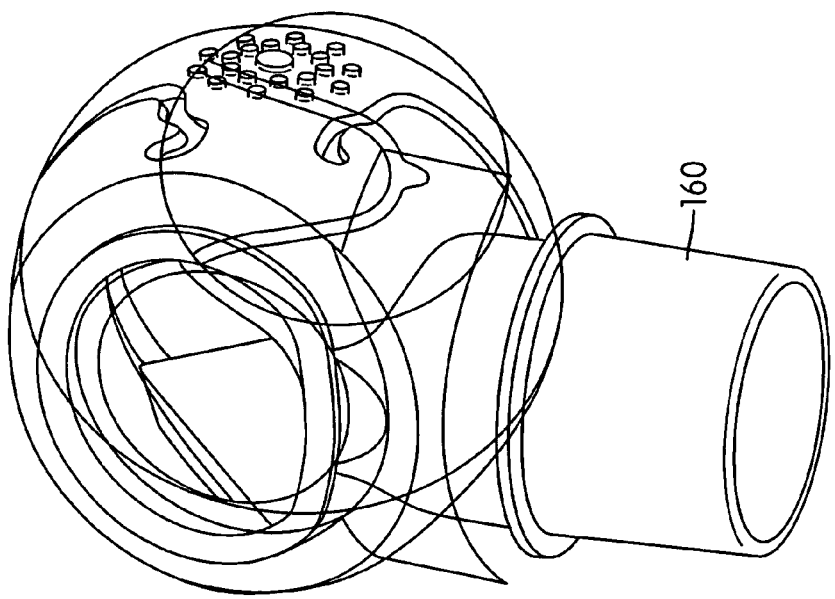
FIG. 7*g* is a rear perspective view of the swivel elbow shown in FIG. 7*a*.
Figure 7I:
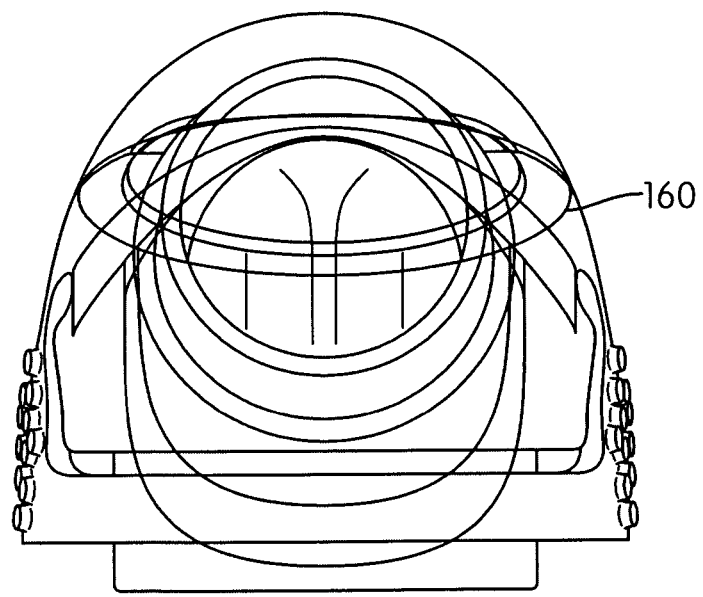
FIG. 7*i* is a bottom view of the swivel elbow shown in FIG. 7*a*.
Figure 8B:
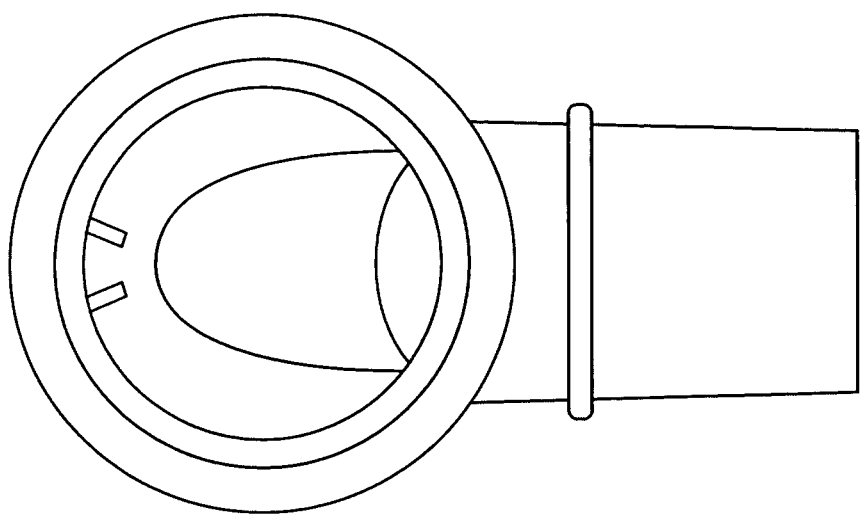
FIG. 8*b* is a rear view of a prior art swivel elbow.
Figure 8A:
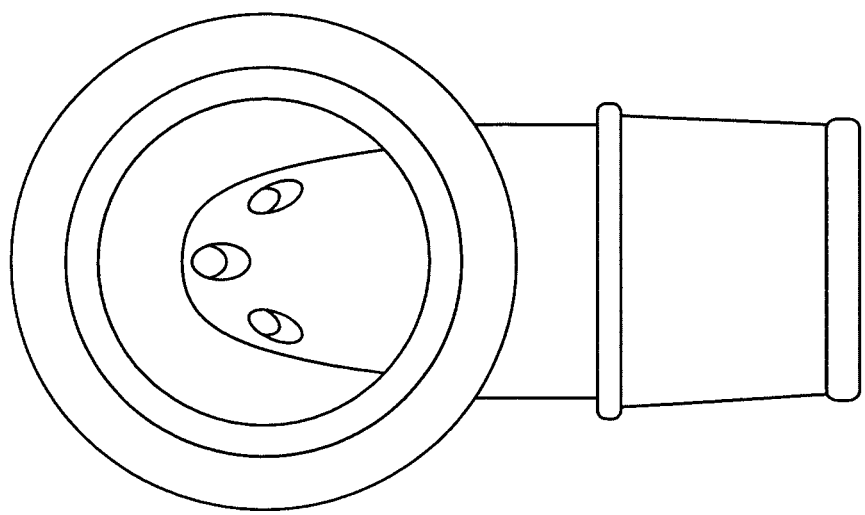
FIG. 8*a* is a rear view of a prior art swivel elbow.
Figure 8D:
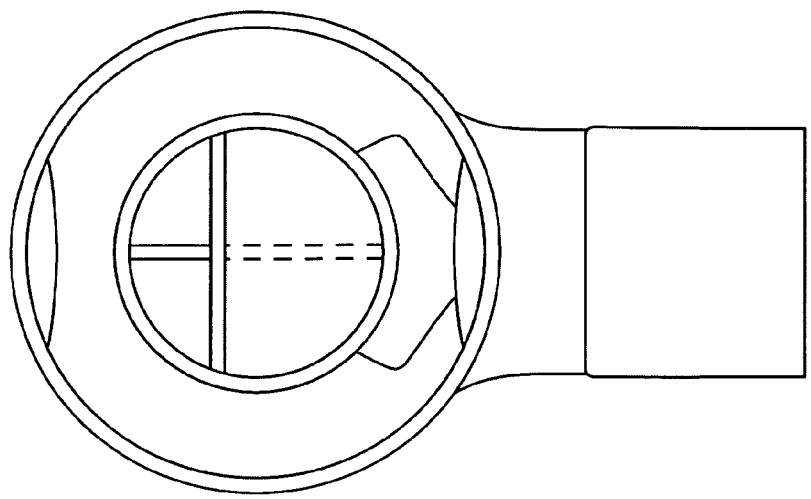
FIG. 8*d* is a rear view of a related art swivel elbow.
Figure 8C:
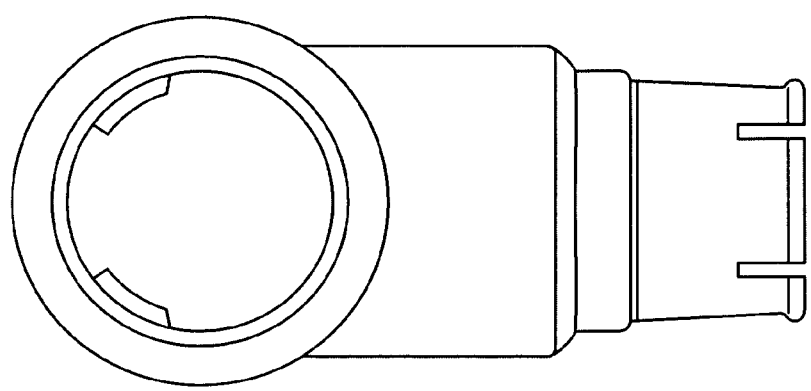
FIG. 8*c* is a rear view of a related art swivel elbow.
Figure 9B:
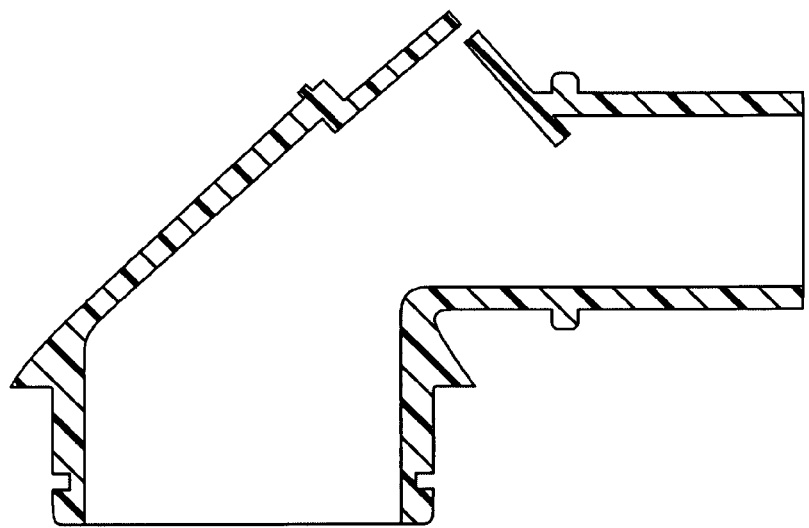
FIG. 9*b* is a cross-sectional view of the front of the swivel elbow shown in FIG. 8*b*.
Figure 9A:
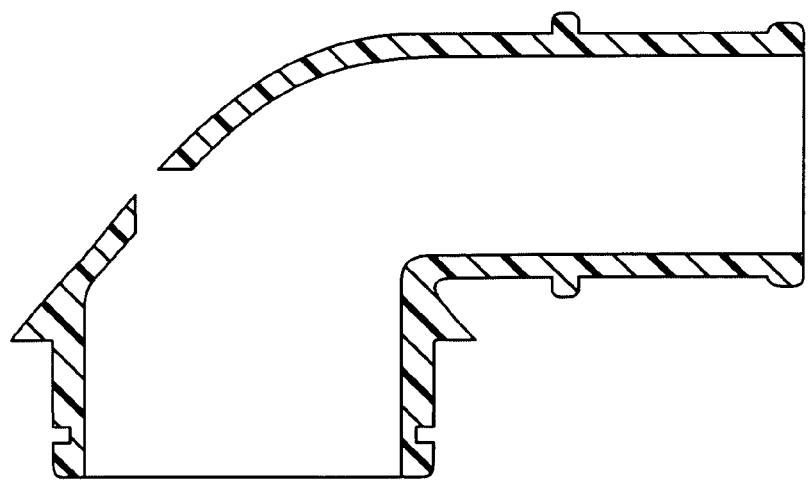
FIG. 9*a* is a cross-sectional view of the front of the swivel elbow shown in FIG. 8*a*.
Figure 9D:
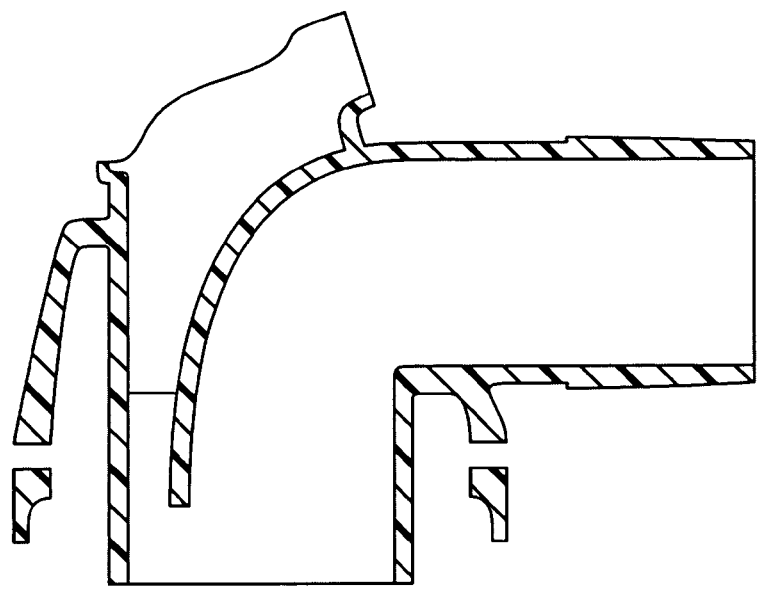
FIG. 9*d* is a cross-sectional view of the front of the swivel elbow shown in FIG. 8*d*.
Figure 9C:
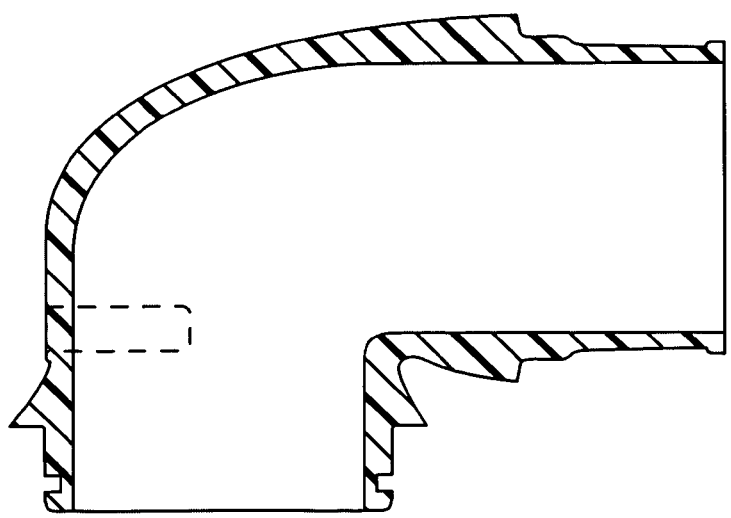
FIG. 9*c* is a cross-sectional view of the front of the swivel elbow shown in FIG. 8*c*.
Figure 10C:
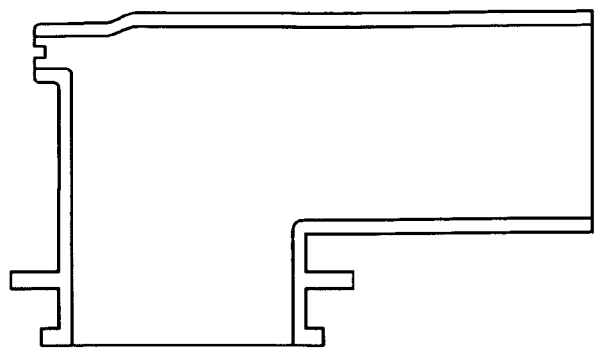
FIG. 10*c* is a cross-sectional view of a prior art swivel elbow.
Figure 10B:
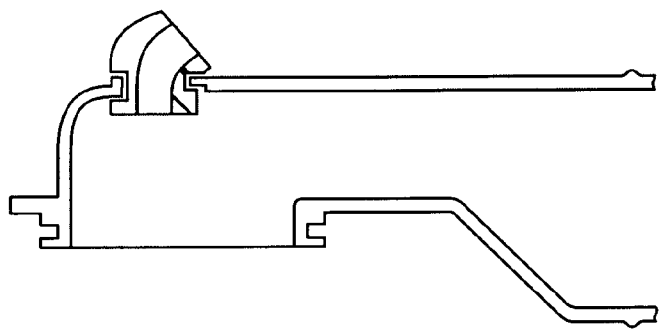
FIG. 10*b* is a cross-sectional view of a related art swivel elbow.
Figure 10A:
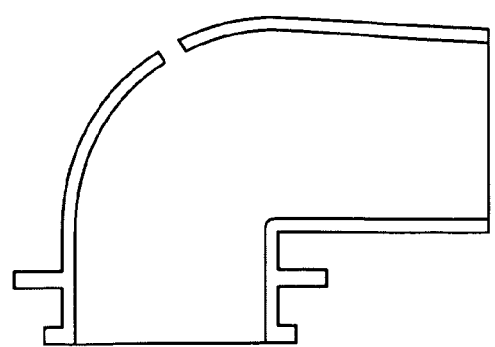
FIG. 10*a* is a cross-sectional view of a prior art swivel elbow.
Figure 11A:
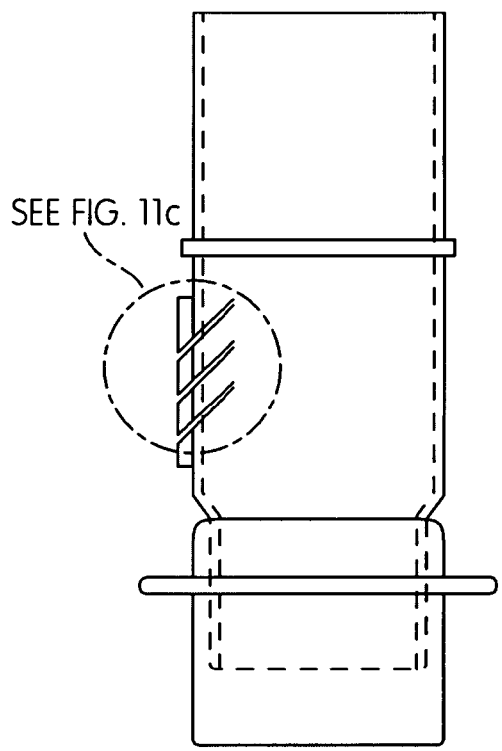
FIG. 11*a* is a front view of a side of a part of a prior art swivel elbow.
Figure 11B:
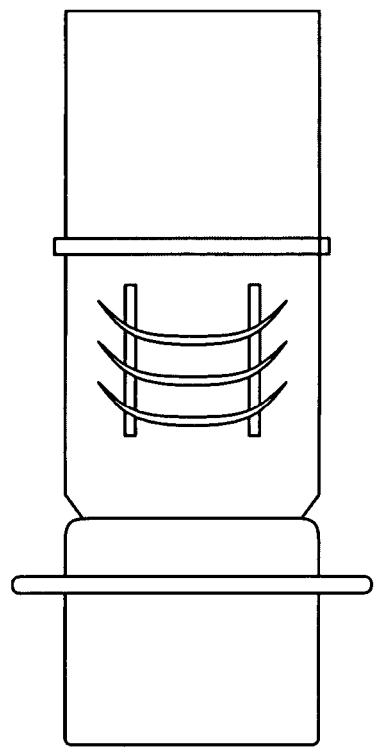
FIG. 11*b* is a left side view of the swivel elbow shown in FIG. 11*a*.
Figure 11C:
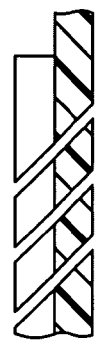
FIG. 11*c* is a detailed cross-sectional view of vents on the swivel elbow shown in FIG. 11*a*.
Figure 11D:
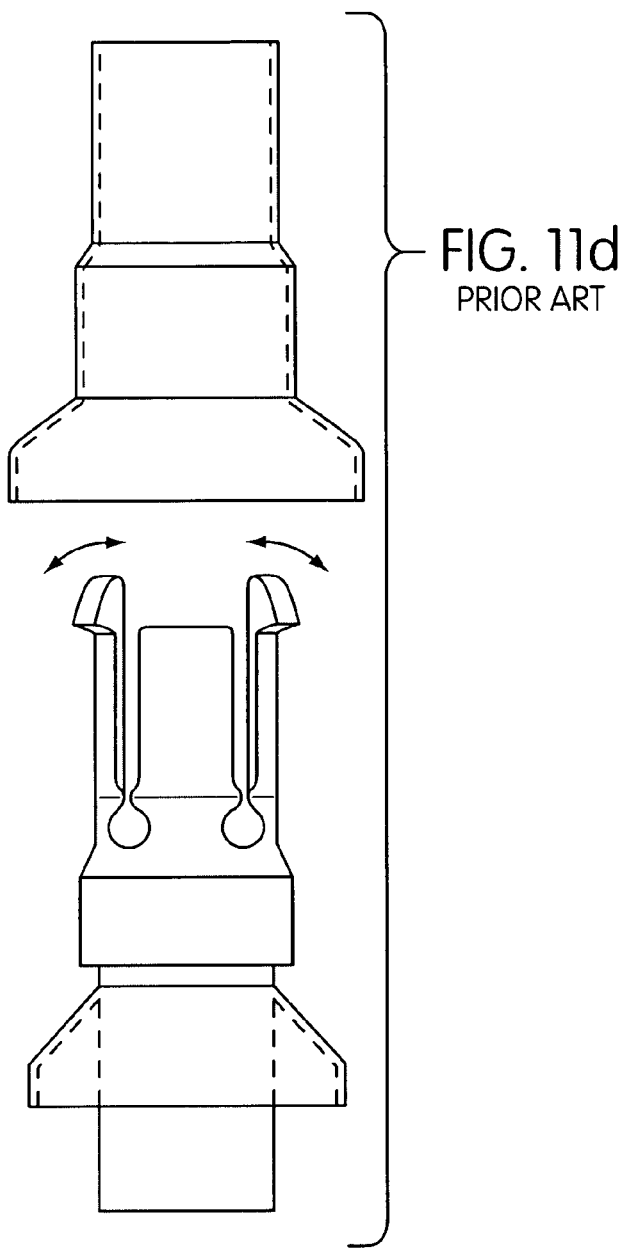
FIG. 11*d* is an exploded view of a part of another prior art swivel elbow.
Figure 11E:
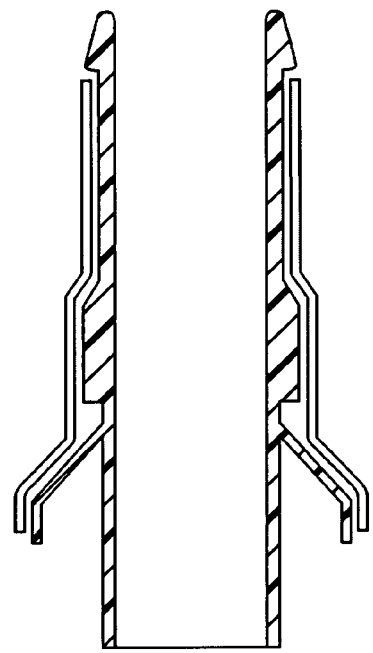
FIG. 11*e* is a cross-sectional view of the swivel elbow shown in FIG. 11*d* in an assembled state.
Figure 11F:
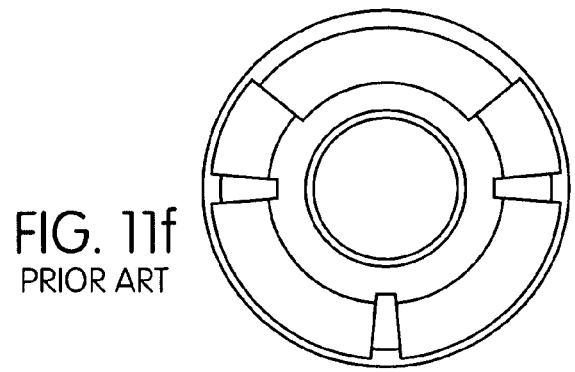
FIG. 11*f* is a bottom view of the swivel elbow shown in FIG. 11*e*.
Figure 12:
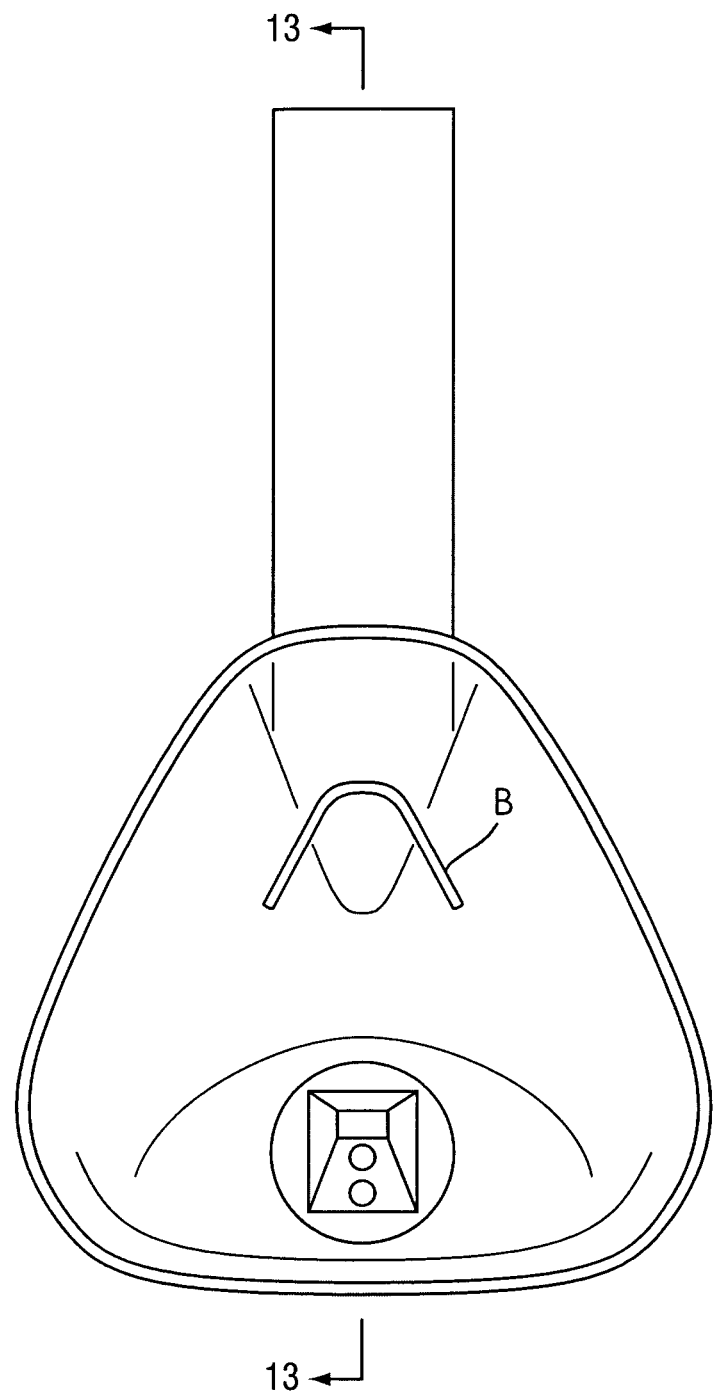
FIG. 12 is a rear view of a prior art respiratory mask assembly.
Figure 13:
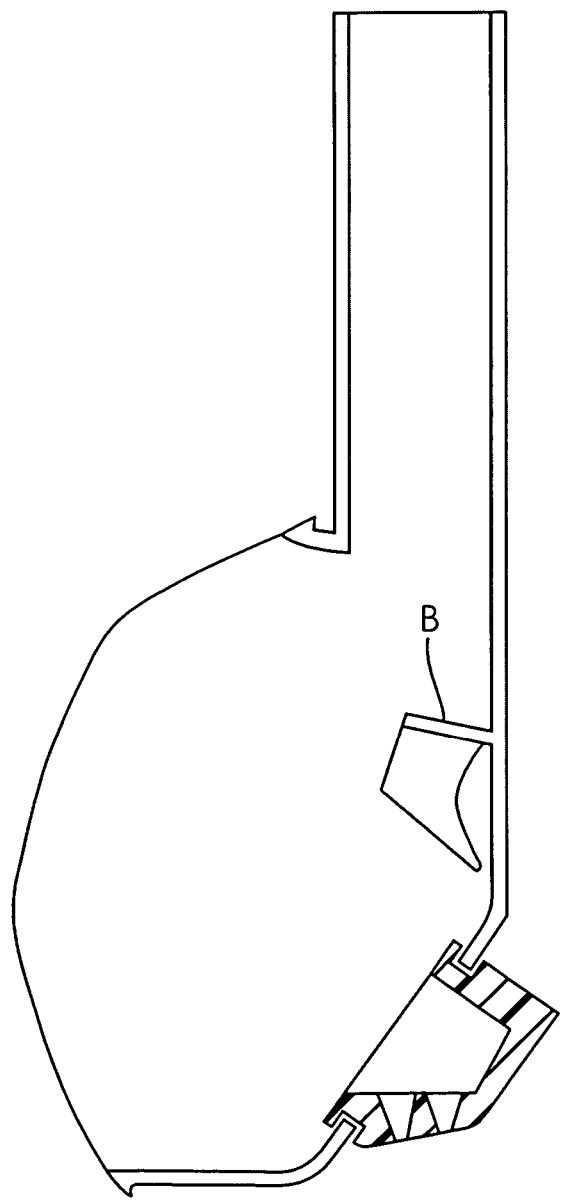
FIG. 13 is a cross-sectional view along line 13-13 of the respiratory mask assembly shown in FIG. 12.
Figure 14:
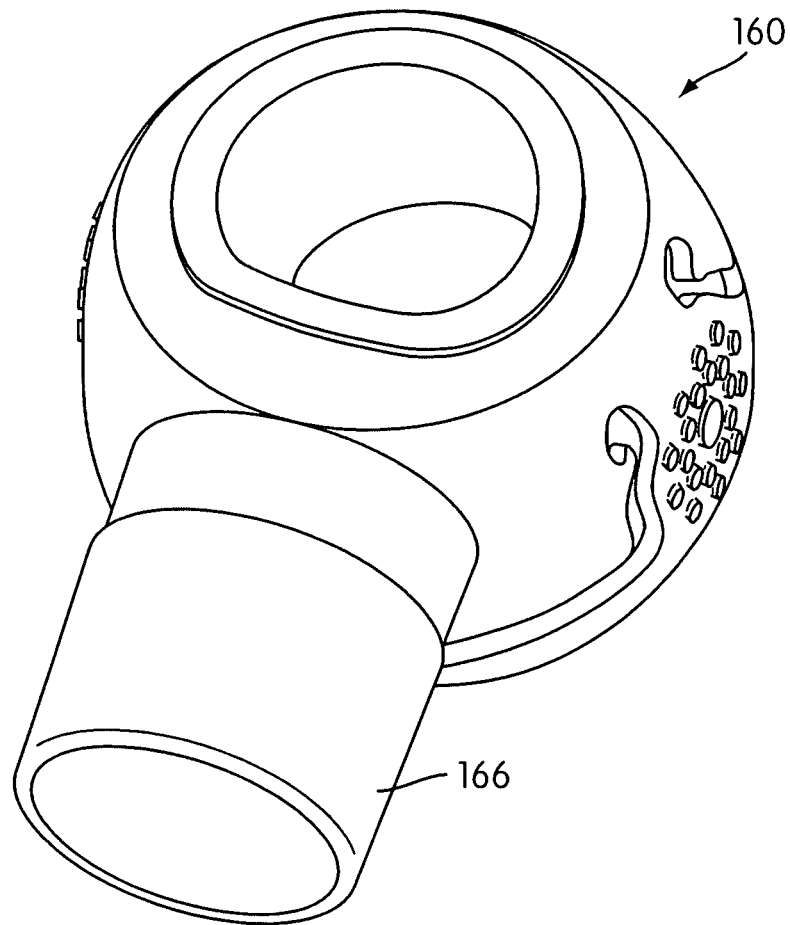
FIG. 14 is a front perspective view of a swivel elbow according to another embodiment of the invention.
Figure 15A:
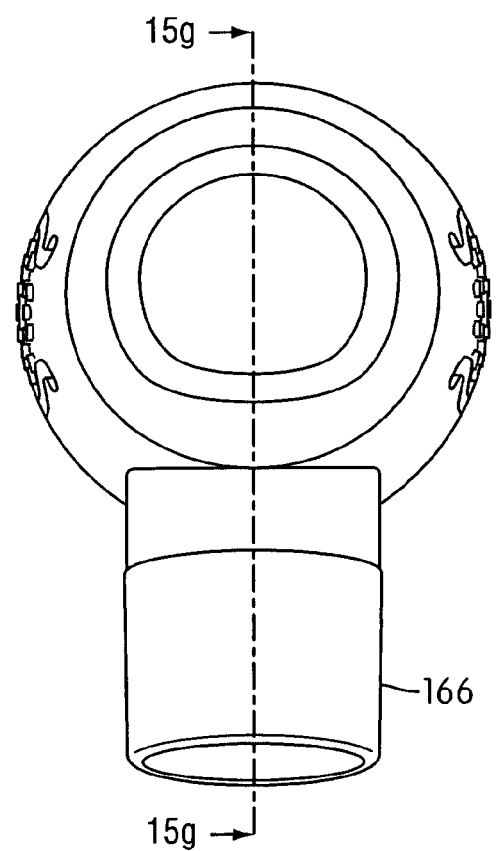
FIG. 15*a* is a front view of the swivel elbow shown in FIG. 14.
Figure 15B:
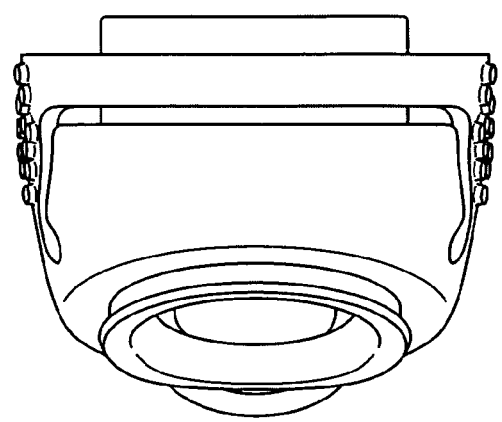
FIG. 15*b* is a top view of the swivel elbow shown in FIG. 15*a*.
Figure 15C:
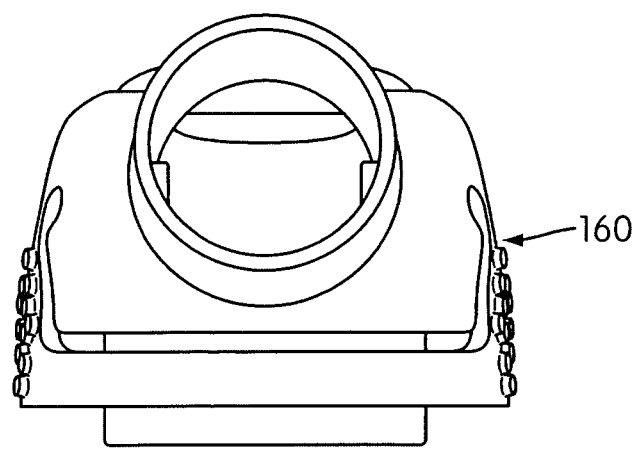
FIG. 15*c* is a bottom view of the swivel elbow shown in FIG. 15*a*.
Figure 15D:
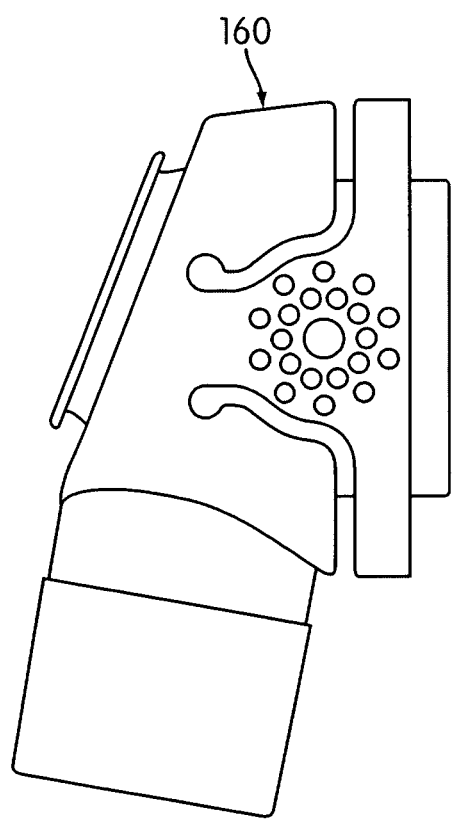
FIG. 15*d* is a right side view of the swivel elbow shown in FIG. 15*a*.
Figure 15E:
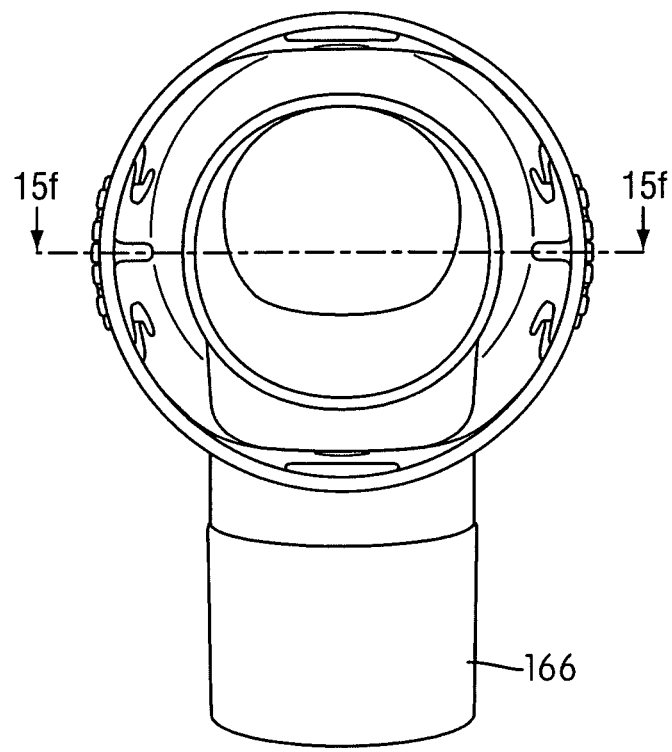
FIG. 15*e* is a right side view of the swivel elbow shown in FIG. 15*d*.
Figure 15F:
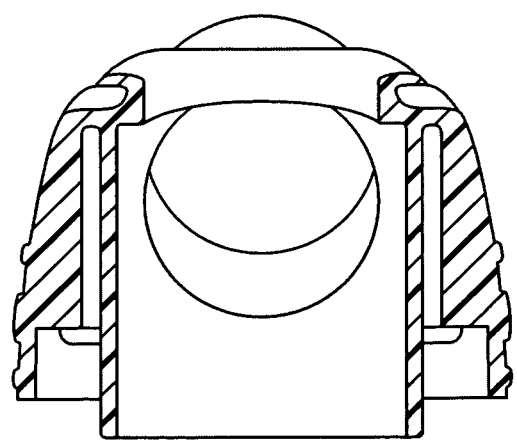
FIG. 15*f* is a cross-sectional view along line 15*f*-15*f* of the swivel elbow shown in FIG. 15*e*.
Figure 15G:
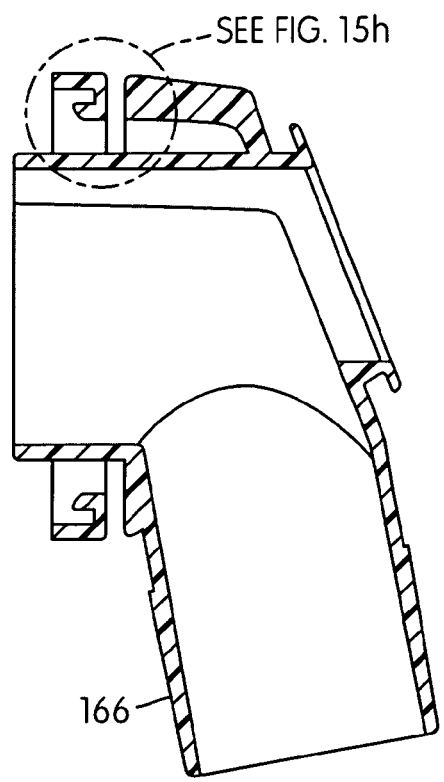
FIG. 15*g* is a cross-sectional view along line 15*g*-15*g* of the swivel elbow shown in FIG. 15*a*.
Figure 15H:
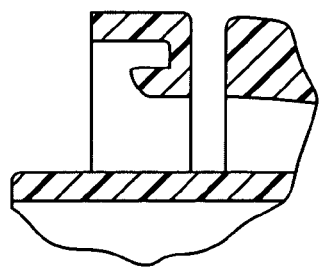
FIG. 15*h* is a detailed view of a portion of the swivel elbow shown in FIG. 15*g*.
Figure 15J:
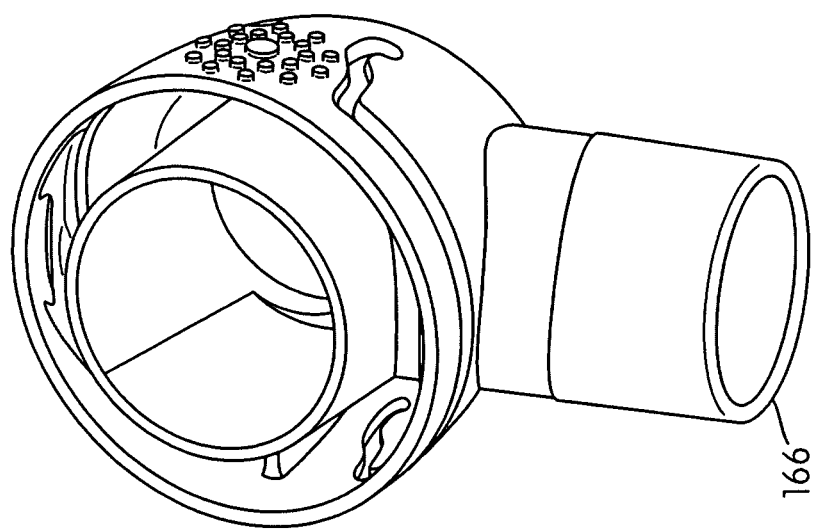
FIG. 15*j* is a rear perspective view of the swivel elbow shown in FIG. 15*a*.
Figure 15I:
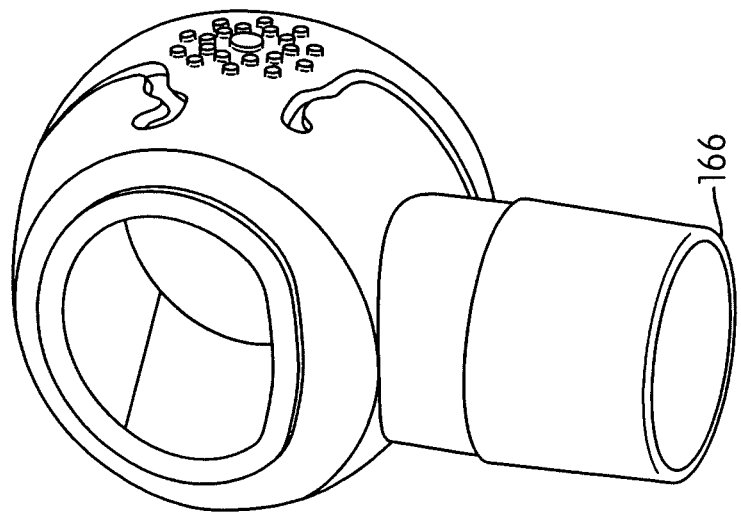
FIG. 15*i* is a front perspective view of the swivel elbow shown in FIG. 15*a*.

Other embodiments of the baffle 161 are shown in FIGS. 4*d* and 4*e*. In the embodiment shown in FIG. 4*d*, the baffle 161 does not contain the protrusion 163. In the embodiment shown in FIG. 4*e*, the baffle 161 is inverted with respect to FIGS. 4*b* and 4*d*. In the embodiments shown in FIGS. 4*b*, 4*d*, and 4*e*, the center line 100 is disposed vertically. However, it is within the scope of this invention that additional center lines be disposed horizontally or at any angle between vertical and horizontal.

A variety of other baffle shapes are possible. For example, the baffle 161 may be M-, C-, or V-shaped. A further advantage of a baffle 161 in accordance with an embodiment of the invention is that the cross-sectional area of the exhaust flow path increases from a first end in the interior of the mask to a second end, near the exhaust port 164. In this way, the velocity of the air exhausted via the exhaust port 164 is slowed down, or at least not increased, as it flows out of the elbow 160. This contributes to decreasing the noise of the vent. It is also within the scope of the invention for the elbow 160 to be or be devoid of a vent cavity.

An embodiment of the invention with an M-shaped baffle and increasing vent cavity is shown in FIGS. 18*a* to 19*j*. An embodiment of the invention with a V-shaped baffle and no vent cavity is shown in FIGS. 22*a* to 23*j*. An embodiment of the invention with a C-shaped baffle and increasing vent cavity is shown in FIGS. 24*a* to 25*j*. An embodiment of the invention with a V-shaped baffle and increasing vent cavity is shown in FIGS. 28*a* to 29*j*. All the baffle shapes described provide noise reduction, increased $CO_2$ washout, and/or optimized and/or low flow impedance. Additional baffle 161 shapes and orientations are possible and within the scope of the present invention.

As mentioned earlier the baffle 161 defines an inlet port 162, through which air from a blower can enter, and an exhaust port 164 within the elbow 160. Air from the blower passes through the air tube 168 to the elbow 160, where it passes through the inlet port 161 and is "injected" into the cavity 35 of the mask 10. Air continually flows from the mask cavity 35 out to atmosphere via the ring 400 to the exhaust port 164 of the elbow 160.

Figure 16B:
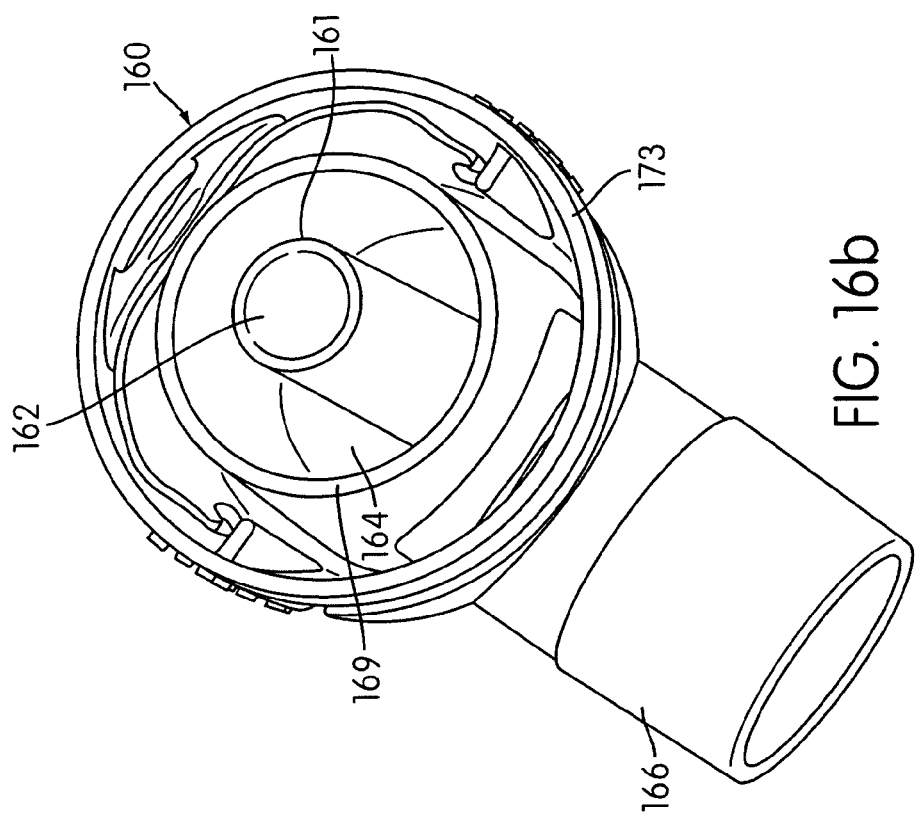
FIG. 16*b* is a rear perspective view of the swivel elbow shown in FIG. 16*a*.
Figure 16A:
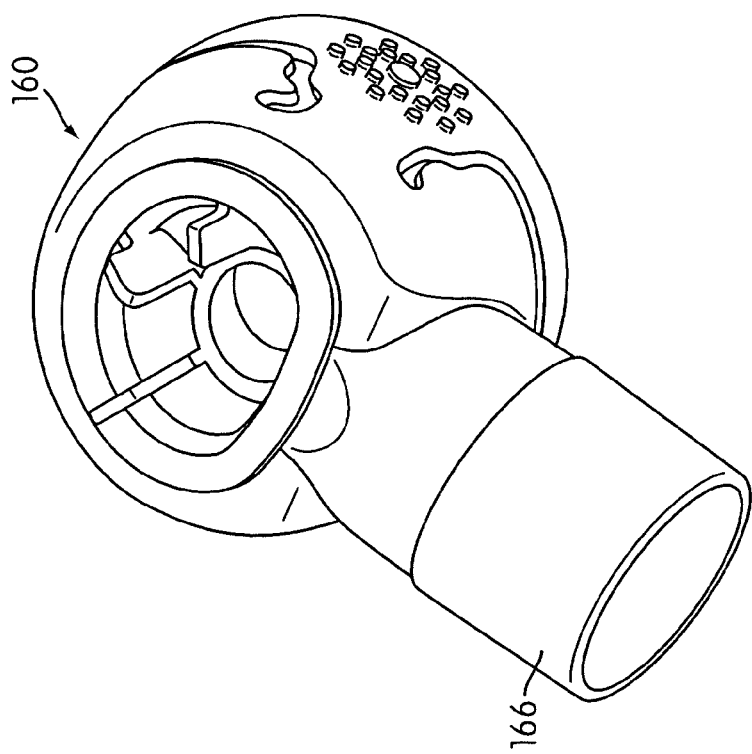
FIG. 16*a* is a front perspective view of a swivel elbow according to another embodiment of the invention.
Figure 17A:
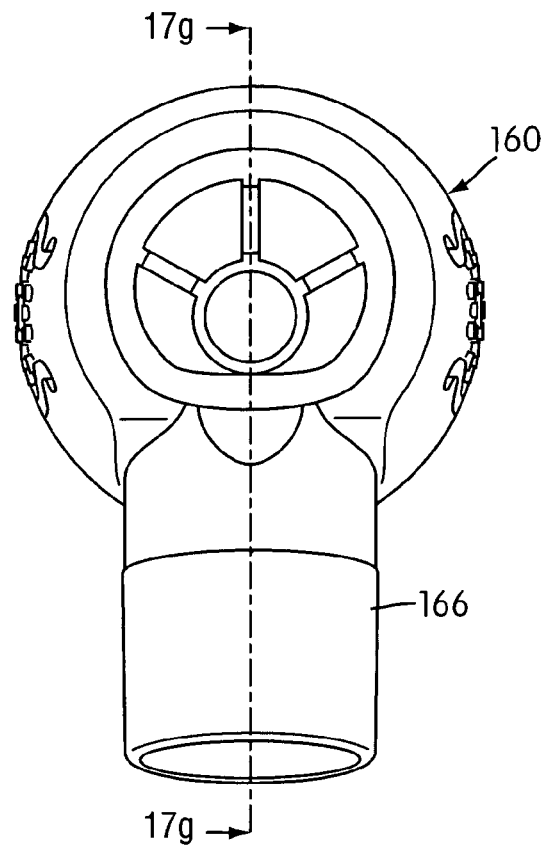
FIG. 17*a* is a front view of the swivel elbow shown in FIG. 16*a*.
Figure 17B:
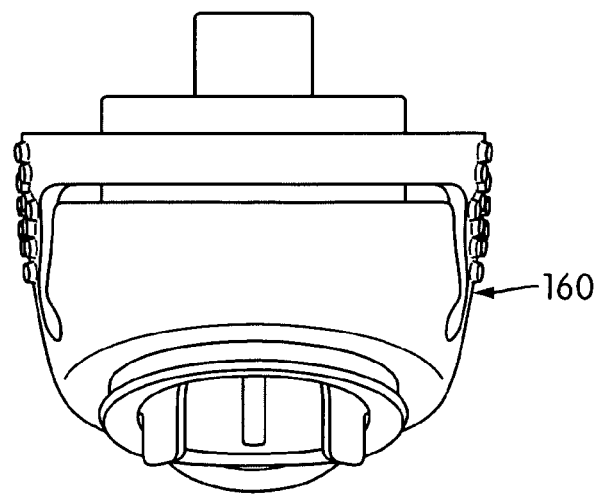
FIG. 17*b* is a top view of the swivel elbow shown in FIG. 17*a*.
Figure 17C:
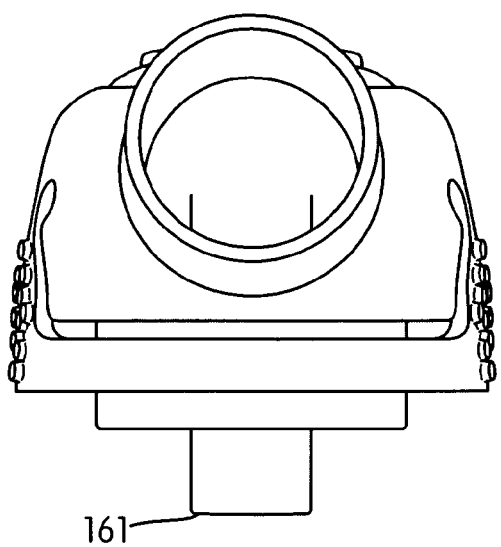
FIG. 17*c* is a bottom view of the swivel elbow shown in FIG. 17*a*.
Figure 17D:
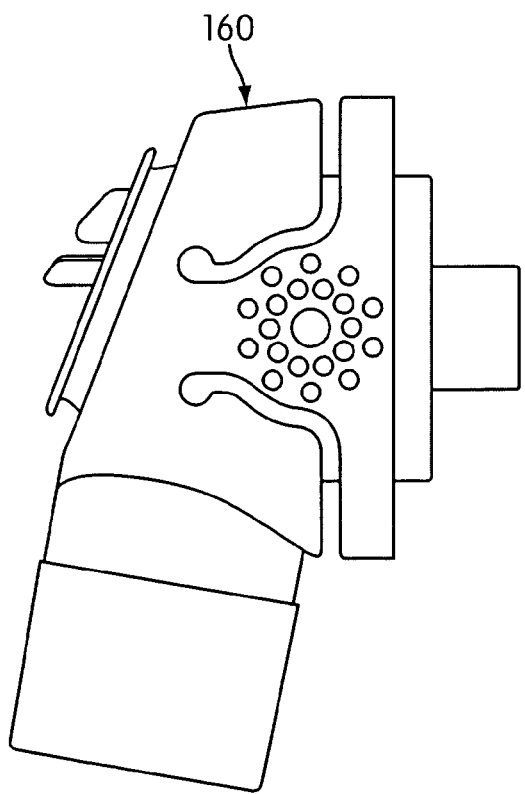
FIG. 17*d* is a right side view of the swivel elbow shown in FIG. 17*a*.
Figure 17E:
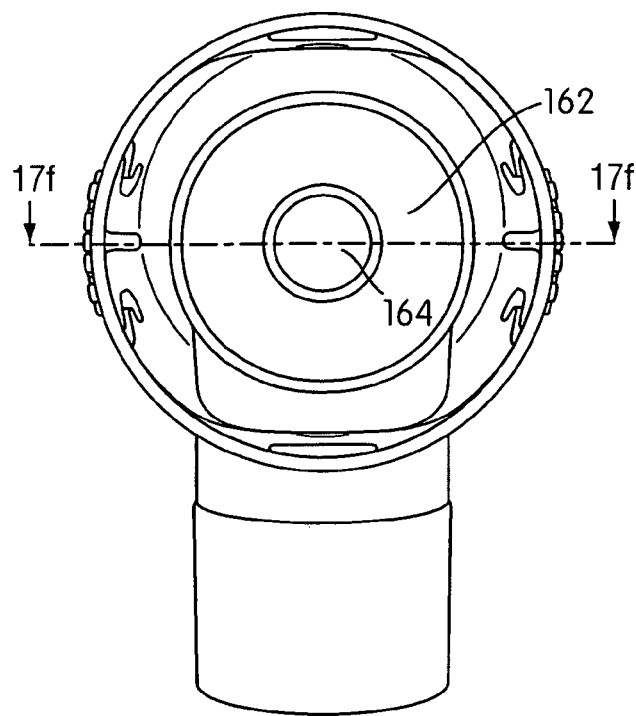
FIG. 17*e* is a rear view of the swivel elbow shown in FIG. 17*a*.
Figure 17F:
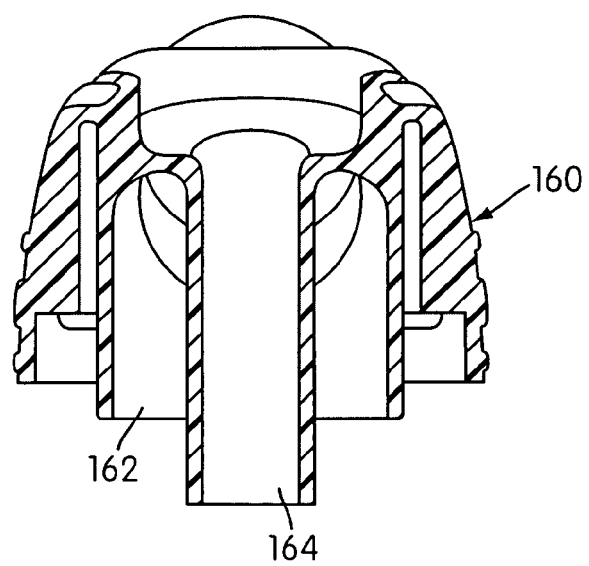
FIG. 17*f* is a cross-sectional view along line 17*f*-17*f* of the swivel elbow shown in FIG. 17*e*.
Figure 17G:
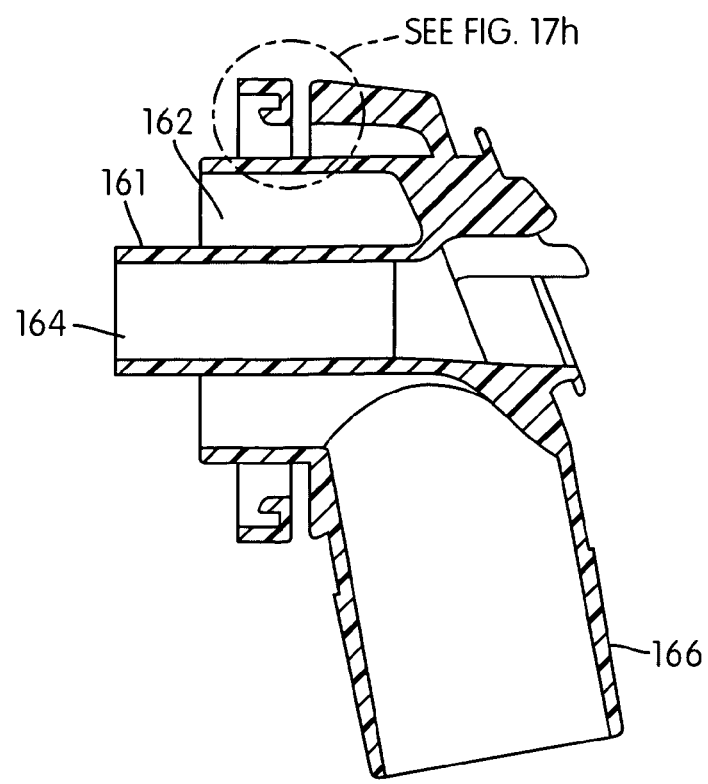
FIG. 17*g* is a cross-sectional view along line 17*g*-17*g* of the swivel elbow shown in FIG. 17*a*.
Figure 17H:
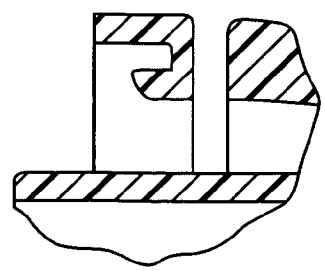
FIG. 17*h* is a detailed view of a portion of the swivel elbow shown in FIG. 17*g*.
Figure 17J:
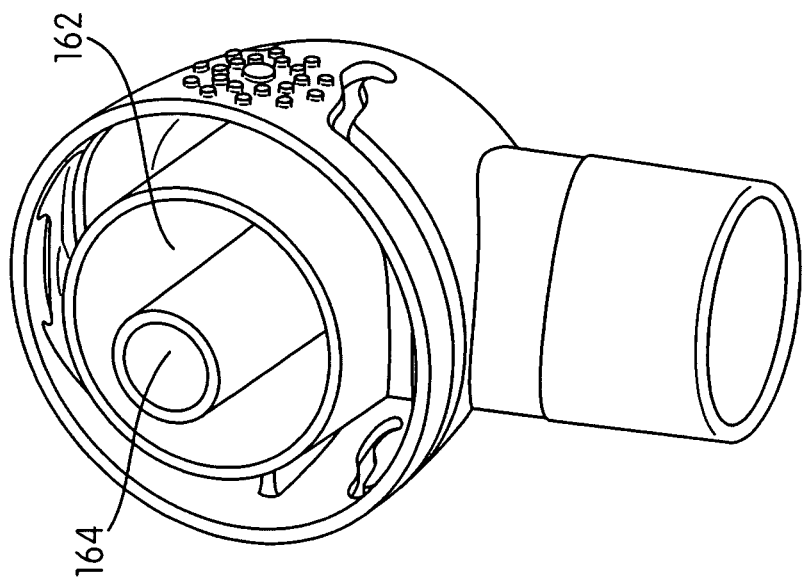
FIG. 17*j* is a rear perspective view of the swivel elbow shown in FIG. 16*b* at a slightly different angle.
Figure 17I:
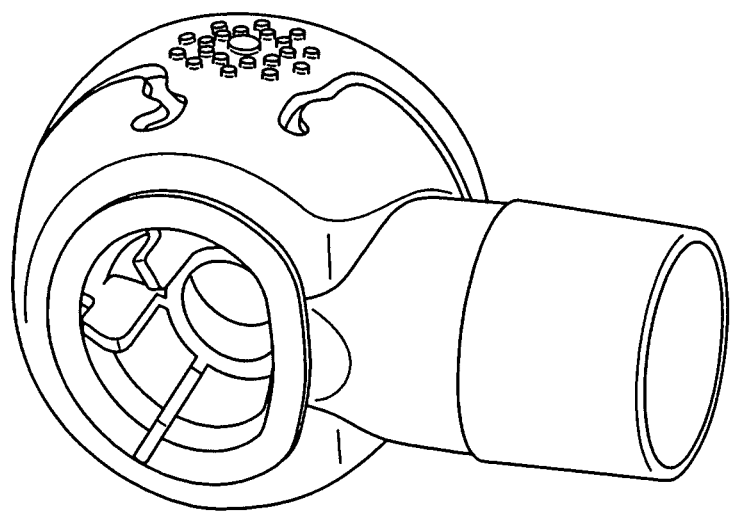
FIG. 17*i* is another front perspective view of the swivel elbow shown in FIG. 16*a* at a slightly different angle.
Figure 18B:
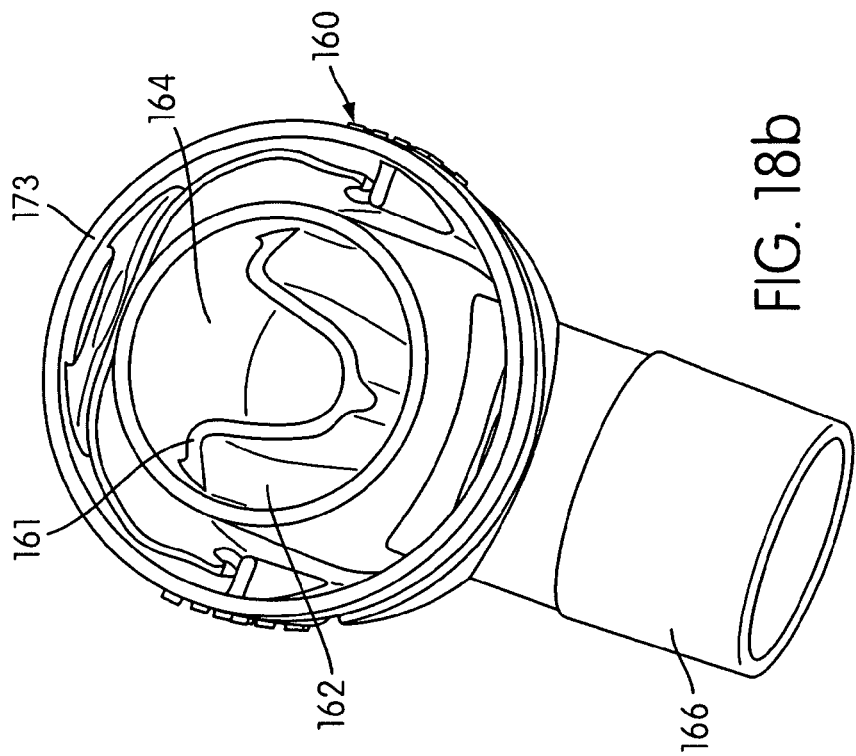
FIG. 18*b* is a rear perspective view of the swivel elbow shown in FIG. 18*a*.
Figure 18A:
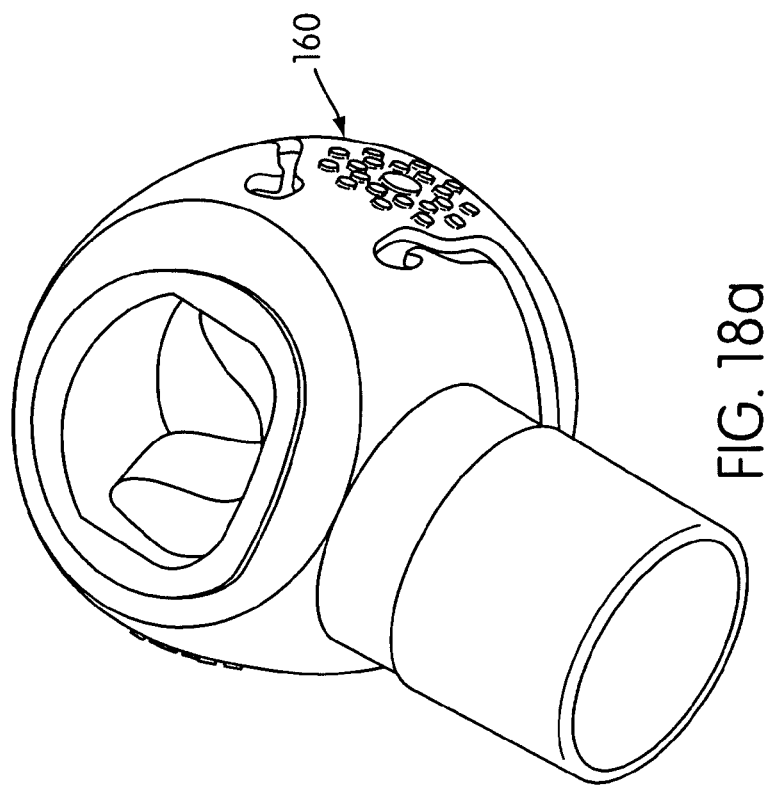
FIG. 18*a* is a front perspective view of a swivel elbow according to another embodiment of the invention.
Figure 19A:
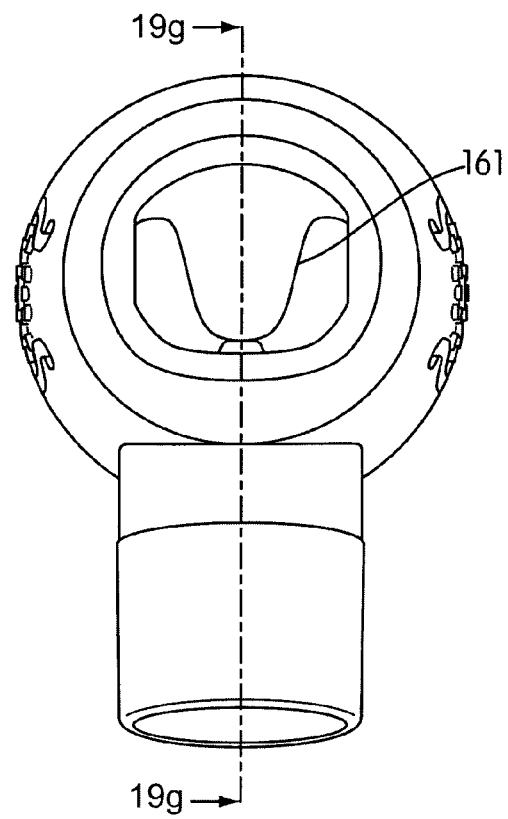
FIG. 19*a* is a front view of the swivel elbow shown in FIG. 18*a*.
Figure 19B:
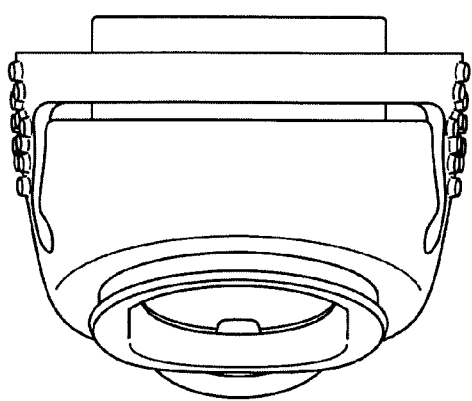
FIG. 19*b* is a top view of the swivel elbow shown in FIG. 19*a*.
Figure 19C:
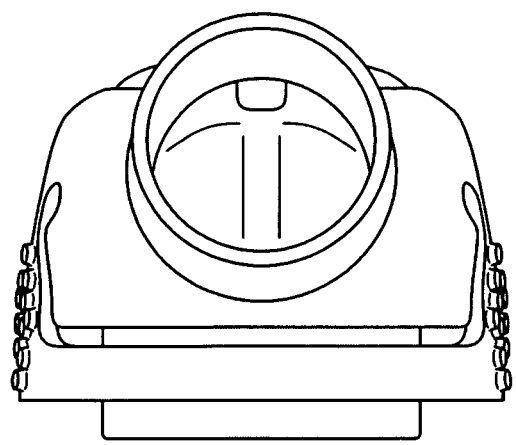
FIG. 19*c* is a bottom view of the swivel elbow shown in FIG. 19*a*.
Figure 19D:
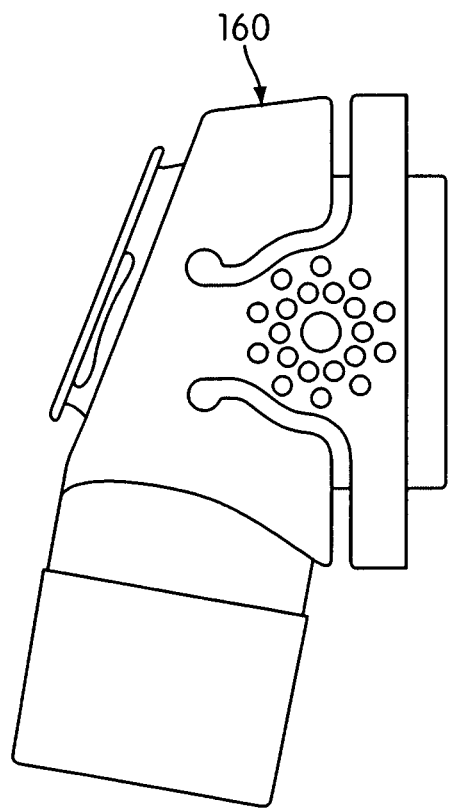
FIG. 19*d* is a right side view of the swivel elbow shown in FIG. 19*a*.
Figure 19E:
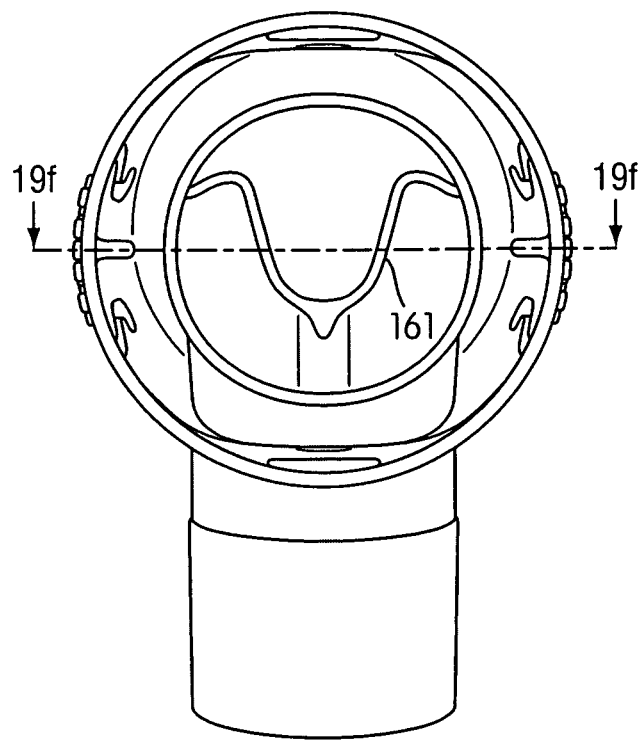
FIG. 19*e* is a rear view of the swivel elbow shown in FIG. 19*a*.
Figure 19F:
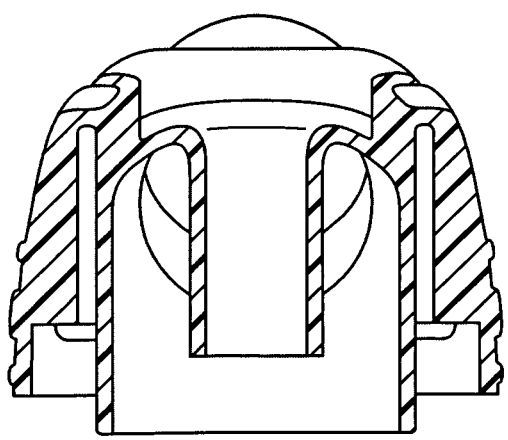
FIG. 19*f* is a cross-sectional view along line 19*f*-19*f* of the swivel elbow shown in FIG. 19*e*.
Figure 19G:
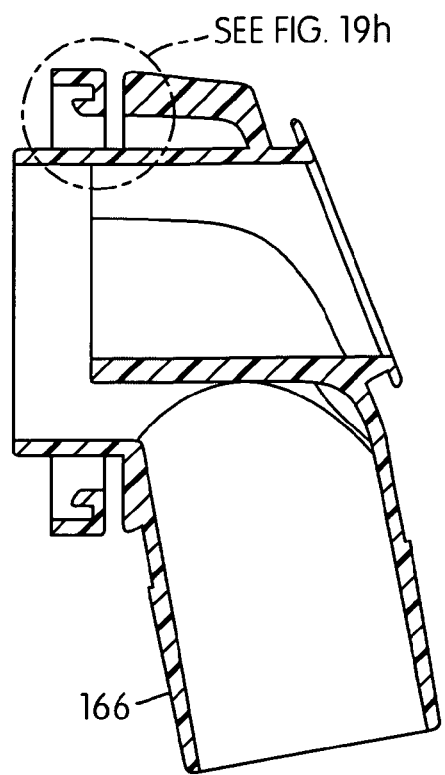
FIG. 19*g* is a cross-sectional view along line 19*g*-19*g* of the swivel elbow shown in FIG. 19*a*.
Figure 19H:
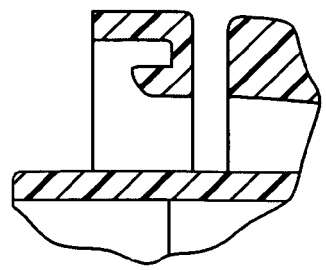
FIG. 19*h* is a detailed view of a portion of the swivel elbow shown in FIG. 19*g*.
Figure 19J:
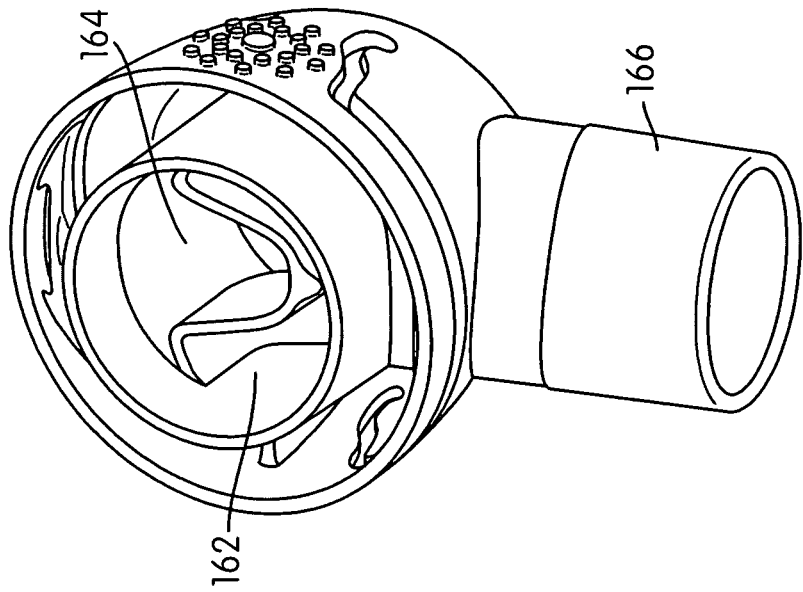
FIG. 19*j* is another rear perspective view of the swivel elbow shown in FIG. 18*b* at a slightly different angle.
Figure 19I:
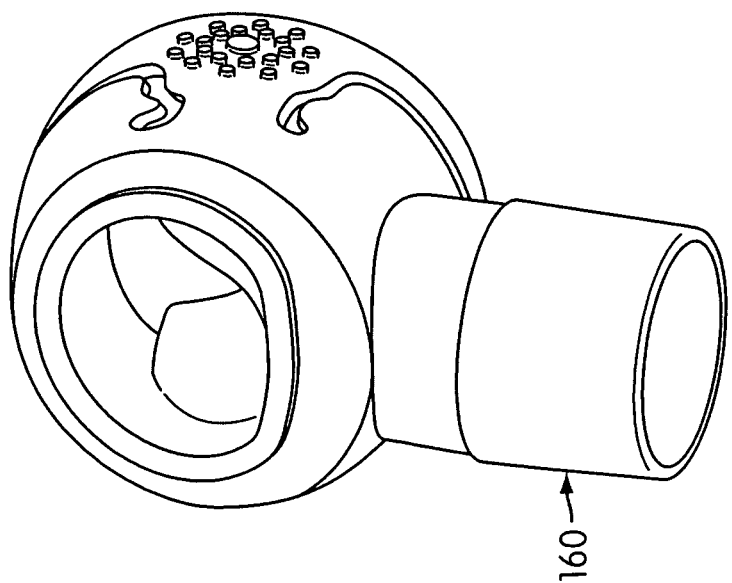
FIG. 19*i* is another front perspective view of the swivel elbow shown in FIG. 18*a* at a slightly different angle.
Figure 20B:
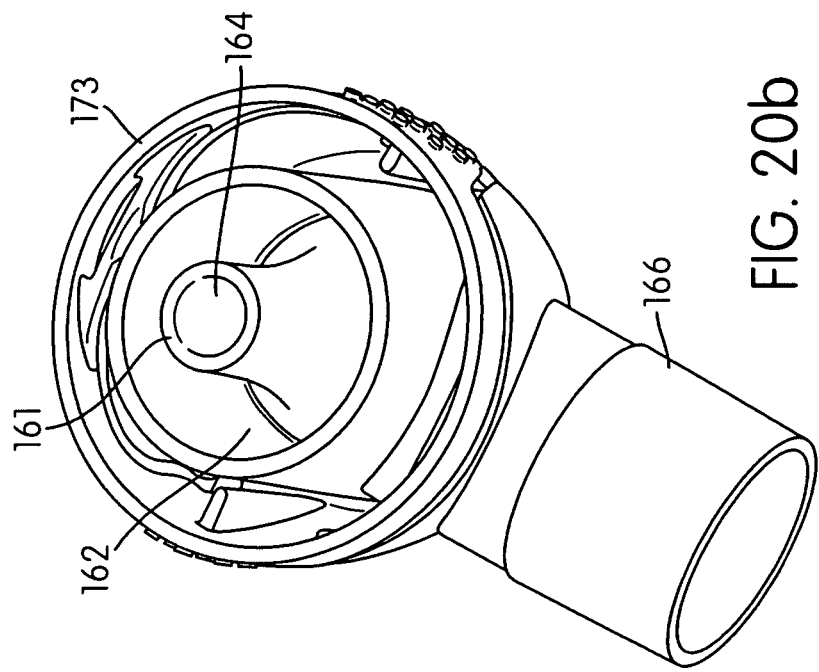
Figure 20A:
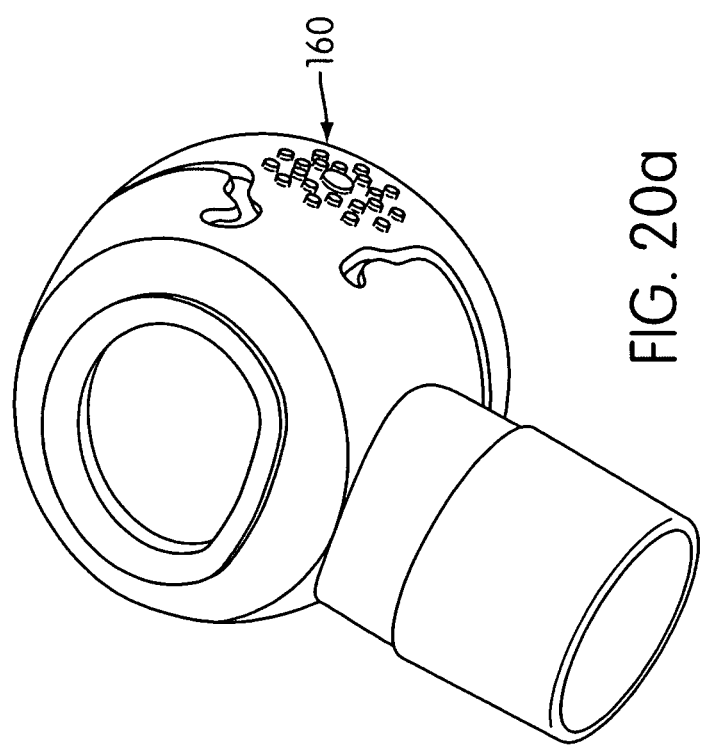
FIG. 20a is a front perspective view of a swivel elbow according to another embodiment of the invention.
Figure 21A:
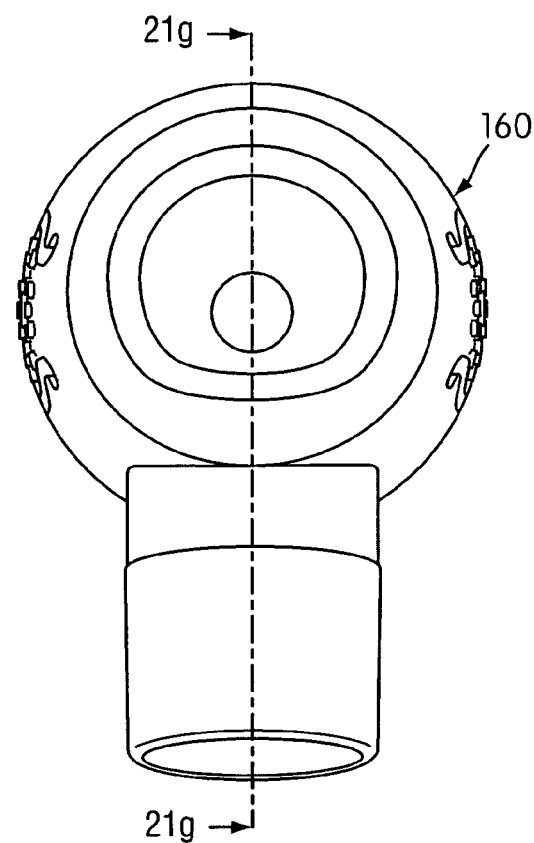
Figure 21B:
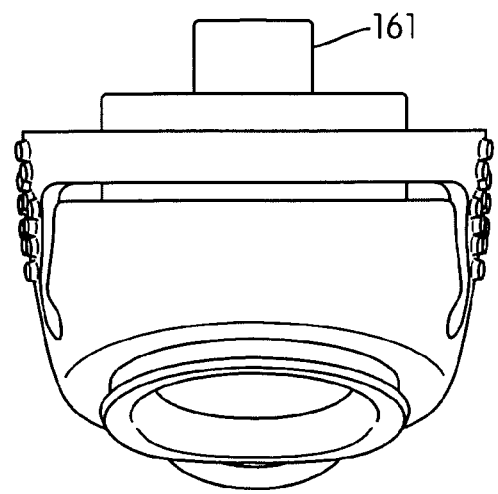
Figure 21C:
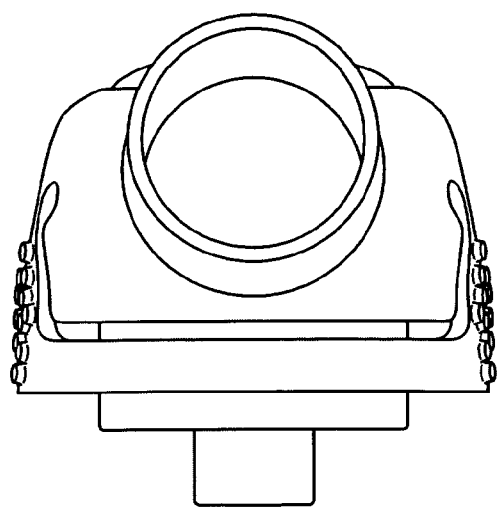
Figure 21D:
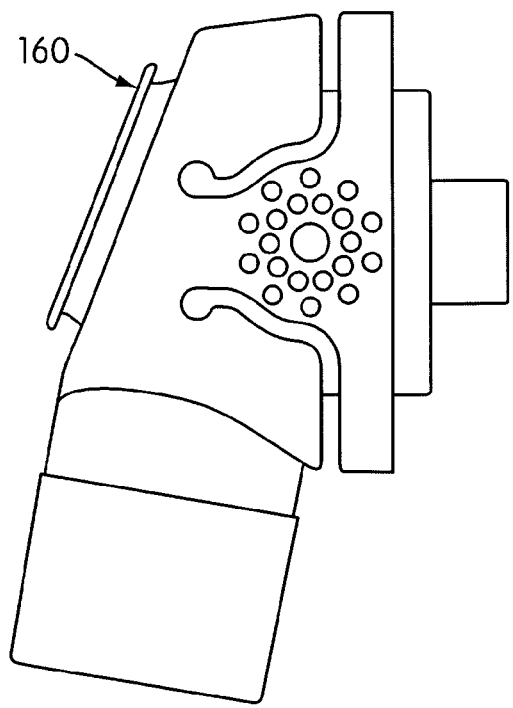
Figure 21E:
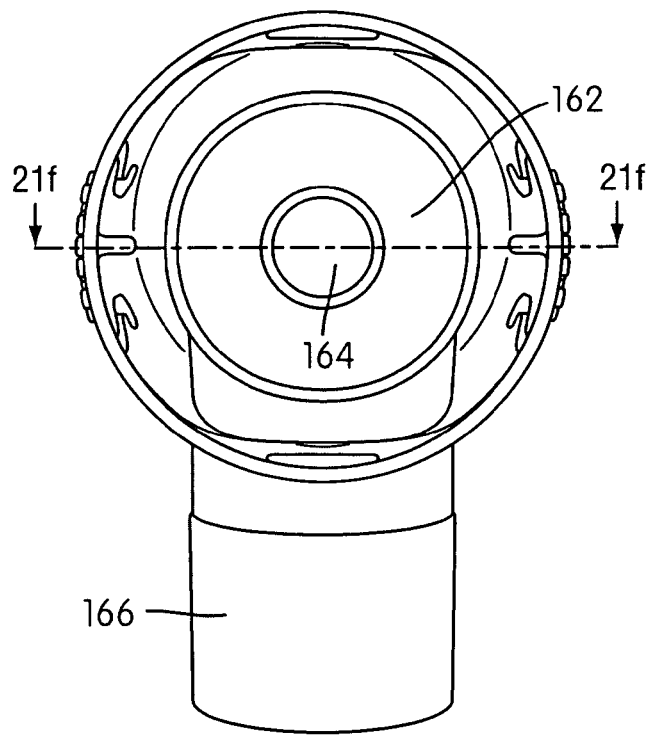
Figure 21F:
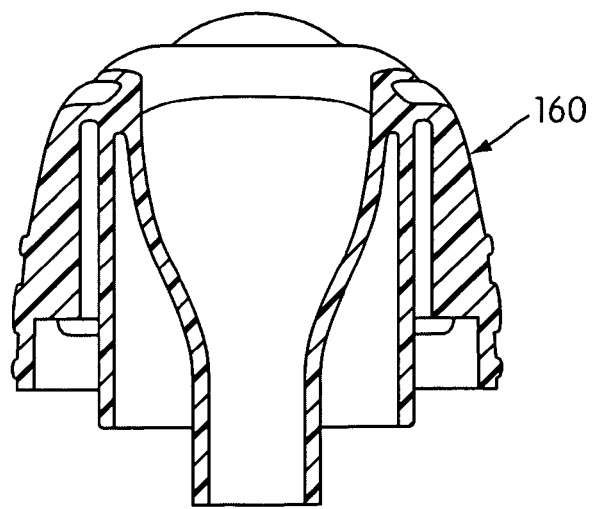
FIG. 21f is a cross-sectional view along line 21f-21f of the swivel elbow shown in FIG. 21e.
Figure 21G:
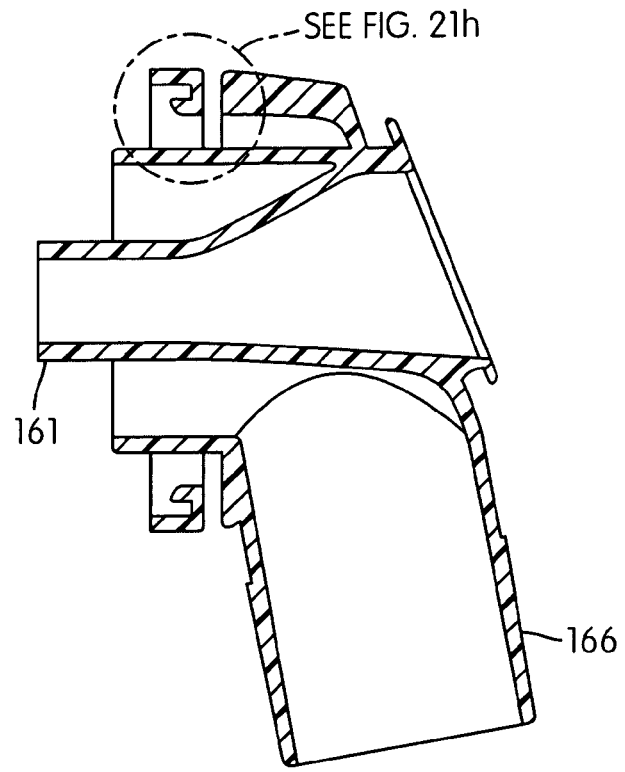
Figure 21H:
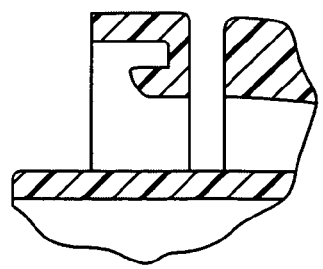
FIG. 21h is a detailed view of a portion of the swivel elbow shown in FIG. 21g.
Figure 21J:
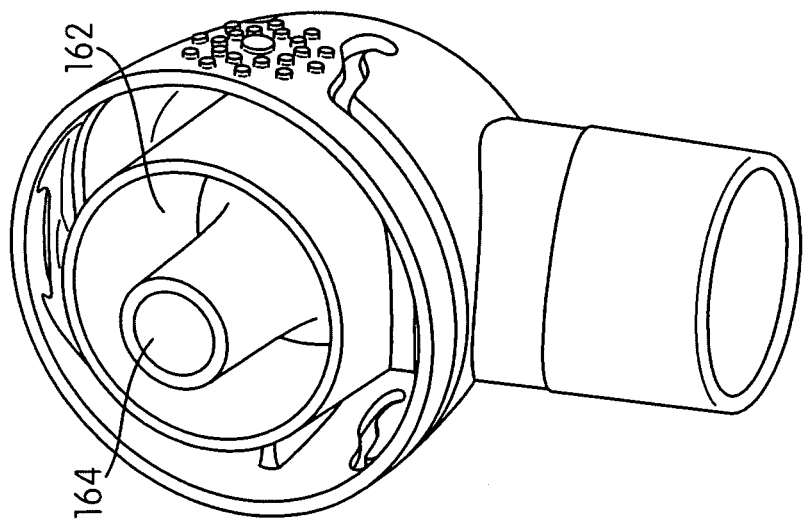
FIG. 21j is another rear perspective view of the swivel elbow shown in FIG. 20b at a slightly different angle.
Figure 21I:
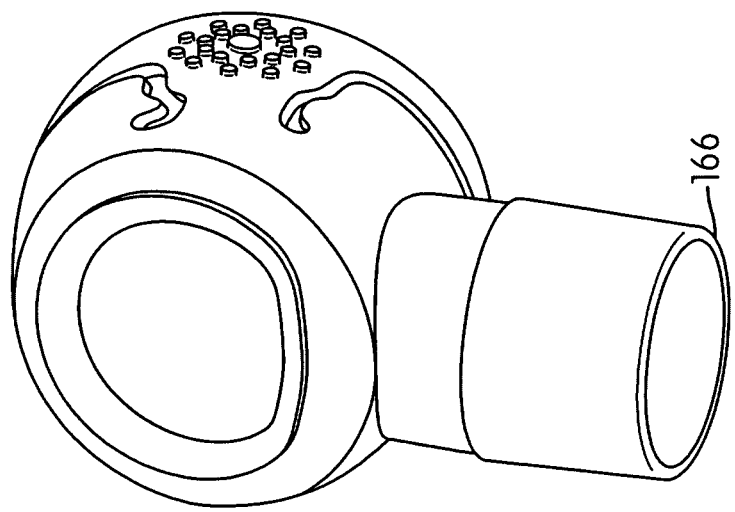
FIG. 21i is another front perspective view of the swivel elbow shown in FIG. 20a at a slightly different angle.
Figure 22A:
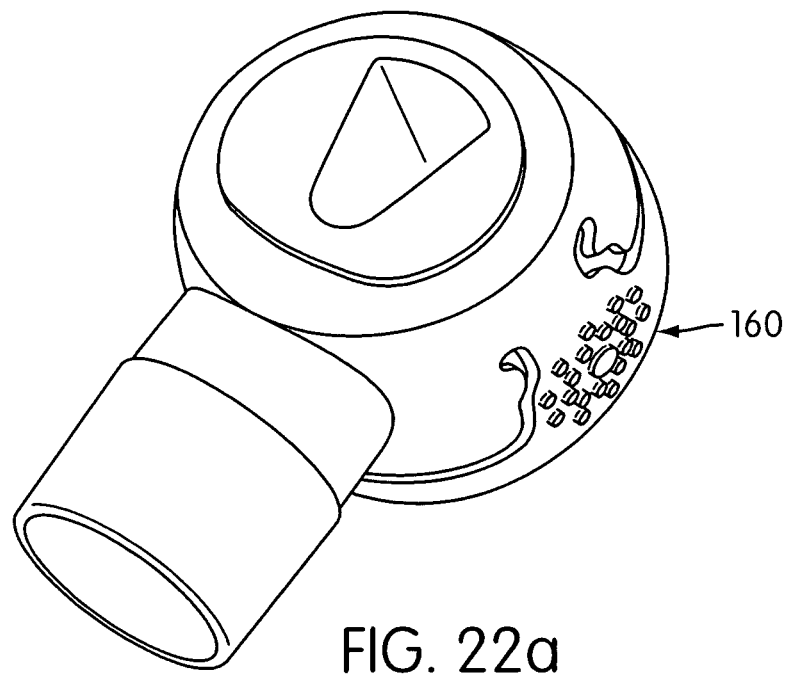
FIG. 22a is a front perspective view of a swivel elbow according to another embodiment of the invention.
Figure 22B:
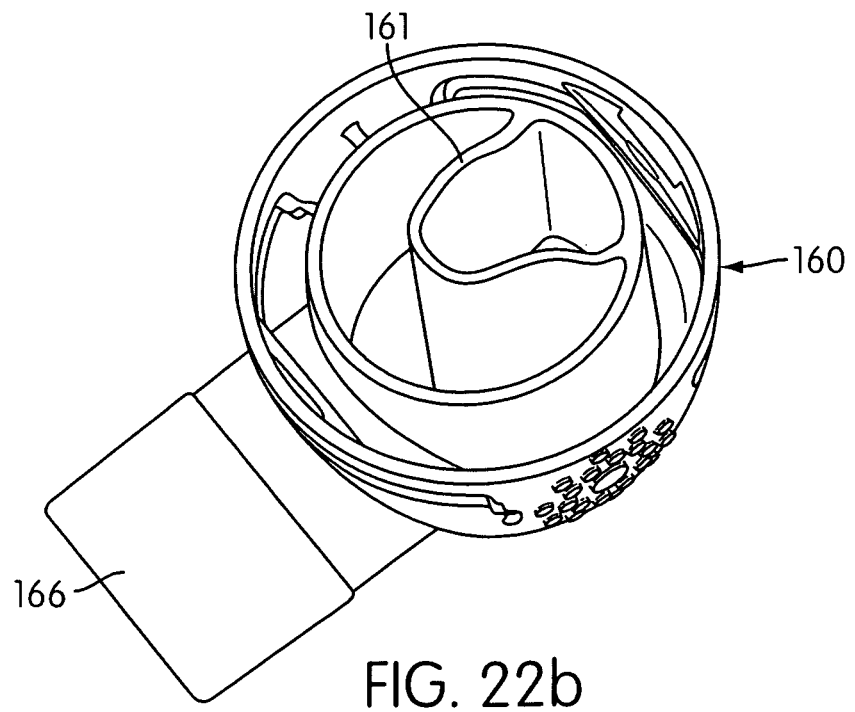
Figure 23A:
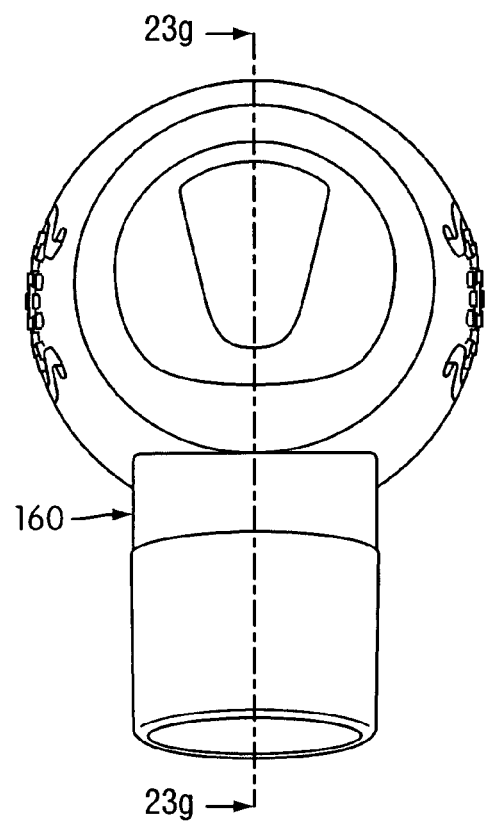
Figure 23B:
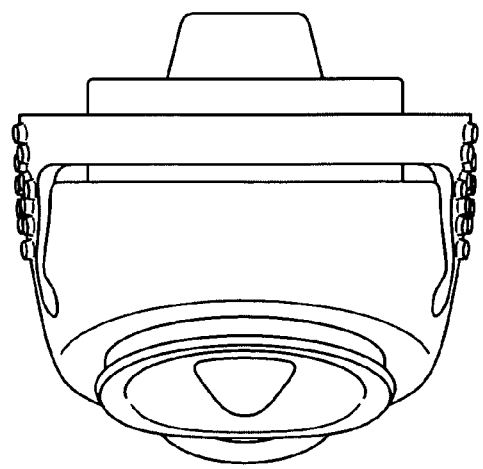
Figure 23C:
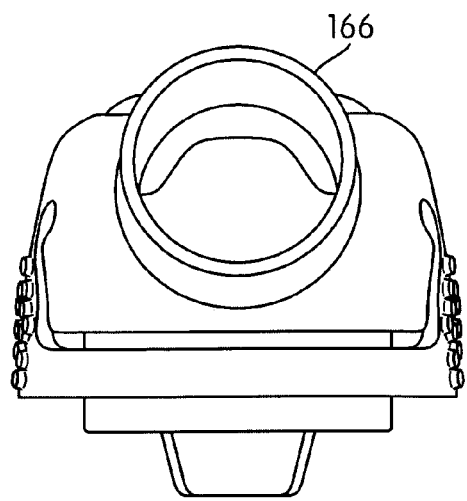
Figure 23D:
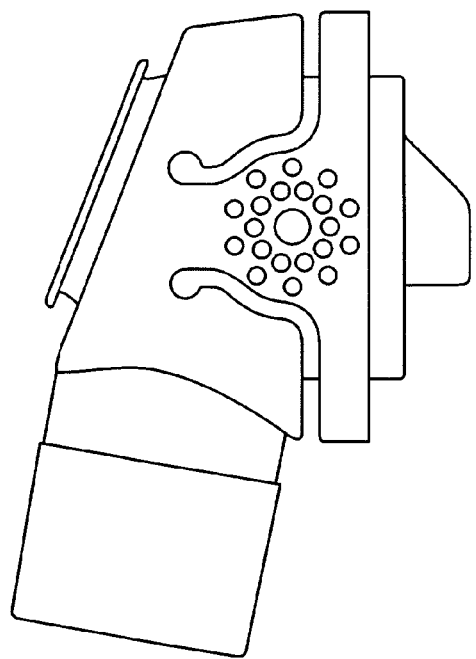
Figure 23E:
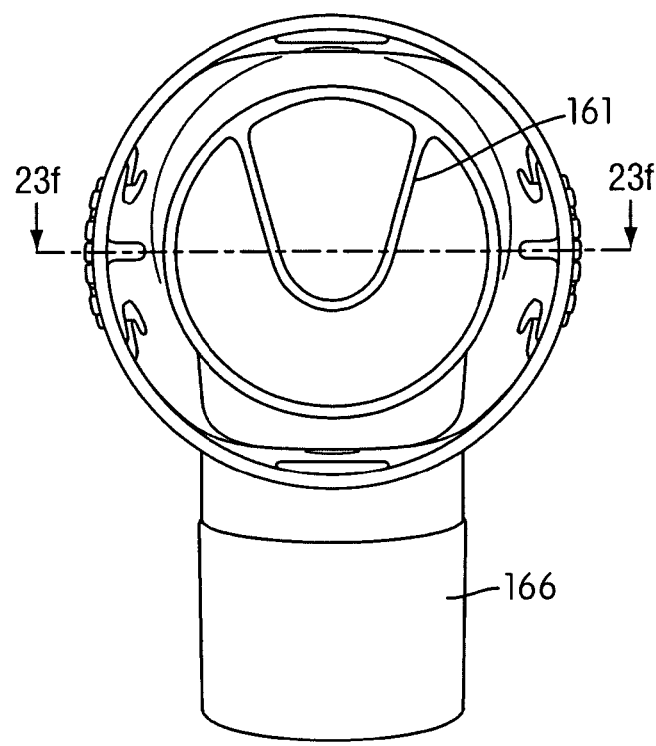
Figure 23F:
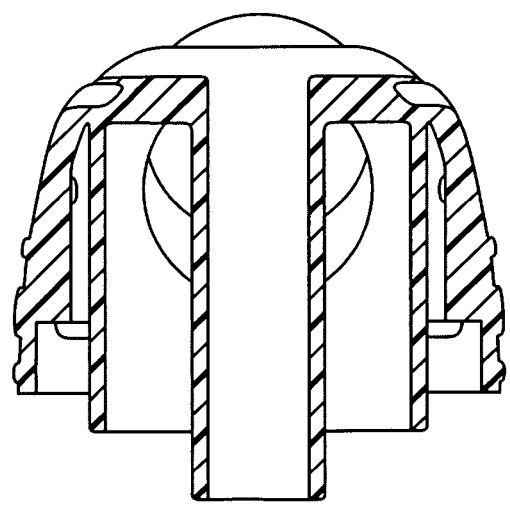
FIG. 23f is a cross-sectional view along line 23f-23f of the swivel elbow shown in FIG. 23e.
Figure 23G:
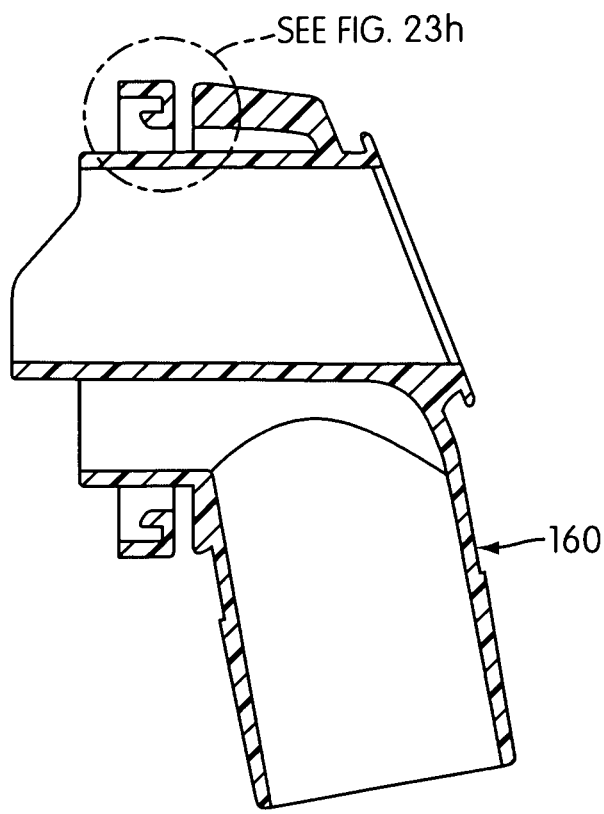
Figure 23H:
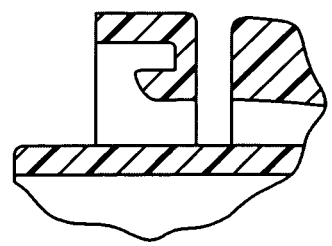
FIG. 23h is a detailed view of a portion of the swivel elbow shown in FIG. 23g.
Figure 23J:
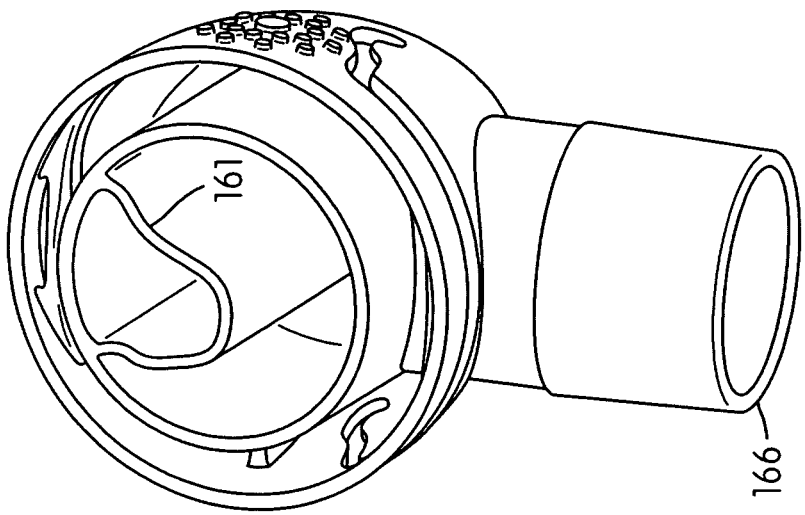
FIG. 23j is another rear perspective view of the swivel elbow shown in FIG. 22b at a slightly different angle.
Figure 23I:
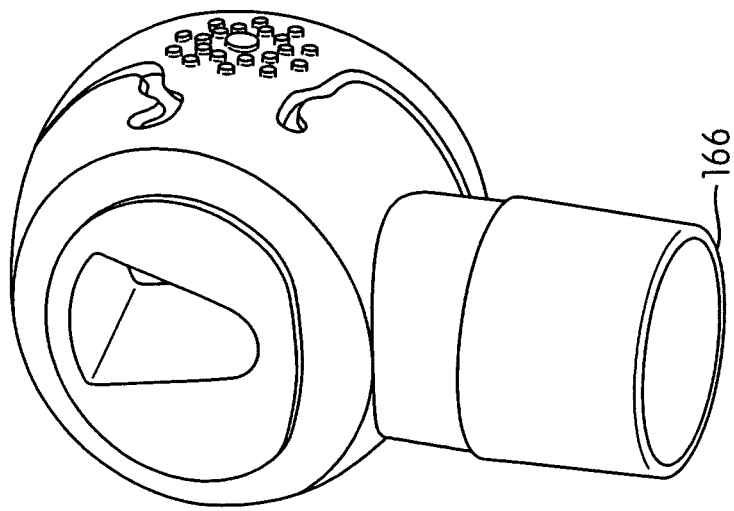
FIG. 23i is another front perspective view of the swivel elbow shown in FIG. 22a at a slightly different angle.
Figure 25A:
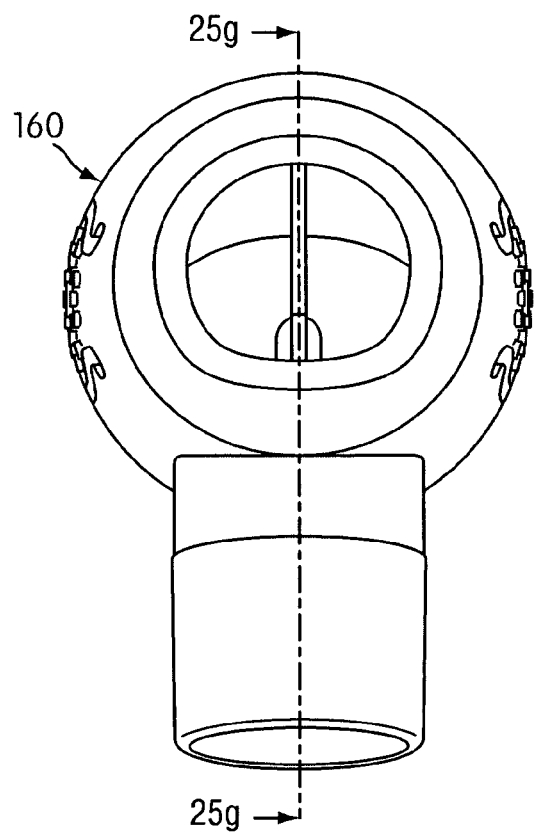
Figure 25B:
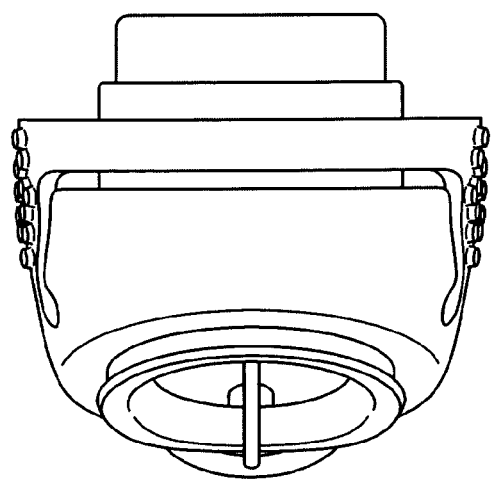
Figure 25C:
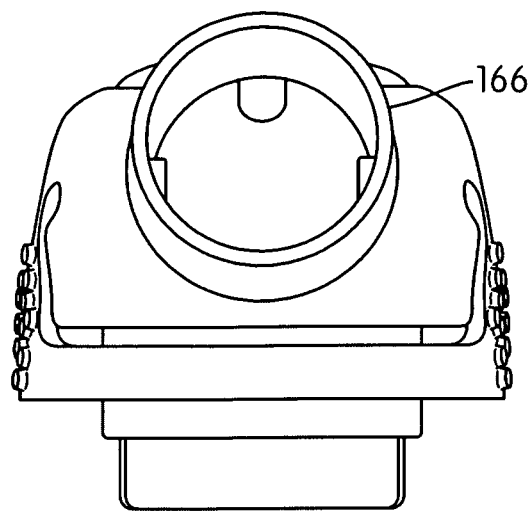
Figure 25D:
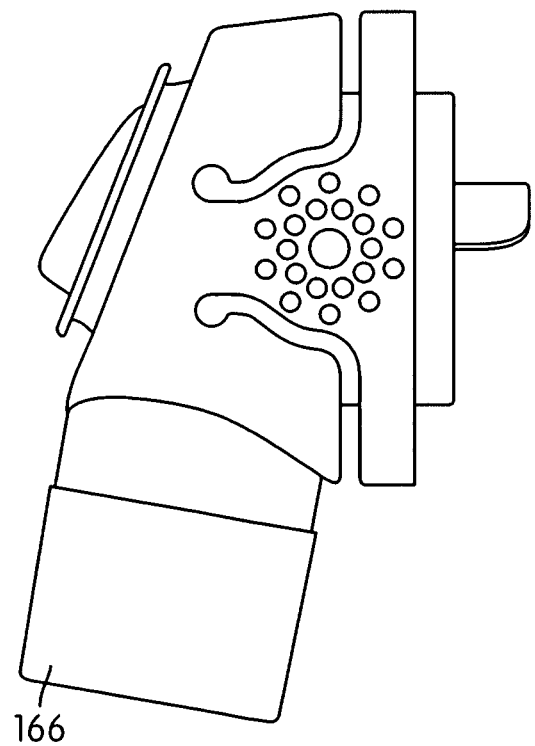
Figure 25E:
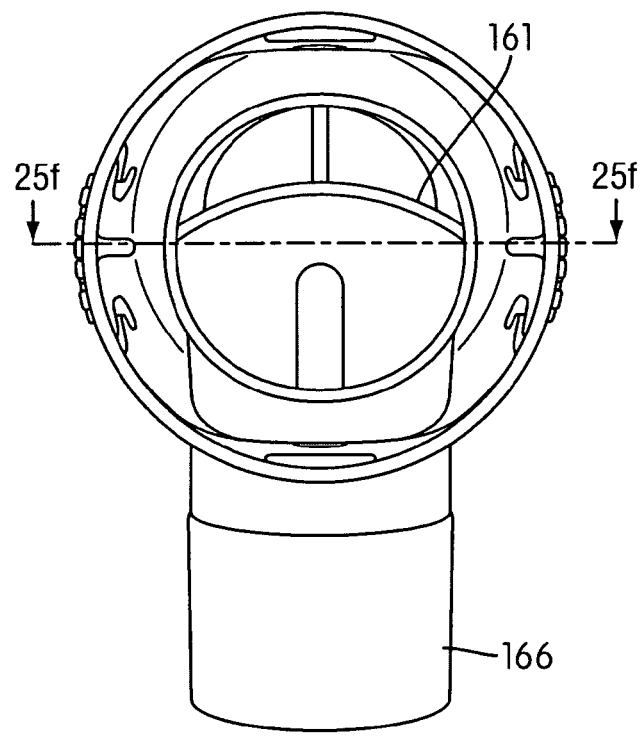
Figure 25F:
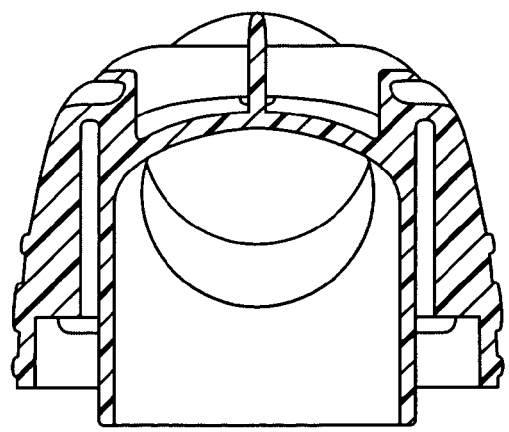
Figure 25G:
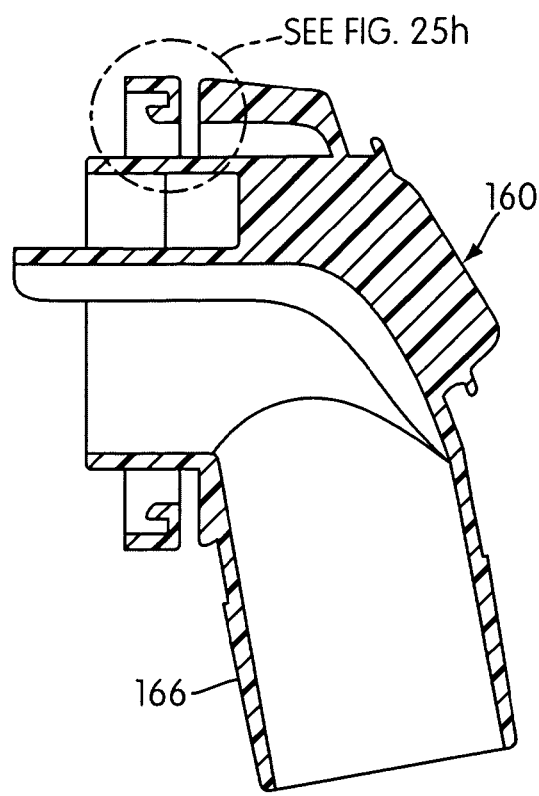
Figure 25H:
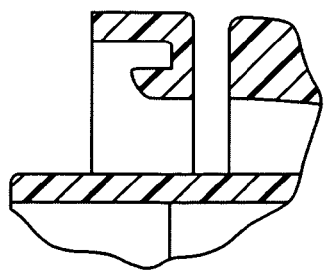
Figure 25J:
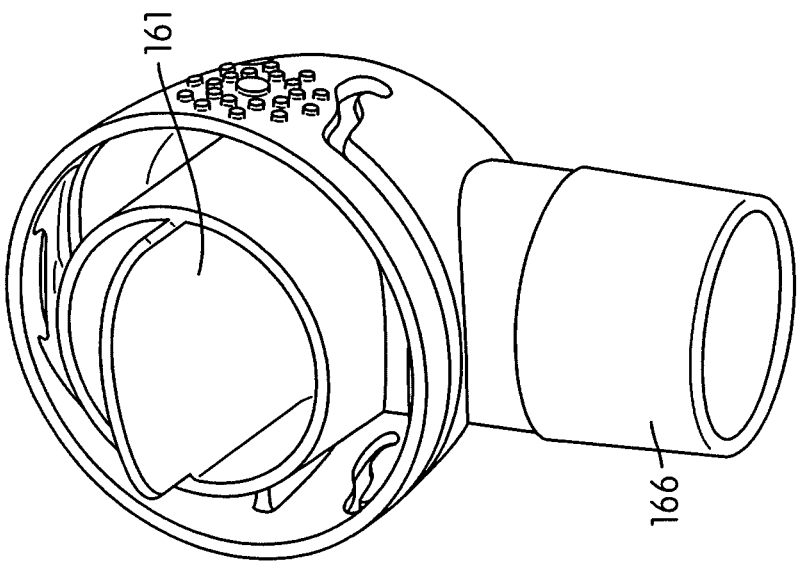
Figure 25I:
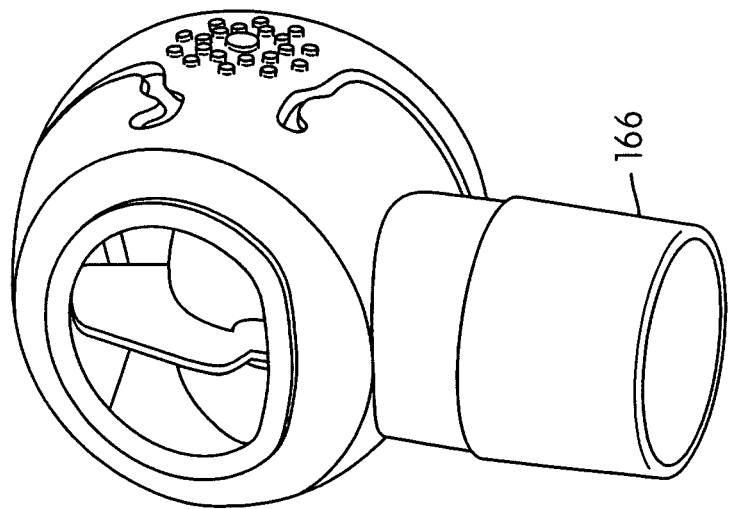

While the embodiment shown in FIGS. 14*a* to 15*j* does not include a baffle 161, it does incorporate other advantages of the invention, including its low profile. An embodiment of the present invention, a "deep" baffle 161 for use in mask assemblies 5 with large breathing cavities 35, is shown in FIGS. 16*a* and 16*b*.

FIGS. 30*a*-30*d* show a swivel elbow in accordance with an alternative embodiment of the invention similar to the embodiment shown in FIGS. 26*a*, 26*b*, 27*a*-27*j*. In this embodiment there are two "C"-shaped baffles 161 (FIG. 30*c*). Air enters the elbow from a blower via a stem 166 and is directed to turn through approximately 90 degrees and passes into the mask cavity via the intake port 162 which is located in the center of the elbow. (FIGS. 30*b* and 30*d*). Air from the mask cavity passes out through the exhaust ports 164 which are located on the sides of the elbow and into vent cavity 308 (FIGS. 30*a* and 30*d*).

In order to provide sufficient exhaust flow, it is desirable that the exhaust port 164 have a low flow impedance. One way to achieve this is to have as large a cross-sectional area for the exhaust port 164 as possible. However, within a given elbow design, increasing the cross-sectional area of the exhaust port 164 comes at the expense of the inlet port 162. It is also desirable to have as low a flow impedance in the inlet port 162 as possible. Hence in designing the elbow 160, one must take into account the two apparently conflicting design goals.

In one embodiment the baffle 161 of the elbow 160 extends into the mask frame 10 and is molded in one piece. In another embodiment, the baffle 161 is split between the swivel elbow 160 and the mask frame 10, and the combination of the two provides a baffle 161 of sufficient length. In the latter embodiment, the swivel elbow 160 is suitable for use with shallow mask frames 10 that do not require a long overall baffle 161.

In another form, the baffle 161 is partly formed by the elbow 160 and partly by the frame 10. This configuration can be created in different forms or baffle shapes. When the baffle 161 is formed from the combination of elbow 160 and frame 10, it is possible to create a modular elbow design which can be used with a variety of different mask systems. In order to form a baffle 161 from the combination of frame 10 and elbow 160, a circular ring 400 is added to the frame.

The ring 400 extends the depth of a baffle 161 into the cavity 35 of the mask frame 10. In this way, the likelihood that fresh inlet air short circuits the mask cavity 35 is reduced. An end of the ring is close to the edge of the user's nose and hence this configuration assists to direct exhaled air from the nose towards the exhaust port 164. The use of a ring 400 molded into the frame 10 obviates the need to extend the baffle 161 of the swivel elbow 160 into the mask frame 10. While a long baffled elbow is suitable for mask assemblies with large cavities, it may not be suitable for mask assemblies with shallow cavities, since it may interfere with a patient's nose. Hence by the use of the combination of mask frame 10 with ring 400 and an elbow 160 with a short baffle, the same elbow 160 can be used on both shallow and large cavitied mask assemblies.

In one form of the invention, the baffle 161 is formed within a cylindrical portion of the elbow 160 adapted for connection to the frame. In the embodiment of the invention, shown in FIGS. 20*a* and 21*a* to 21*j*, the baffle 161 defines a centrally located exhaust port 164. Air from the blower passes around the outside of the exhaust port 164.

The construction of the elbow 160 in combination with the angle between the two generally cylindrical portions of the elbow 160 leads to a potential dead spot within the blower airflow path. Potential dead spots within the blower flow path represent an opportunity for an exhaust flow path. Hence in one form of the invention, e.g., see FIGS. 4a-4c, the exhaust flow path is positioned within the elbow 160 in what would otherwise be a dead spot for blower flow. Thus the cross-sectional area of the exhaust flow path can be increased without having a significant impact on the impedance of the blower flow path and/or an adverse effect on the undesirable noise that may be produced during washout. In this way, it is possible to increase the cross-sectional area of the exhaust flow path from 40% to 60% of the total cross-sectional area (equal to the area of the exhaust flow path and the area of blower flow path) at the entrance to the mask cavity 35.

Another advantage of the baffle 161 in accordance with the invention is that it does not present a significant flow impedance for the blower flow. While a variety of different baffle designs are possible, those which impede the flow path create a resistance to flow from the blower, causing a large pressure drop along the elbow 160 than would otherwise be the case. The larger the pressure drop in the elbow, the harder the blower must work in order to provide air at a given positive pressure. The harder the blower must work, the more noise is created by the blower, which makes it more difficult for a patient to sleep.

In one form of the invention, the elbow 160 comprises two cylindrical portions, a first portion adapted for connection to an air delivery tube 168 and having a first axis; and a second portion adapted for connection to the mask frame 10 and having a second axis, wherein the two axes are disposed at an interior angle of about 100 degrees. This contrasts with prior art elbows where two corresponding axes are disposed at an interior angle of 90 degrees.

A further advantage of a swivel elbow 160 in accordance with the invention is that it has a low height (the perpendicular distance it extends from the frame). This reduces the visual impact of the swivel elbow 160, reduces the bending moment of the swivel elbow 160 and reduces the "lever arm" effect of the swivel elbow 160.

FIGS. 5a to 5d show various views of the respiratory mask assembly 10 according to one embodiment of the present invention. FIG. 6a to 6m show several views of the respiratory mask assembly 10. FIGS. 7a to 7i show several views of the swivel elbow 160. The dimensions shown in FIGS. 5a to 7i are preferred illustrative embodiments that may be varied up to ±20%, and preferably ±10%, in embodiments.

Other advantages of a swivel elbow and mask frame 10 in accordance with a preferred embodiment of the invention include providing: (i) sufficient inlet area and optimized shape such that flow into the mask assembly 5 is not impeded; and (ii) sufficient outlet flow area that has, in addition, a smooth profile and no restrictions other than a final smooth tapered exit to provide a quiet vent. The latter advantage has been difficult to achieve prior to the present invention.

While the invention has been described with reference to a nasal mask, it is applicable to a nose and mouth mask, or mouth mask. Furthermore, while the invention has been described with reference to a swivel elbow 160, it is applicable to fixed elbows. In addition, while one form of the invention is applicable to a cushion 30 which includes a gusset portion 32, other forms of the invention can be used with cushions 30 that do not include a gusset portion 32.

It can thus be appreciated that the aspects of the present invention have been fully and effectively described. The foregoing specific embodiments have been provided to illustrate the structural and functional principles of the present invention, and are not intended to be limiting. To the contrary, the present invention is intended to encompass all modifications, alterations and substitutions within the spirit and scope of the detailed description.

What is claimed is:

1. An elbow for a respiratory mask comprising:
 (a) a first portion having a first axis and being adapted for connection to an air delivery conduit;
 (b) a second portion, having a second axis and being adapted for connection to a frame of the respiratory mask; and
 (c) a vent constructed and arranged to allow the passage of air from an interior of the respiratory mask to atmosphere;
 wherein the elbow further defines:
  (i) an inlet port to deliver incoming gas in a first direction to a breathing cavity defined by the mask, and
  (ii) an exhaust port separated from the inlet port by at least one baffle,
 wherein the baffle has at least one curved portion along an end face of the baffle, as viewed along an end of the second portion provided to the frame of the mask, and
 wherein the baffle is configured to direct exhaust gas away from the nasal breathing cavity via the vent in a second direction that is substantially opposite to the first direction and substantially parallel to the second axis, and the baffle and the inlet port are non-concentric.

2. The elbow according to claim 1, wherein the at least one baffle comprises a first and a second baffle situated across from one another.

3. The elbow according to claim 1, wherein the baffle is oriented in the elbow about a center line passing from a top of the elbow to a bottom of the elbow such that a bottom of the baffle is aligned with the bottom of the elbow.

4. The elbow according to claim 1, wherein the exhaust port is completely surrounded by the inlet port.

5. The elbow according to claim 1, wherein the baffle is substantially circular.

6. The elbow according to claim 1, wherein the baffle is oriented in the elbow about a center line passing from a right side of the elbow to a left side of the elbow.

7. The elbow according to claim 1, wherein the baffle further comprises a protrusion adapted to protrude into a breathing cavity of the mask.

8. The elbow according to claim 1, wherein the end of the second portion of the elbow further comprises:
 iii) a resilient collar that substantially surrounds a mating portion to define a receiving space between the collar and the mating portion, and wherein the collar is configured to flex outwardly upon entry of a flange, formed on the mask, into the receiving space until the second end portion reaches an operative position in which the collar flexes inwardly by virtue of the resiliency thereof so as to lock the flange with respect to the collar and thereby detachably couple the elbow to the mask.

9. The elbow according to claim 8, wherein the mating portion extends beyond the collar to facilitate alignment of the end of the second portion of the elbow with respect to the mask.

10. The elbow according to claim 8, wherein the elbow further comprises release portions on each side of the collar that are flexed towards one another to move the collar outwardly so as to allow the flange to move out of the receiving space to detach the elbow from the mask.

11. The elbow according to claim 1, further comprising:
c) a removable vent cover detachably connected to the elbow, wherein the vent cover includes a main body and at least one vent aperture for gas washout.

12. The elbow according to claim 11, wherein the vent cover is made of a resilient material.

13. The elbow according to claim 1, wherein the at least one baffle is M-shaped, V-shaped or C-shaped.

14. The elbow according to claim 1, wherein the exhaust port increases in area along the second direction.

15. The elbow according to claim 1, wherein the second portion has a cylindrically-shaped side wall, and the baffle includes at least one point of attachment to the cylindrically-shaped sidewall.

16. The elbow according to claim 15, wherein the at least one point of attachment includes two points of attachment.

17. A respiratory mask assembly comprising:
a) a mask frame further comprising at least one aperture;
b) a cushion; and
c) an elbow according to claim 1.

18. The mask assembly according to claim 17, wherein the aperture has a diameter between about 20 mm to about 40 mm.

19. The mask assembly according to claim 18, wherein the aperture further comprises a ring.

20. The mask assembly according to claim 19, wherein the ring further comprises an inner ring.

21. The mask assembly according to claim 20, wherein the inner ring is linked to an inner diameter of the aperture by at least one connector.

22. The mask assembly according to claim 21, wherein the at least one connector comprises at least one notch adapted to engage the elbow.

23. The mask assembly according to claim 20, wherein the ring further comprises an outer ring surrounding the inner ring.

24. The mask assembly according to claim 23, wherein the outer ring has a diameter between about 20 mm to about 40 mm.

25. The mask assembly according to claim 20, wherein the inner ring defines a cavity.

26. The mask assembly according to claim 25, wherein the cavity has a diameter between about 4 mm to about 12 mm.

27. The mask assembly according to claim 26, wherein the cavity has a diameter between about 6 mm to about 10 mm.

28. The mask assembly according to claim 17, wherein the aperture has a generally circular shape.

29. The mask assembly according to claim 17, wherein the cushion is adapted to be inserted into the mask frame to define a cavity surrounding a user's nose.

30. The mask assembly according to claim 17, further comprising a ring provided adjacent the aperture, the ring defining a passage that communicates between an inside of the frame and a second passage defined at least in part by the baffle of the elbow, to thereby define a combined passage leading from the inside of the frame towards the exhaust port.

31. The mask assembly according to claim 30, wherein the ring is concentric with the aperture of the frame.

32. An elbow for interconnecting a respiratory mask and an air delivery conduit, said elbow being constructed and arranged to deliver a supply of air at positive pressure to the respiratory mask and to allow the washout of $CO_2$ from the respiratory mask, said elbow comprising:
(i) a cylindrical first portion, having an axis aligned in a first direction and being adapted for connection to the air delivery conduit;
(ii) a cylindrical second portion, having an axis aligned in a second direction and being adapted for connection to a frame of the respiratory mask;
(iii) a vent orifice constructed and arranged to allow the passage of air from an interior of the respiratory mask to atmosphere; and
(iv) a baffle which separates an inlet port and an exhaust port and an edge of which directs air into an interior of the respiratory mask at a first angle, and which directs air from the interior of the respiratory mask to atmosphere via the vent orifice at a second angle, said first and said second angles being different by about 180 degrees, and which first and second angles are substantially parallel to said second direction,
wherein the baffle has at least one curved portion along an end face of the baffle, as viewed along an end of the cylindrical second portion provided to the frame of the mask, and the baffle and the inlet port are non-concentric.

33. The elbow according to claim 32, wherein the cylindrical second portion includes a side wall, and the baffle includes at least one point of attachment to the sidewall.

34. The elbow according to claim 33, wherein the at least one point of attachment includes two points of attachment.

* * * * *